(12) United States Patent
Thorson et al.

(10) Patent No.: US 11,466,045 B2
(45) Date of Patent: Oct. 11, 2022

(54) MITHRAMYCIN OXIME DERIVATIVES HAVING INCREASED SELECTIVITY AND ANTI-CANCER ACTIVITY

(71) Applicant: University of Kentucky Research Foundation, Lexington, KY (US)

(72) Inventors: Jon S. Thorson, Lexington, KY (US);
Jurgen Rohr, Lexington, KY (US);
Markos Leggas, Lexington, KY (US);
Joseph M. Eckenrode, Lexington, KY (US); Yinan Zhang, Jiangsu (CN);
Yang Liu, Lexington, KY (US);
Jianjun Zhang, Lexington, KY (US);
Khaled Attia Shaaban Mahmoud, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/670,707

(22) Filed: Oct. 31, 2019

(65) Prior Publication Data
US 2020/0131218 A1   Apr. 30, 2020

Related U.S. Application Data

(60) Provisional application No. 62/753,205, filed on Oct. 31, 2018.

(51) Int. Cl.
*C07H 15/24* (2006.01)
*A61P 35/00* (2006.01)
*C07H 15/26* (2006.01)

(52) U.S. Cl.
CPC .............. *C07H 15/24* (2013.01); *A61P 35/00* (2018.01); *C07H 15/26* (2013.01)

(58) Field of Classification Search
CPC .......... C07H 15/24; C07H 15/26; A61P 35/00
USPC ........................................................ 514/33
See application file for complete search history.

(56) References Cited

U.S. PATENT DOCUMENTS 9,447,135 B2   9/2016   Rohr et al.

FOREIGN PATENT DOCUMENTS

WO   WO 2014093652 A1 * 6/2014

OTHER PUBLICATIONS

Kumar et al. (J. Med. Chem. 1980, 23, 376-379).*
Kofman, S., Perlia, C. P, Economou, S. G. Mithramycin in the treatment of metastatic ewing's sarcoma. Cancer 1973, 31, 889-893.
Balamuth, N., Womer, R. B.: Ewing's sarcoma, Lancet Oncol. 2010, 11, 184-192.
Kofman, S.; Medrek, T. J.; Alexander, R. W. Mithramycin in the treatment of embryonal cancer. Cancer 1964, 17, 938-948.
Delattre, O.; Zucman, J.; Plougastel, B.; Desmaze, C.; Melot, T.; Peter, M.; Kovar, H.; Joubert, I.; de Jong, P.; Rouleau, G. Gene fusion with an ETS DNA-binding domain caused by chromosome translocation in human tumours. Nature 1992, 359, 162.
May, W. A.; Arvand, A.; Thompson, A. D.; Braun, B. S.; Wright, M.; Denny, C. T. EWS/FLI1—induced manic fringe renders NIH 3T3 cells tumorigenic. Nat. Genet. 1997, 17, 495-497.
Tomlins, S.A., Rhodes, D.R., Perner, S., Dhanasekaran, S.M., Mehra, R., Sun, X.W., Varambally, S., Cao, X., Tchinda, J., Kuefer, R. and Lee, C. Recurrent fusion of TMPRSS2 and ETS transcription factor genes in prostate cancer. Science, 2005, 310,644-648.
Scott, D.; Chen, J. M.; Bae, Y.; Rohr, J. Semi-synthetic mithramycin SA derivatives with improved anti-cancer activity. Chem. Biol. Drug. Des. 2013, 81, 615-624.
Hou, C.; Weidenbach, S.; Cano, K. E.; Wang, Z.; Mitra, P.; Ivanov, D. N.; Rohr, J.; Tsodikov, O. V. Structures of mithramycin analogues bound to DNA and implications for targeting transcription factor FLI1. Nucleic Acids Res. 2016, 44, 8990-9004.
Osgood, C. L.; Maloney, N.; Kidd, C. G.; Kitcheúñunez, L. E.; González-Sabín, Z.; Helman, L. J.; Morís, F.; Grohar, P. J. Identification of mithramycin analogues with improved targeting of the EWS-FLI1 transcription factor. Clin. Cancer Res. 2016, 22, 4105-4118.
Garcia-Aragoncillo, E., J. Carrillo, E. Lalli, N. Agra, G. Gomez-Lopez, A. Pestana, and J. Alonso. "DAX1, a direct target of EWS/FLI1 oncoprotein, is a principal regulator of cell-cycle progression in ewing's tumor cells." Oncogene 2008, 27, 6034-6043.
Grohar, P. J.; Woldemichael, G. M.; Griffin, L. B.; Mendoza, A.; Chen, Q.-R.; Yeung, C.; Currier, D. G.; Davis, S.; Khanna, C.; Khan, J. Identification of an inhibitor of the EWS-FLI1 oncogenic transcription factor by high-throughput screening. J. Natl. Cancer Inst. 2011, 103, 962-978.
Mitra, P., et al., Development of Mithramycin Analogues with Increased Selectivity toward ETS Transcription Factor Expressing Cancers, J. Med. Chem. 2018 (61)8001.
Tevyashova, A.N., et al., Modification of the antibiotic olivomycin I at the 2¢-keto group of the side chain. Novel derivatives, antitumor and topoisomerase I-poisoning activity, J. Antibiotics (2009) 62, 37-41.

* cited by examiner

*Primary Examiner* — Shaojia A Jiang
*Assistant Examiner* — Michael C Henry
(74) *Attorney, Agent, or Firm* — Stites & Harbison PLLC; Mandy Wilson Decker

(57) ABSTRACT

Compounds described herein are mithramycin (MTM) oxide (OX) derivatives and MTM Hydrazine (HY) derivatives. These compounds are useful for treatment of cancers and neuro-diseases.

13 Claims, 12 Drawing Sheets
Specification includes a Sequence Listing.

SEQUENCE LISTING

```
<160> NUMBER OF SEQ ID NOS: 4

<210> SEQ ID NO 1
<211> LENGTH: 98
<212> TYPE: PRT
<213> ORGANISM: Homo sapiens

<400> SEQUENCE: 1

Pro Gly Ser Gly Gln Ile Gln Leu Trp Gln Phe Leu Leu Glu Leu Leu
1               5                   10                  15

Ser Asp Ser Ala Asn Ala Ser Cys Ile Thr Trp Glu Gly Thr Asn Gly
            20                  25                  30

Glu Phe Lys Met Thr Asp Pro Asp Glu Val Ala Arg Arg Trp Gly Glu
        35                  40                  45

Arg Lys Ser Lys Pro Asn Met Asn Tyr Asp Lys Leu Ser Arg Ala Leu
50                  55                  60

Arg Tyr Tyr Tyr Asp Lys Asn Ile Met Thr Lys Val His Gly Lys Arg
65                  70                  75                  80

Tyr Ala Tyr Lys Phe Asp Phe His Gly Ile Ala Gln Ala Leu Gln Pro
                85                  90                  95

His Pro

<210> SEQ ID NO 2
<211> LENGTH: 98
<212> TYPE: PRT
<213> ORGANISM: Homo sapiens

<400> SEQUENCE: 2

Pro Gly Ser Gly Gln Ile Gln Leu Trp Gln Phe Leu Leu Glu Leu Leu
1               5                   10                  15

Ser Asp Ser Ser Asn Ser Ser Cys Ile Thr Trp Glu Gly Thr Asn Gly
            20                  25                  30

Glu Phe Lys Met Thr Asp Pro Asp Glu Val Ala Arg Arg Trp Gly Glu
        35                  40                  45
```

```
Arg Lys Ser Lys Pro Asn Met Asn Tyr Asp Lys Leu Ser Arg Ala Leu
         50                  55                  60

Arg Tyr Tyr Tyr Asp Lys Asn Ile Met Thr Lys Val His Gly Lys Arg
 65                  70                  75                  80

Tyr Ala Tyr Lys Phe Asp Phe His Gly Ile Ala Gln Ala Leu Gln Pro
                     85                  90                  95

His Pro

<210> SEQ ID NO 3
<211> LENGTH: 452
<212> TYPE: PRT
<213> ORGANISM: Homo sapiens

<400> SEQUENCE: 3

Met Asp Gly Thr Ile Lys Glu Ala Leu Ser Val Val Ser Asp Asp Gln
 1               5                  10                  15

Ser Leu Phe Asp Ser Ala Tyr Gly Ala Ala His Leu Pro Lys Ala
                 20                  25                  30

Asp Met Thr Ala Ser Gly Ser Pro Asp Tyr Gly Gln Pro His Lys Ile
                 35                  40                  45

Asn Pro Leu Pro Pro Gln Gln Glu Trp Ile Asn Gln Pro Val Arg Val
 50                  55                  60

Asn Val Lys Arg Glu Tyr Asp His Met Asn Gly Ser Arg Glu Ser Pro
 65                  70                  75                  80

Val Asp Cys Ser Val Ser Lys Cys Ser Lys Leu Val Gly Gly Gly Glu
                 85                  90                  95

Ser Asn Pro Met Asn Tyr Asn Ser Tyr Met Asp Glu Lys Asn Gly Pro
                100                 105                 110

Pro Pro Pro Asn Met Thr Thr Asn Glu Arg Arg Val Ile Val Pro Ala
                115                 120                 125

Asp Pro Thr Leu Trp Thr Gln Glu His Val Arg Gln Trp Leu Glu Trp
                130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
                180                 185                 190

Tyr Leu Arg Glu Ser Ser Leu Leu Ala Tyr Asn Thr Thr Ser His Thr
                195                 200                 205

Asp Gln Ser Ser Arg Leu Ser Val Lys Glu Asp Pro Ser Tyr Asp Ser
                210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
                260                 265                 270

Leu Ala Asn Pro Gly Ser Gly Gln Ile Gln Leu Trp Gln Phe Leu Leu
                275                 280                 285

Glu Leu Leu Ser Asp Ser Ala Asn Ala Ser Cys Ile Thr Trp Glu Gly
                290                 295                 300

Thr Asn Gly Glu Phe Lys Met Thr Asp Pro Asp Glu Val Ala Arg Arg
305                 310                 315                 320
```

```
Trp Gly Glu Arg Lys Ser Lys Pro Asn Met Asn Tyr Asp Lys Leu Ser
                325                 330                 335

Arg Ala Leu Arg Tyr Tyr Asp Lys Asn Ile Met Thr Lys Val His
                340                 345                 350

Gly Lys Arg Tyr Ala Tyr Lys Phe Asp Phe His Gly Ile Ala Gln Ala
                355                 360                 365

Leu Gln Pro His Pro Thr Glu Ser Ser Met Tyr Lys Tyr Pro Ser Asp
            370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
                420                 425                 430

Asn Pro Asn Val Pro Arg His Pro Asn Thr His Val Pro Ser His Leu
                435                 440                 445

Gly Ser Tyr Tyr
            450

<210> SEQ ID NO 4
<211> LENGTH: 460
<212> TYPE: PRT
<213> ORGANISM: Homo sapiens

<400> SEQUENCE: 4

Met Ile Gln Thr Val Pro Asp Pro Ala Ala His Ile Lys Glu Ala Leu
1               5                   10                  15

Ser Val Val Ser Asp Glu Gln Ser Leu Phe Glu Cys Ala Tyr Gly Thr
                20                  25                  30

Pro His Leu Ala Lys Thr Glu Met Thr Ala Ser Ser Ser Ser Asp Tyr
            35                  40                  45

Gly Gln Thr Ser Lys Met Ser Pro Arg Val Pro Gln Gln Asp Trp Leu
        50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
                100                 105                 110

Ser Tyr Met Glu Glu Lys His Met Pro Pro Pro Asn Met Thr Thr Asn
            115                 120                 125

Glu Arg Arg Val Ile Val Pro Ala Asp Pro Thr Leu Trp Ser Thr Asp
        130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
                180                 185                 190

Asp Ile Leu Leu Ser His Leu His Tyr Leu Arg Glu Thr Pro Leu Pro
            195                 200                 205

His Leu Thr Ser Asp Asp Val Asp Lys Ala Leu Gln Asn Ser Pro Arg
        210                 215                 220

Leu Met His Ala Arg Asn Thr Asp Leu Pro Tyr Glu Pro Pro Arg Arg
```

-continued

| | | | | | | | | | | | |
|---|---|---|---|---|---|---|---|---|---|---|---|
| | | | | 225 | | | 230 | | | 235 | 240 |
| Ser | Ala | Trp | Thr | Gly | His | Gly | His | Pro | Thr | Pro | Gln | Ser | Lys | Ala | Ala |
| | | | | 245 | | | | 250 | | | | 255 | |
| Gln | Pro | Ser | Pro | Ser | Thr | Val | Pro | Lys | Thr | Glu | Asp | Gln | Arg | Pro | Gln |
| | | | 260 | | | | | 265 | | | | 270 | |
| Leu | Asp | Pro | Tyr | Gln | Ile | Leu | Gly | Pro | Thr | Ser | Ser | Arg | Leu | Ala | Asn |
| | | 275 | | | | | 280 | | | | | 285 | |
| Pro | Gly | Ser | Gly | Gln | Ile | Gln | Leu | Trp | Gln | Phe | Leu | Leu | Glu | Leu | Leu |
| | 290 | | | | | 295 | | | | | 300 | |
| Ser | Asp | Ser | Ser | Asn | Ser | Ser | Cys | Ile | Thr | Trp | Glu | Gly | Thr | Asn | Gly |
| 305 | | | | | 310 | | | | | 315 | | | | | 320 |
| Glu | Phe | Lys | Met | Thr | Asp | Pro | Asp | Glu | Val | Ala | Arg | Arg | Trp | Gly | Glu |
| | | | | 325 | | | | 330 | | | | | 335 | |
| Arg | Lys | Ser | Lys | Pro | Asn | Met | Tyr | Asp | Lys | Leu | Ser | Arg | Ala | Leu | Arg |
| | | | 340 | | | | 345 | | | | 350 | |
| Tyr | Tyr | Tyr | Asp | Lys | Asn | Ile | Met | Thr | Lys | Val | His | Gly | Lys | Arg | Tyr |
| | | | 355 | | | | | 360 | | | | 365 | |
| Ala | Tyr | Lys | Phe | Asp | Phe | His | Gly | Ile | Ala | Gln | Ala | Leu | Gly | Pro | His |
| | 370 | | | | | 375 | | | | | 380 | |
| Gln | Gln | Glu | Ser | Ser | Leu | Tyr | Lys | Tyr | Pro | Ser | Asp | Leu | Pro | Tyr | Met |
| 385 | | | | | 390 | | | | | 395 | | | | | 400 |
| Gly | Ser | Tyr | His | Ala | His | Pro | Gln | Lys | Met | Asn | Phe | Val | Ala | Pro | His |
| | | | | 405 | | | | 410 | | | | 415 | |
| Pro | Pro | Ala | Leu | Pro | Val | Thr | Ser | Ser | Phe | Phe | Ala | Ala | Pro | Asn |
| | | | | 420 | | | | 425 | | | | 430 | |
| Pro | Tyr | Trp | Asn | Ser | Pro | Thr | Gly | Gly | Tyr | Pro | Asn | Thr | Arg | Leu | Pro |
| | | | 435 | | | | | 440 | | | | 445 | |
| Thr | Ser | His | Met | Pro | Ser | His | Leu | Gly | Thr | Tyr | Tyr |
| 450 | | | | | 455 | | | | | 460 |

MITHRAMYCIN OXIME DERIVATIVES HAVING INCREASED SELECTIVITY AND ANTI-CANCER ACTIVITY

RELATED APPLICATIONS

This application claims priority from U.S. Provisional Application Ser. No. 62/753,205 filed Dec. 31, 2018, the entire disclosure of which is incorporated herein by this reference.

GOVERNMENT INTEREST

This invention was made with government support under grant numbers UL1 TR001998 awarded by the National Institutes of Health, and grant number W81XWH-16-1-0477 awarded by the Department of Defense. The government has certain rights in the invention.

TECHNICAL FIELD

The present disclosure relates to compounds that are mithramycin (MTM) Oxime (OX) and MTM hydrazine (HY) derivatives and their use in the treatment of cancers and neuro-diseases.

BACKGROUND

All members of the erythroblast transformation-specific (ETS) transcription factor-family contain an Ets-domain, which consists of approximately 80 amino acids with four tryptophan repeats. The Ets-domain binds to double-stranded DNA of target genes containing a GGAA/T core motif and different flanking regions. Exemplary ETS transcription factors include friend leukemia integration 1 transcription factor (FLI1), v-ets avian erythroblastosis virus E26 oncogene-like transcription factor (ERG), and SPI1 or PU.1 transcription factor (SPI1).

ETS transcription factors can impact the expression of genes that are involved in various processes, such as cellular proliferation, differentiation, development, transformation, and apoptosis, and can have implications in connection with cancer. For example, FLI1 aberrant regulation is often associated with malignant transformation and is associated with chromosomal abnormalities in humans. In Ewing Sarcoma and primitive neuroectodermal tumors, for example, a chromosomal translocation results in a chimeric EWS-FLI1 fusion protein, containing the 5' region of EWS (Ewing sarcoma breakpoint region 1) and the 3' ETS region of Fli-1 (Delattre et al., Nature. 1992 Sep. 10; 359(6391):162-5). This oncoprotein acts as an aberrant transcriptional activator with strong transforming capabilities.

FLU and homologous transcription factors also have been implicated in human leukemias, such as Acute Myelogenous Leukemia (AML), involving loss or fusion of the tel gene, as well as other malignancies including clear-cell sarcoma, myxoid liposarcoma, desmoplastic small round cell tumor, myxoid chondrosarcoma, acute myeloid leukemia, congenital fibrosarcoma, prostate cancer and pancreatic cancer.

Another ETS transcription factor, ERG, is implicated in several cancers. Aberrant ERG regulation has been shown to be associated with diseases including Ewing sarcoma, acute myeloid leukemia (AML), prostate cancer, acute lymphoblatic leukemia (ALL), Alzheimer's disease (AD), and Down syndrome (DS).

Although ETS transcription factors such as FLI1, ERG, and SPI1 have been identified as critical targets in diseases such as cancer, no therapies have yet moved from bench to bedside that could impact the outcome of this disease. Ewing sarcoma, which affects primarily children and young adults is a difficult cancer to treat. Current therapy with a combination of severely cytotoxic drugs provides up to 60% long-term survival, but the cancer often recurs.

Mithramycin (MTM), an aureolic acid natural product previously used clinically against other cancers, was identified as a potent (low-nM) inhibitor of EWS-FLI1 in Ewing sarcoma cells (Grohar et al., (2011) Journal of the National Cancer Institute 103, 962-78). MTM exhibited similar high potency against Ewing sarcoma tumor cells in vitro and was efficacious in Ewing sarcoma mouse xenografts. Based on this study, MTM entered clinical trials at the National Cancer Institute as a Ewing sarcoma therapeutic (ClinicalTrials.gov, ID #NCT01610570) in 2012. Despite its strong inhibitory properties towards Ewing sarcoma, MTM was found to be highly toxic to non-Ewing cells, apparently because it inhibits Sp transcription factors.

Therefore, MTM analogues that are more selective against cancers cells are needed. MTM has high potential in the fight against cancer and new and improved analogues would find clinical relevance. A need thus exists to improve the performance, selectivity, and efficacy of MTM.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Mithramycin or mithramycin A (MTM) is an aureolic acid-type polyketide drug produced by various soil bacteria of the genus *Streptomyces* and was found to possess activity against a wide variety of human cancers.[1-2]

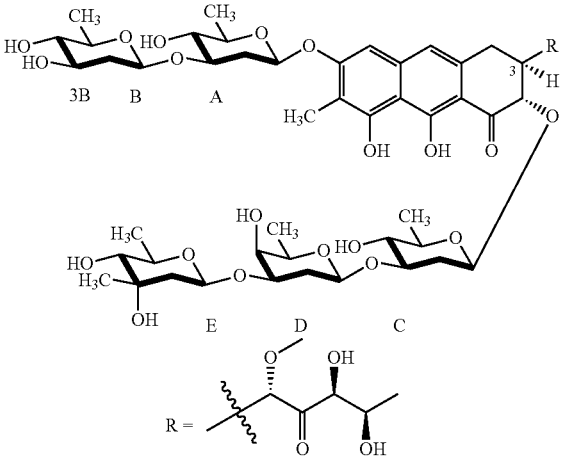

MTM was clinically evaluated in the 1960s and 70s as an agent for the chemotherapy of various cancers. As noted above, despite some remarkable success using MTM as a single agent, the results were mixed due to its narrow therapeutic index and considerable variation in patients' ability to tolerate the drug.[3] Another concern was the lack of understanding of MTM's mode-of-action. Taken together these limitations limited clinical use of MTM as a chemotherapeutic agent and it has now been largely abandoned.[4] Interest in MTM was renewed recently, after the drug was identified as the top inhibitor of the ETS transcription factor fusion, EWS-FLI1, in a screen of more than 50,000 natural products and synthetic compounds. FLI1 and ERG are ETS transcription factors that are expressed as fusions with EWS and are the primary cause of Ewing sarcoma.[5-6]

Aside from Ewing sarcoma, aberrant ETS transcription factors contribute significantly to the malignancy of prostate cancer, leukemia and lymphoma. With respect to prostate cancer, approximately 50% of patients express a truncated form of ERG as a result of the TMPRSS2 (transmembrane protease, serine 2)-ERG gene fusion.[7] Interestingly, the DNA binding domain of ERG and FLI1 is conserved and thus molecules that interfere with the activity of one should also inhibit the other. Given the importance of these aberrant transcription factors in driving malignancy, the clinical use of MTM gave investigators hope for a "targeted" therapy. This was tested in a recent national cancer institute (NCI) conducted clinical study where Ewing sarcoma patients were enrolled to assess the utility of MTM in a population of patients, all of whom express ETS fusions. Unfortunately, the results were inconclusive because the trial was terminated early, due to toxicities. As such, the development of less toxic and more selective analogues of MTM is highly desirable.

As disclosed herein, the present inventors have identified a number of derivatives. The MTM-OX and MTM-HY derivatives disclosed herein certain derivatives that are amino acid derivatives and multi-peptide derivatives. The MTM derivatives are useful for treatment of cancer or neuro-diseases associated with an aberrant erythroblast transformation-specific transcription factor, as disclosed herein.

The presently-disclosed subject matter includes a compound having the following formula:

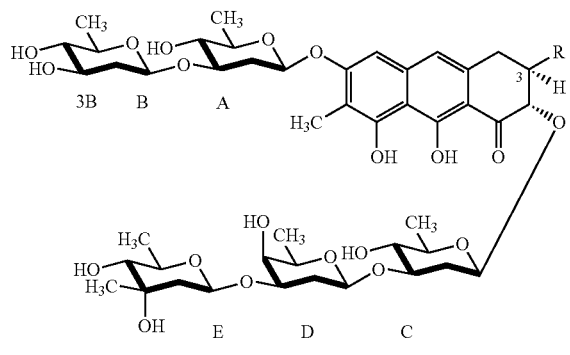

or a pharmaceutically acceptable salt thereof, in which R is

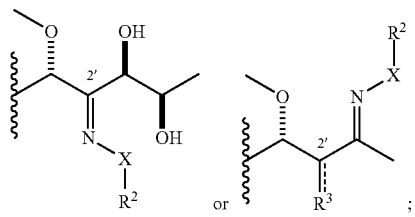

$R^2$ is H, OH, alkyl, alkylaryl, aryl, acyl, alkene, alkylalkene, alkyne, alkylalkyne, acyl, acylaryl, amino acid, amino acid dipeptide, acyl-amino acid, acyl-amino acid dipeptide; $R^3$ is O or OH; and X is O or NH.

In some embodiments, $R^2$ is acylaryl, acyl-amino acid, or acyl-amino acid dipeptide. In some embodiments, $R^2$ is acylaryl comprising a quinolone, a benzothizole, a phenyl, a pyridine, or an indol group. In some embodiments, $R^2$ comprises an amino acid or amino acid dipeptide group, or a substituted amino acid or amino acid dipeptide group.

The presently-disclosed subject matter includes a compound having the following formula:

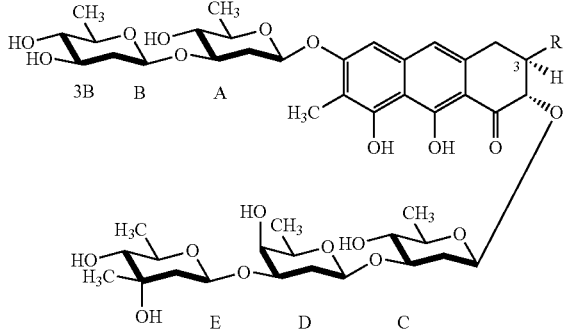

or a pharmaceutically acceptable salt thereof, in which R is chosen from at least one of the following:

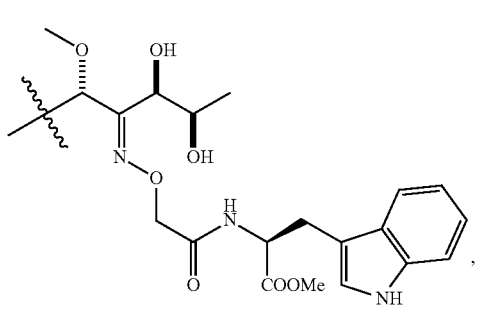

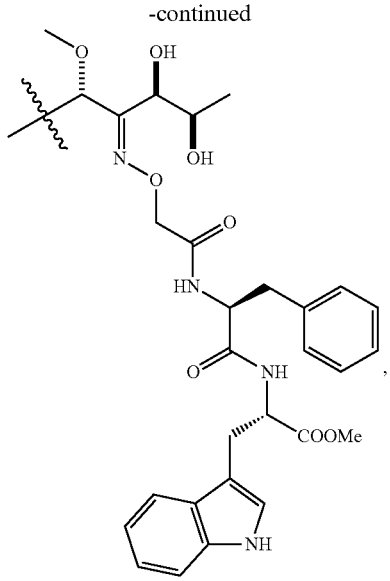
,
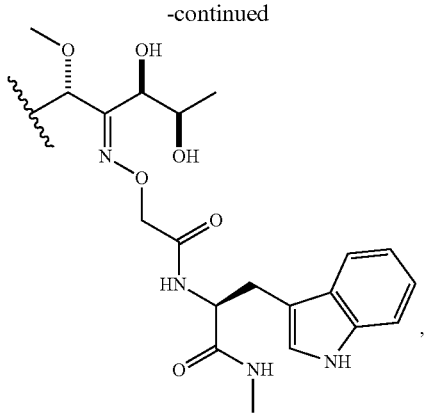
,
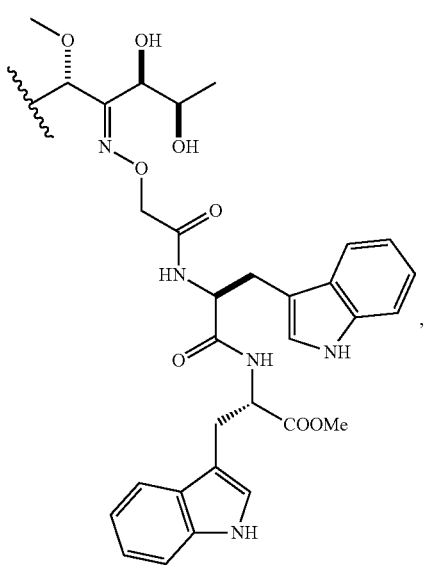
,
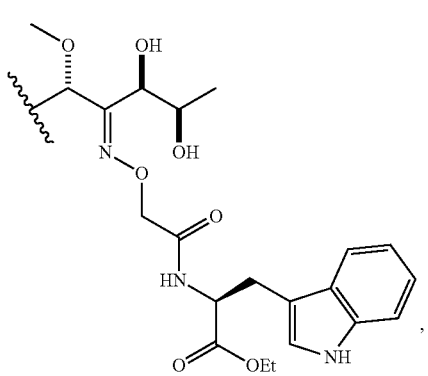
,
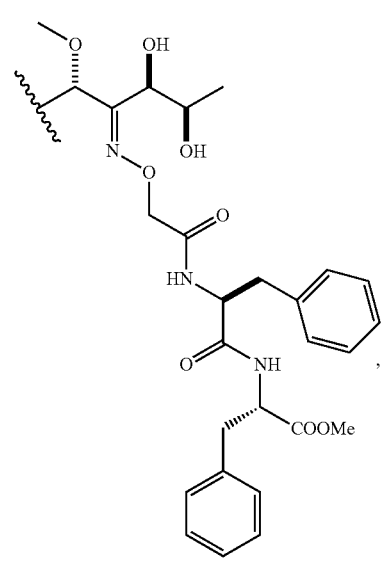
,
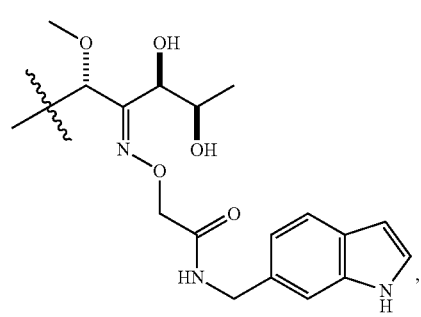
,
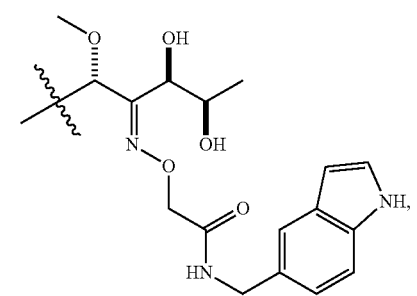

7
-continued
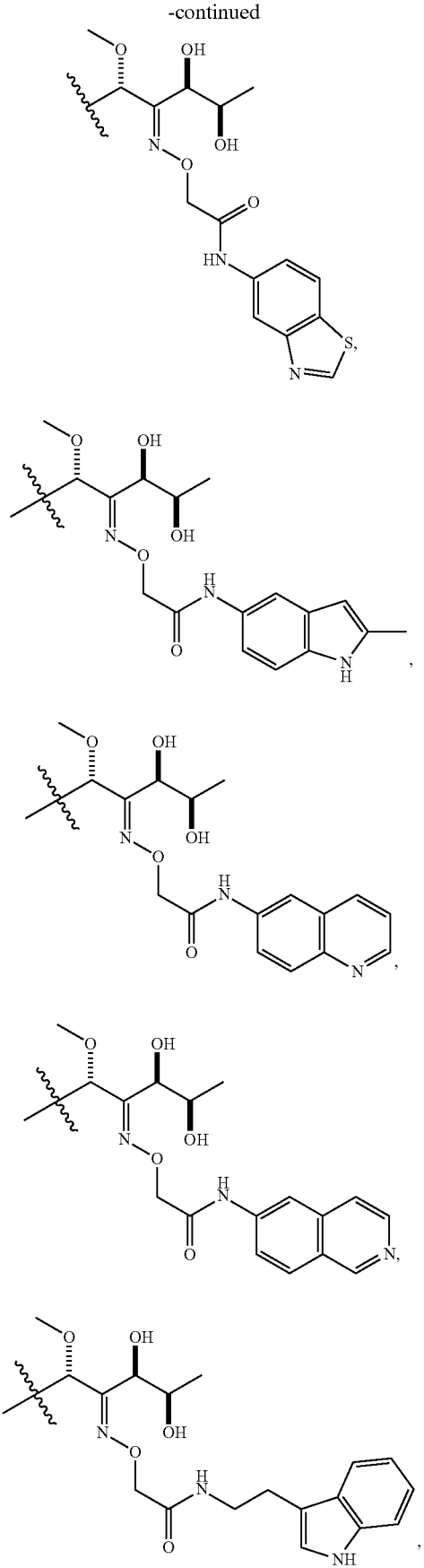
8
-continued
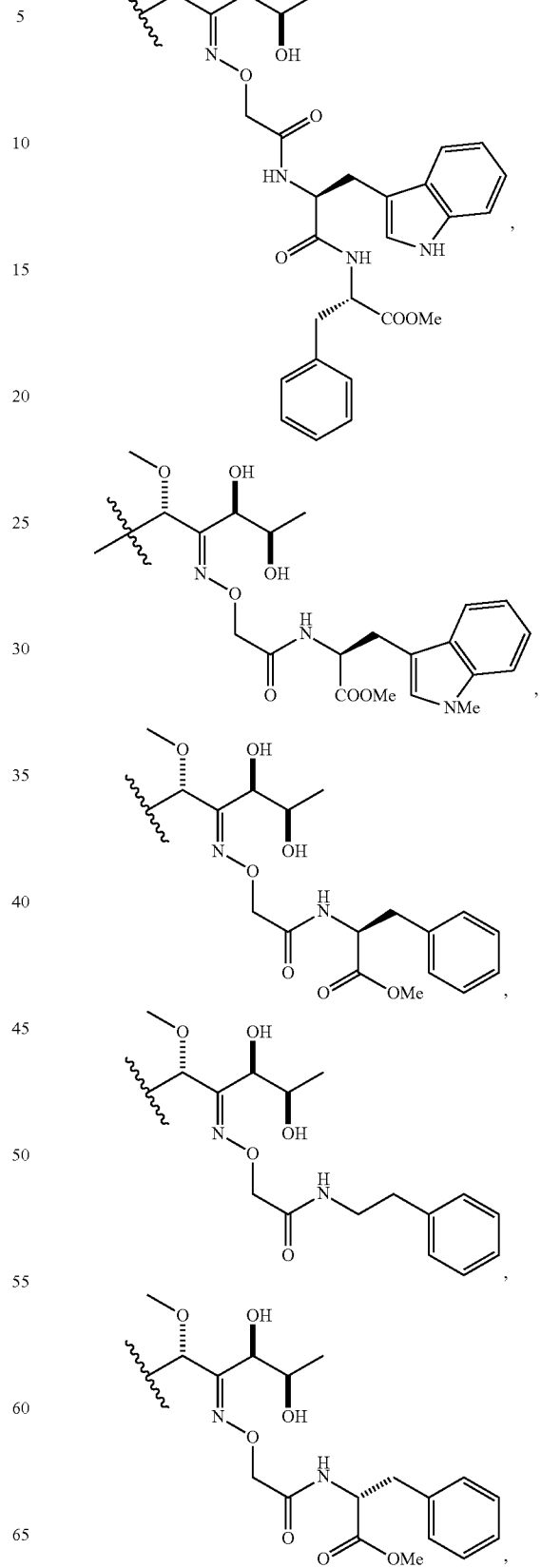

9
-continued
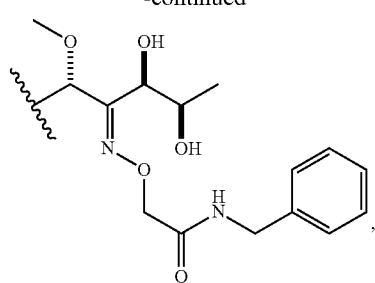
,
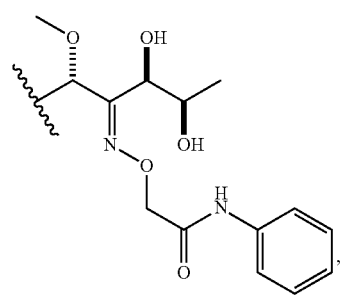
,
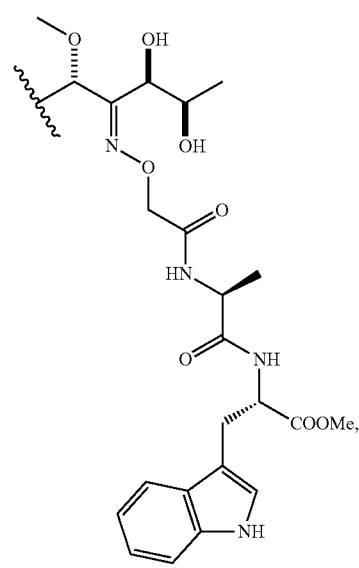
,
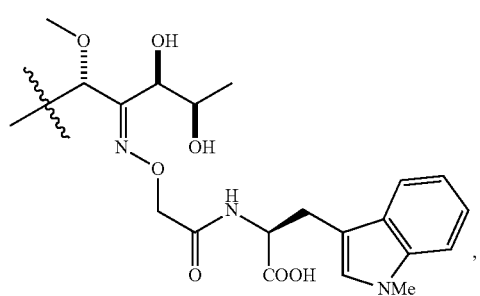
,
10
-continued
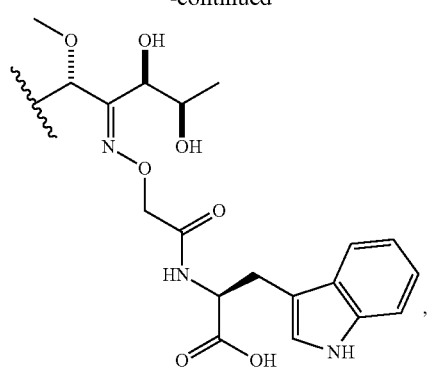
,
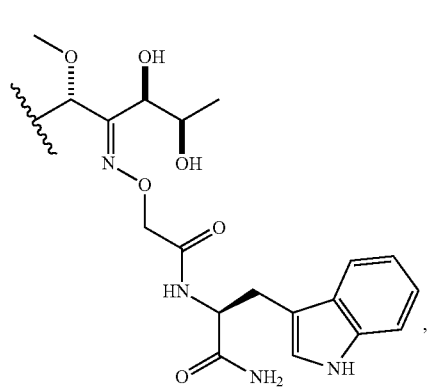
,
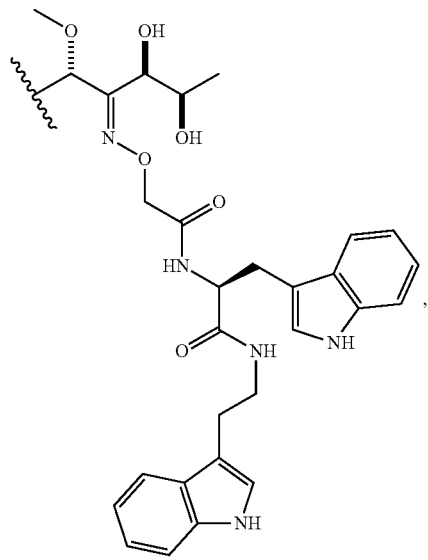
,
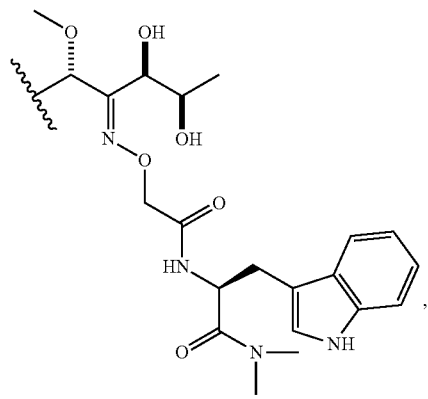
,

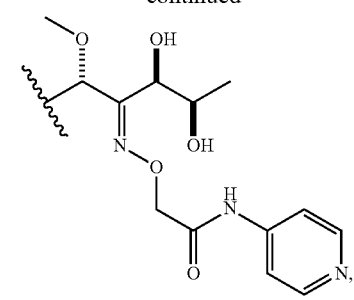
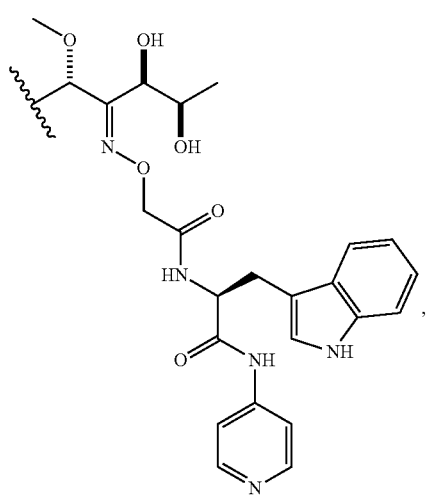
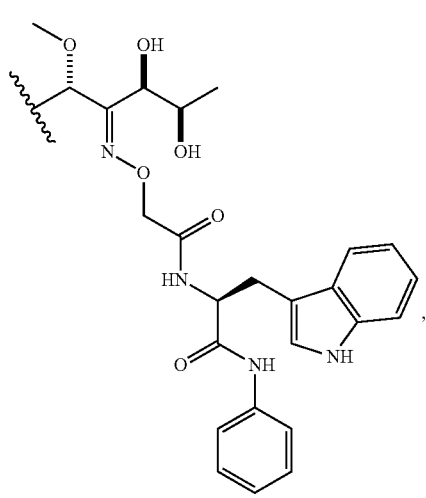
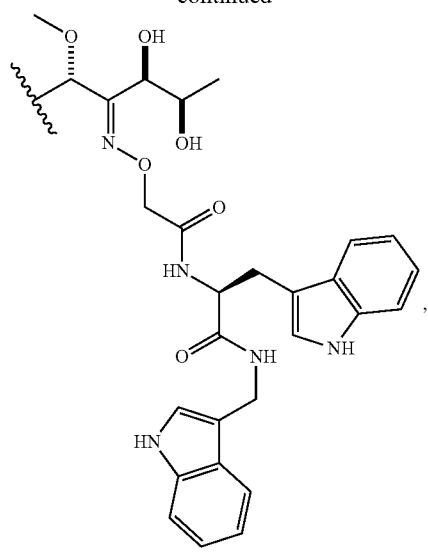
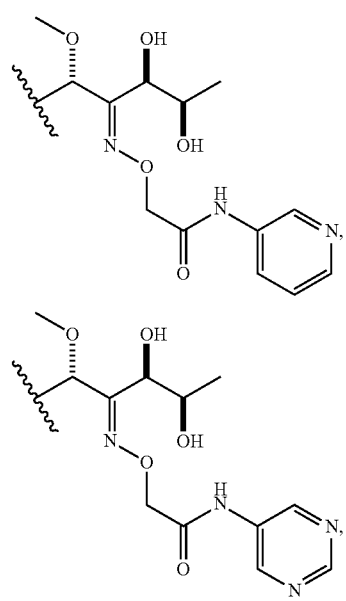
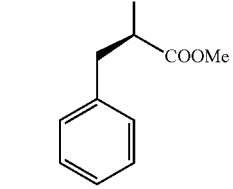

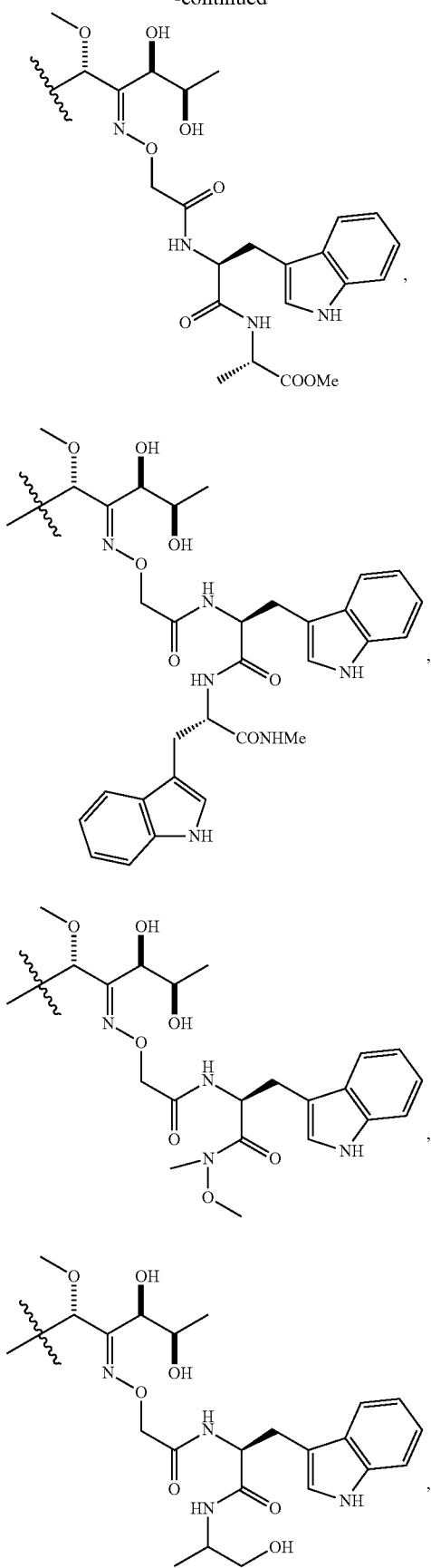
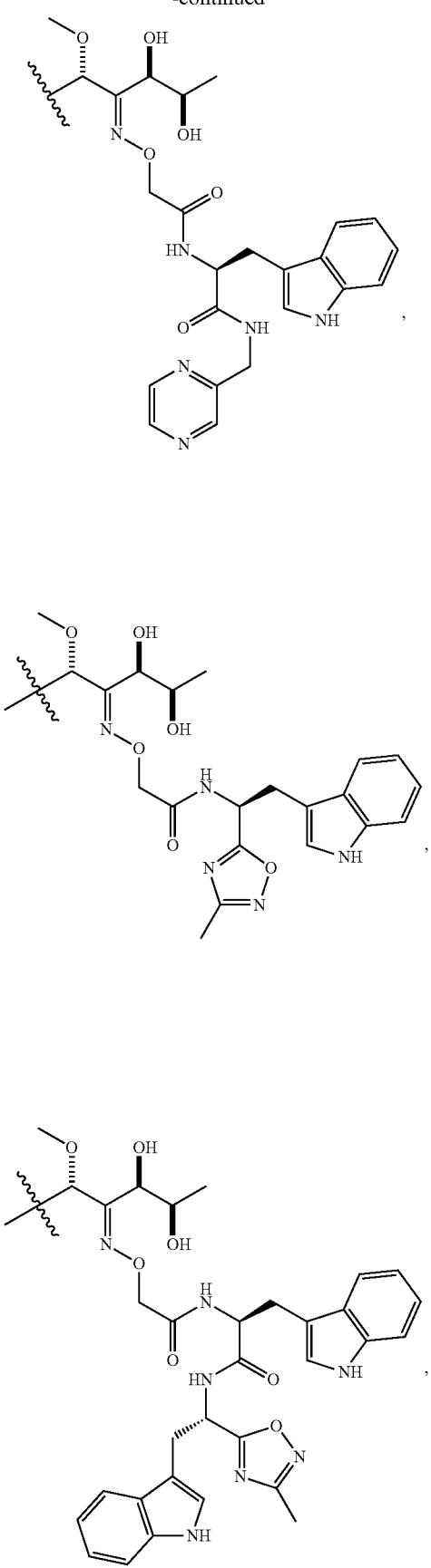

15
-continued
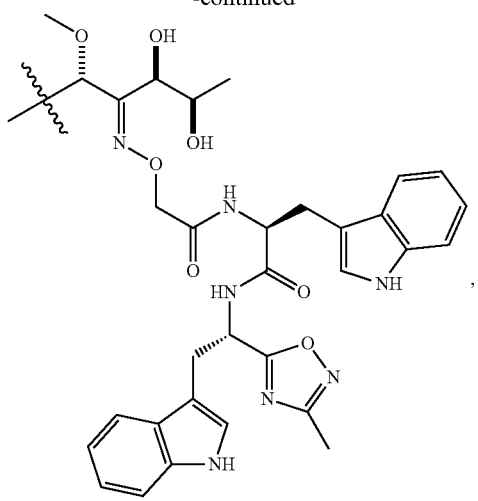
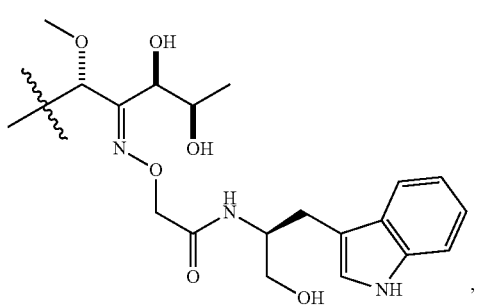
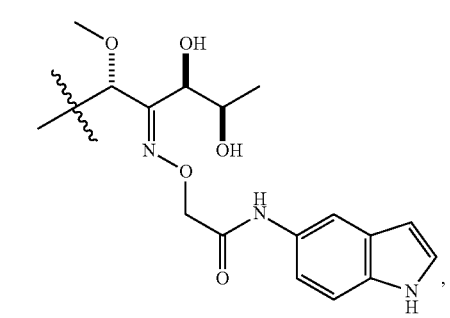
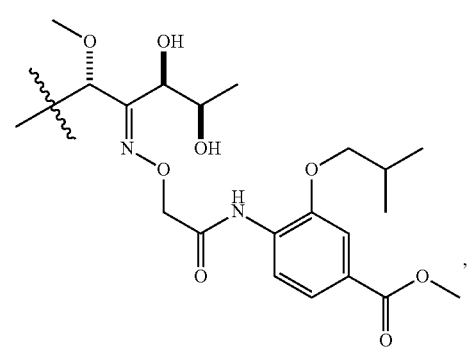
16
-continued
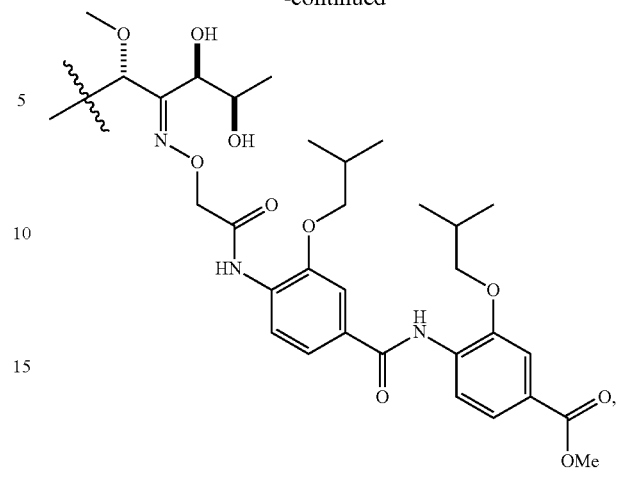
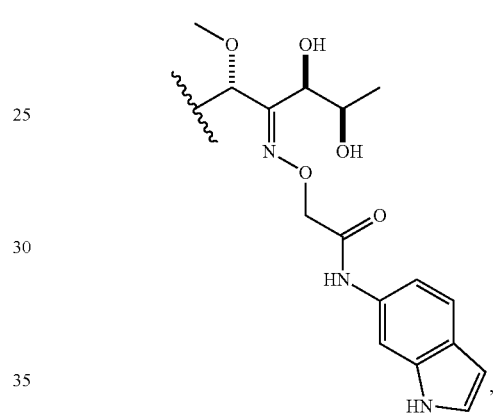
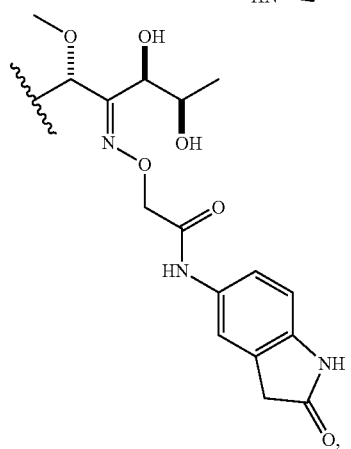
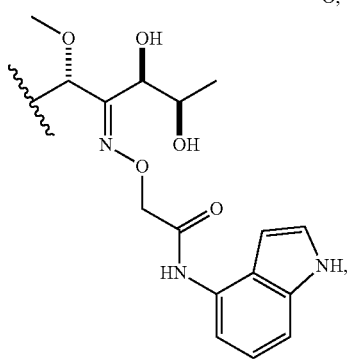

17
-continued
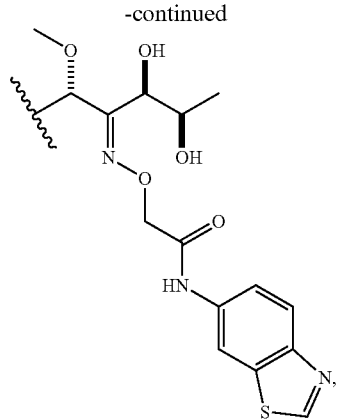
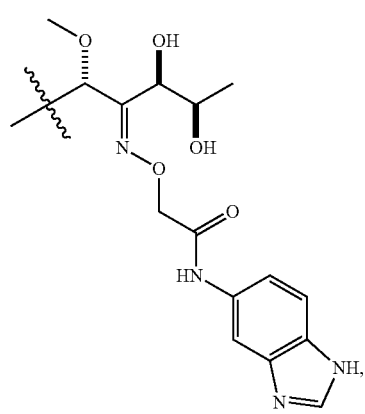
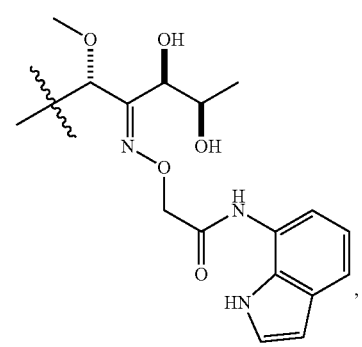
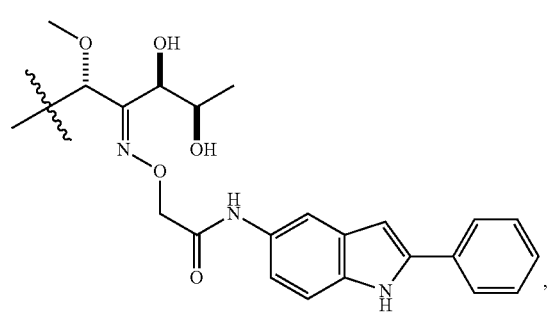
18
-continued
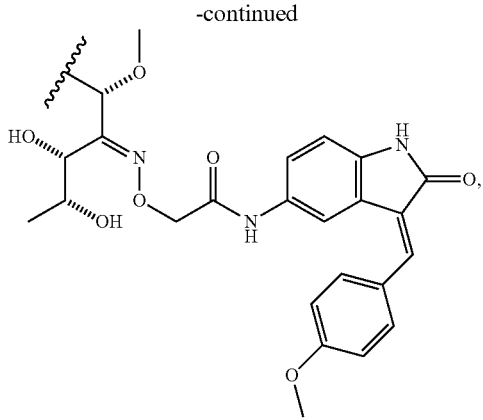
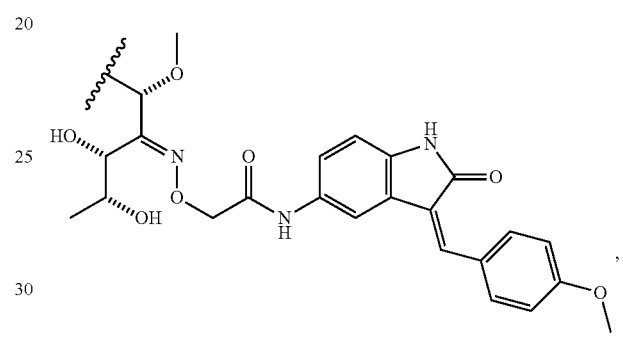
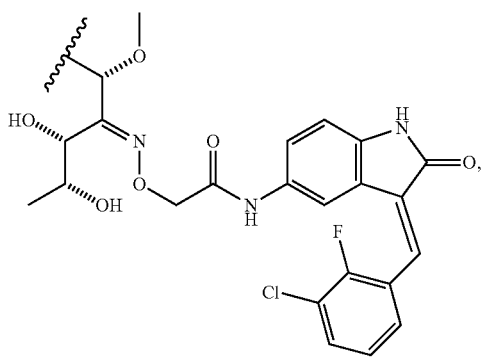
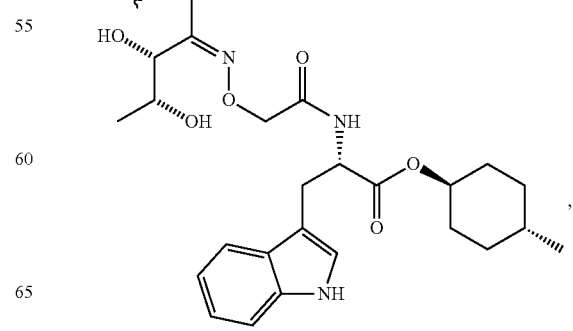

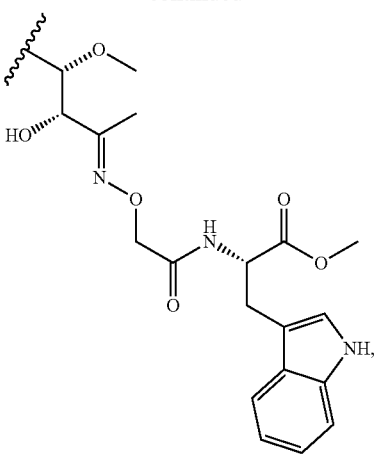
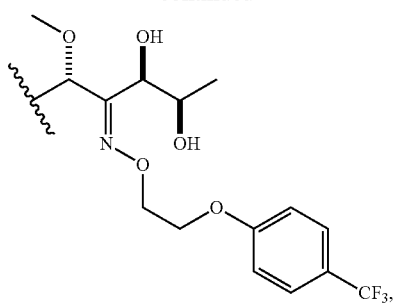
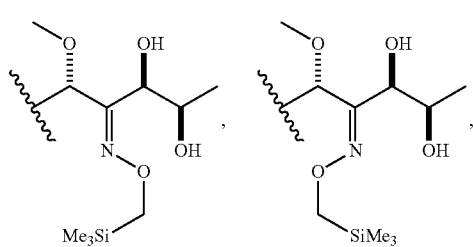
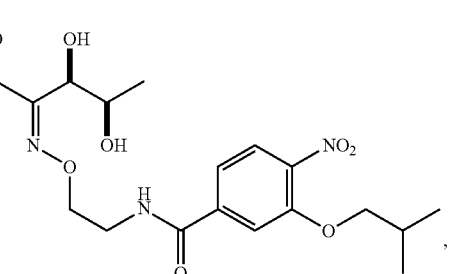
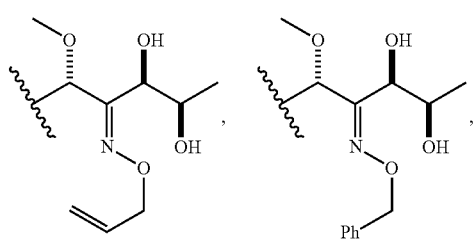
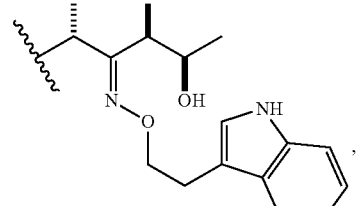
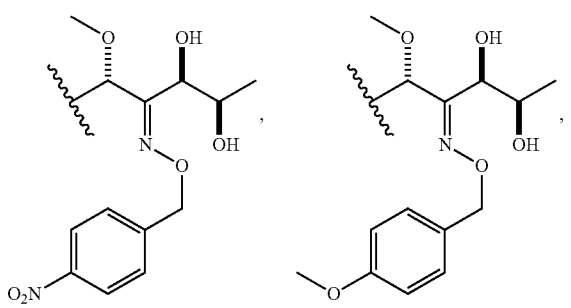
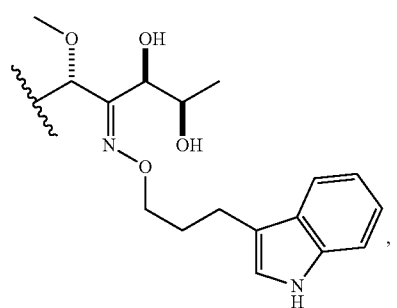
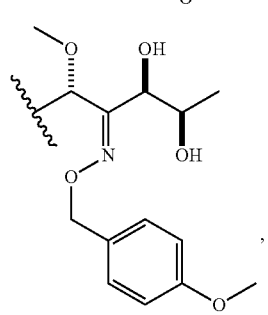
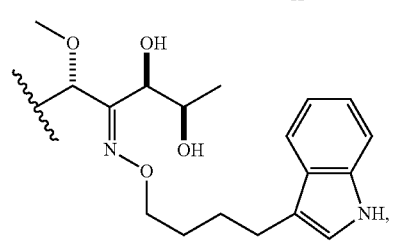

-continued

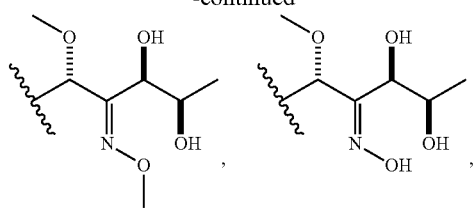
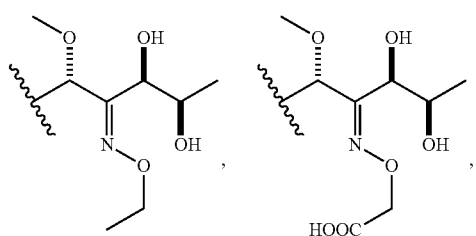
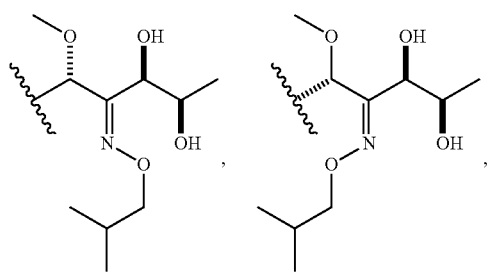
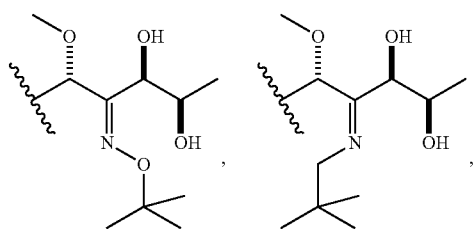
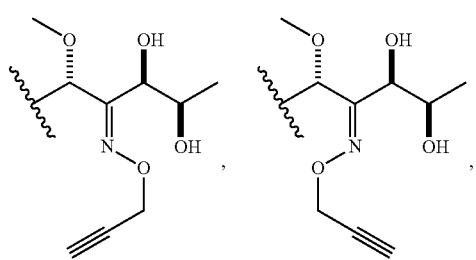
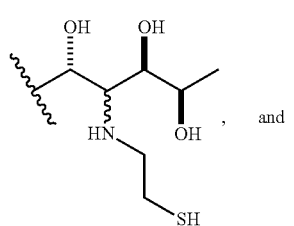

and

-continued

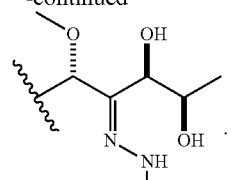
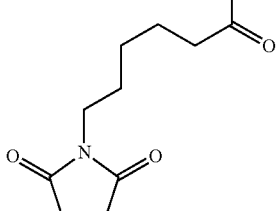

The presently-disclosed subject matter includes a method of treating cancer or neuro-disease in a patient in need thereof, the method comprising administering to the patient a therapeutically effective amount of a compound as disclosed herein or a pharmaceutically acceptable salt thereof. For example, in some embodiments, the compound is administered for the treatment of Ewing sarcoma, prostate cancer, colon cancer, lung cancer, leukemia or lymphoma.

The presently-disclosed subject matter includes a method for selectively modulating the activity of a target ETS transcription factor in a patient, including administering to the patient a therapeutically effective amount of a compound as disclosed herein or a pharmaceutically acceptable salt thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

BRIEF DESCRIPTION OF THE SEQUENCE LISTING

Figure 1A:
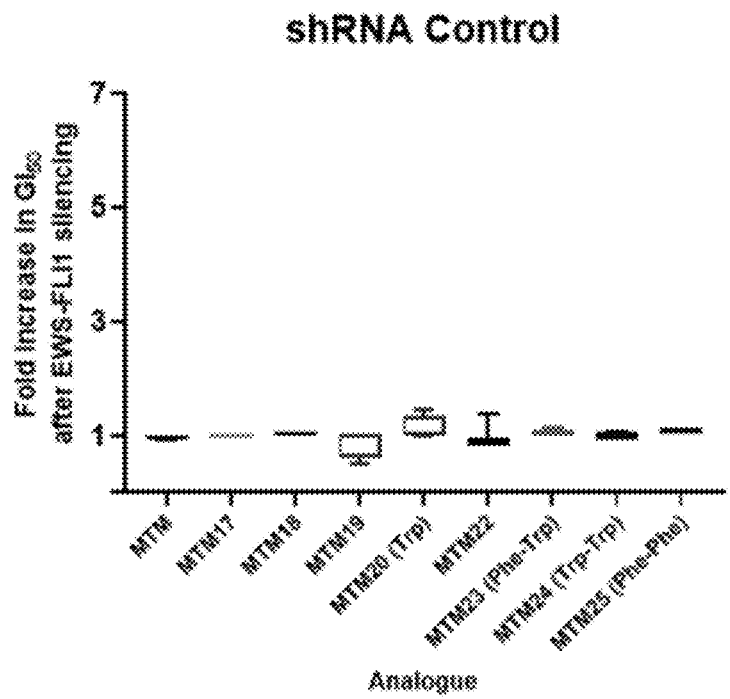
FIGS. 1A and 1B illustrate mechanistic assessment of target engagement using TC-32 cells with doxycycline inducible shRNA where GI50 ratio is silenced/unsilenced.

SEQ ID NO: 1 is an amino acid sequence for a DNA-binding domain (DBD) of target ETS transcription factor.

SEQ ID NO: 2 is another amino acid sequence for a DNA-binding domain (DBD) of target ETS transcription factor.

SEQ ID NO: 3 is an amino acid sequence of FLI1 transcription factor.

SEQ ID NO: 4 is an amino acid sequence of ERG transcription factor.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes MTM-OX and MTM-HY derivatives useful for treatment of cancer and other conditions, including diseases associated with an aberrant erythroblast transformation-specific transcription factor.

The MTM-OX and MTM-HY derivatives, which are sometimes referred to herein collectively as "MTM-OX" derivatives, of the subject technology can be synthesized according to the methods described herein in view of the knowledge of the skilled artisan.

Compounds as disclosed herein have the structure of formula I

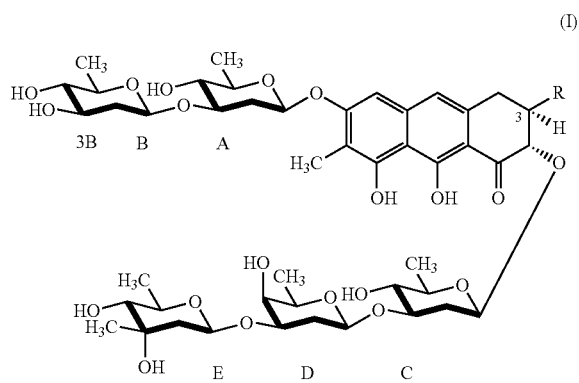

(I)

in which R is

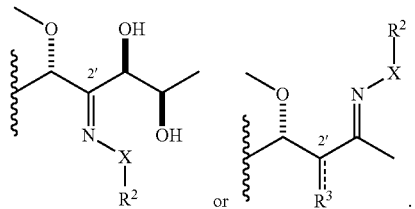

The structure of formula I is also represented herein as is also represented herein as: "MTM-R."

When R is

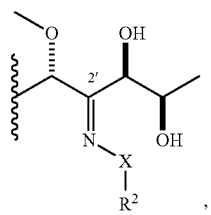

the compound is an oxime or a hydrazine of mithramycin A (MTM). The compound is an oxime when X is O, and the compound is a hydrazine when X is NH.

When R is

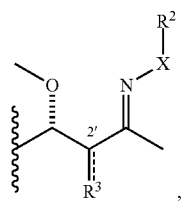

the compound is an oxime or a hydrazine of mithramycin short side chain ketone (MTM SK) or mithramycin short side chain diketone (MTM SDK). The compound is a derivative of MTM SK when $R^3$ is OH, and the compound is a derivative of MTM SDK when $R^3$ is O. The compound is an oxime when X is O, and the compound is a hydrazine when X is NH.

In some embodiments of the present disclosure, the compound has the structure of Formula I, wherein R is chosen from

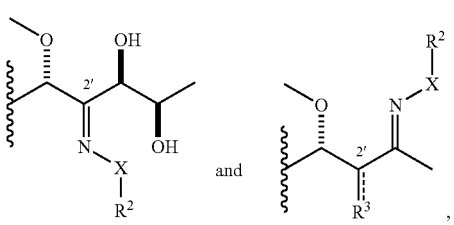

$R^3$ is chosen from O and OH, and X is chosen from O and NH. In some embodiments, $R^2$ is chosen from H, OH, alkyl, alkylaryl, aryl, acyl, alkene, alkylalkene, alkyne, alkylalkyne, acyl, acylaryl, amino acid, amino acid dipeptide, acyl-amino acid, and acyl-amino acid dipeptide. In some embodiments, R² comprises a quinolone, a benzothizole, a phenyl, a pyridine, or an indol group.

In some embodiments, R² comprises a quinolone group. In some embodiments, the quinolone is a substituted quinolone. In some embodiments, the quinolone is a substituted or unsubstituted isoquinoline. In some embodiments, the quinolone is an amino quinoline or amino isoquinoline, such as a 6-amino quinolone or a 6-amino isoquinoline.

In some embodiments, R² comprises a benzothizole group. In some embodiments, the benzothizole is a substituted benzothizole. In some embodiments, the benzothizole is a substituted or unsubstituted benzoimidazole. In some embodiments, the benzothizole is an amino benzothizole or an amino benzoimidazole. In some embodiments, the benzothizole is 6-amino benzothiazole, 5-amino benzothiazole, or 5-amino benzoimidazole.

In some embodiments, R² comprises a pyridine group. In some embodiments, the pyridine is a substituted pyridine. In some embodiments, the pyridine is an aminopyridine or a pyrimidin-amine, such as a pyrimidin-5-amine. In some embodiments, R² comprises a pyridine group and a phenyl group or an indol group.

In some embodiments, R² comprises an amino acid or derivative thereof, a substituted amino acid or derivative thereof, an amino acid dipeptide or derivative thereof, or a substituted amino acid dipeptide or derivative thereof. In this regard, in some embodiments, the group comprises one or two phenyl groups, one or two indol groups, or a phenyl group and an indol group. In some embodiments, the group comprises one or two amino acids or derivative thereof selected from alanine, phenylalanine, tyrosine, and tryptophan. In some embodiments, the amino acid is a derivative of alanine, such as, for example, alanine methyl ester. In some embodiments, the embodiments, the amino acid is a derivative of phenylalanine, tyrosine, and tryptophan and includes a phenyl or an indol group.

In some embodiments, R² comprises a phenyl or benzene group. In some embodiments, the phenyl is a substituted phenyl. In some embodiments, the group comprises a benzamide, benzoate, or benzamido group. In some embodiments, the group comprises a nitrobenzene, nitrobenzamide, aminobenzene, or methylbenzene. In some embodiments, the group comprises an ethyl-trifluoromethyl benzene. In some embodiments, the group comprises a methyl 4-(4-amino-3-isobutoxybenzamido)-3-isobutoxybenzoate, methyl 4-amino-3-isobutoxybenzoate, or ethyl-3-isobutoxy-4-nitrobenzamide. In some embodiments, the group comprises a phenylethanamine, phenylamine, or methyl 2-amino-3-phenylpropanoate. In some embodiments, the group comprises phenylalanine methyl ester, phenylalanine ethyl ester, or 5-amino-2-phenyl indol.

In some embodiments, R² comprises an indol group. In some embodiments, the indol is a substituted indol. In some embodiments, the group comprises 5-aminoindole, 6-amino methyl indol, 5-amino methyl indol, 5-amino-2-methyl indol, 6-amino indol, 4-amino indol, 7-amino indol, 5-amino-2-phenyl indol, or 5-aminoindolin-2-one. In some embodiments, the group comprises dimethyl hydroxylamide, propan-1-ol amide, pyrazin-2-ylmethanamine, amino ethyl indol, or amino ethyl indol-methyl-oxadazole. In some embodiments, the group comprises methyl 2-amino-3-(1H-indol-3-yl)propanoate, (2S)-(1r,4S)-4-methylcyclohexyl 2-amino-3-(1H-indol-3-yl)propanoate, or (S)-methyl 2-acetamido-3-(1H-indol-3-yl)propanoate. In some embodiments, the group comprises 3-(4-methoxybenzylidene)-5-aminoindolin-2-one or 3-(3-chloro-2-fluorobenzylidene)-5-aminoindolin-2-one. In some embodiments, the group comprises tryptophane methyl ester, tryptophane ethyl ester, 1-methyl-tryptophane, 1-methyl-tryptophane methyl ester, tryptophane methyl amide, tryptamine, tryptophane amide, tryptophane dimethyl amide, tryptophanol, or 5-amino-2-phenyl indol.

In some embodiments of the present disclosure, the compound has the structure of Formula I, wherein R is selected from the group consisting of:

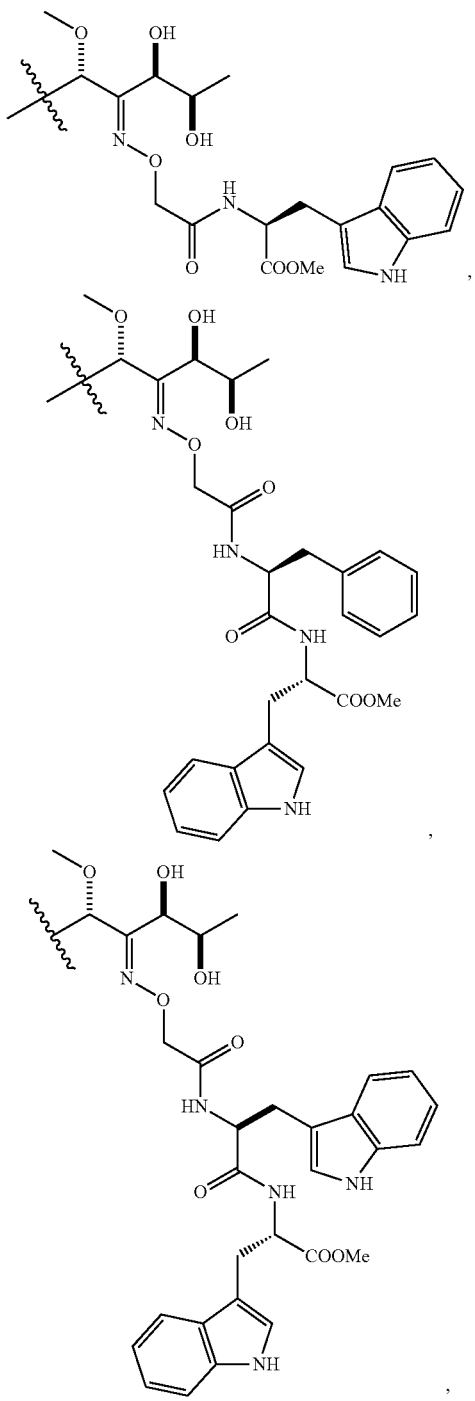

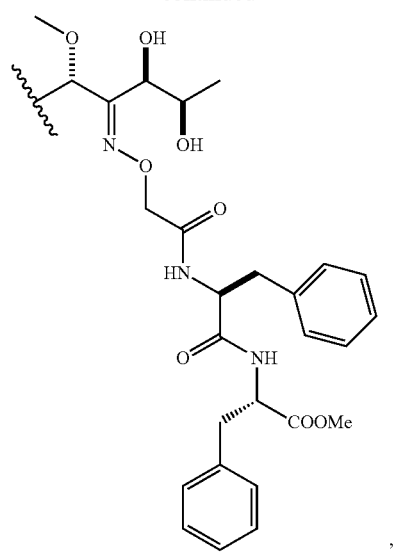
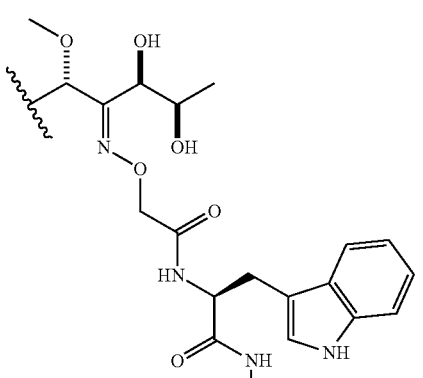
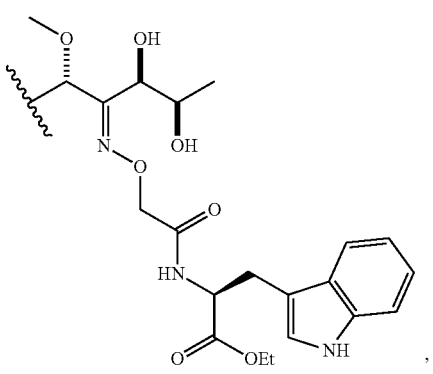
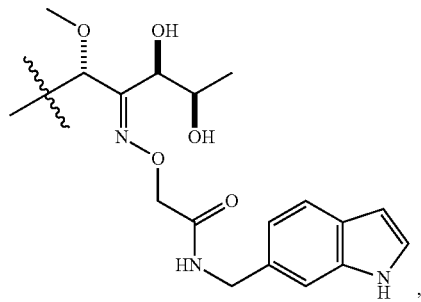
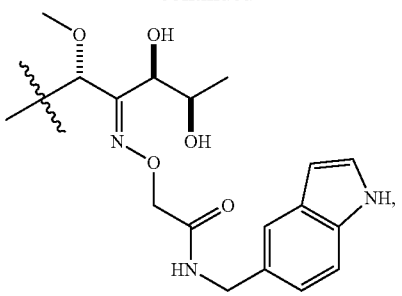
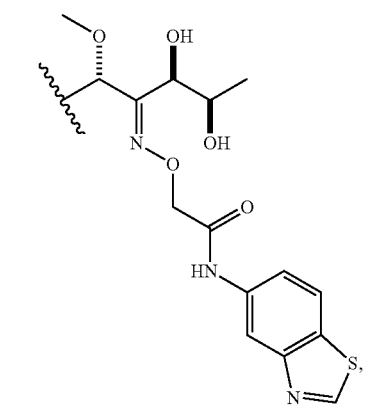
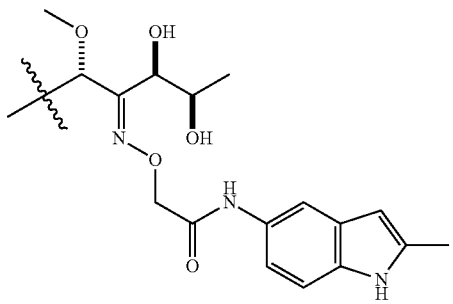
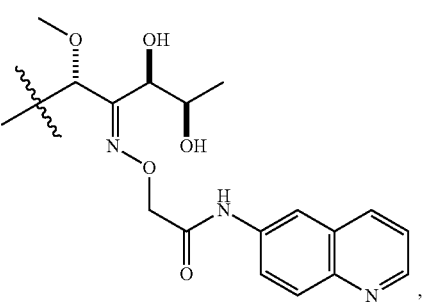
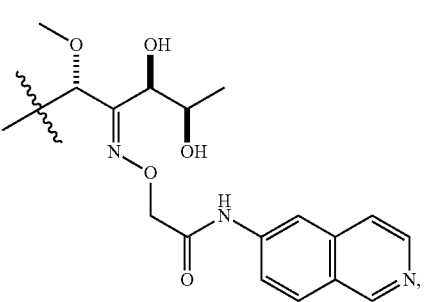

29
-continued
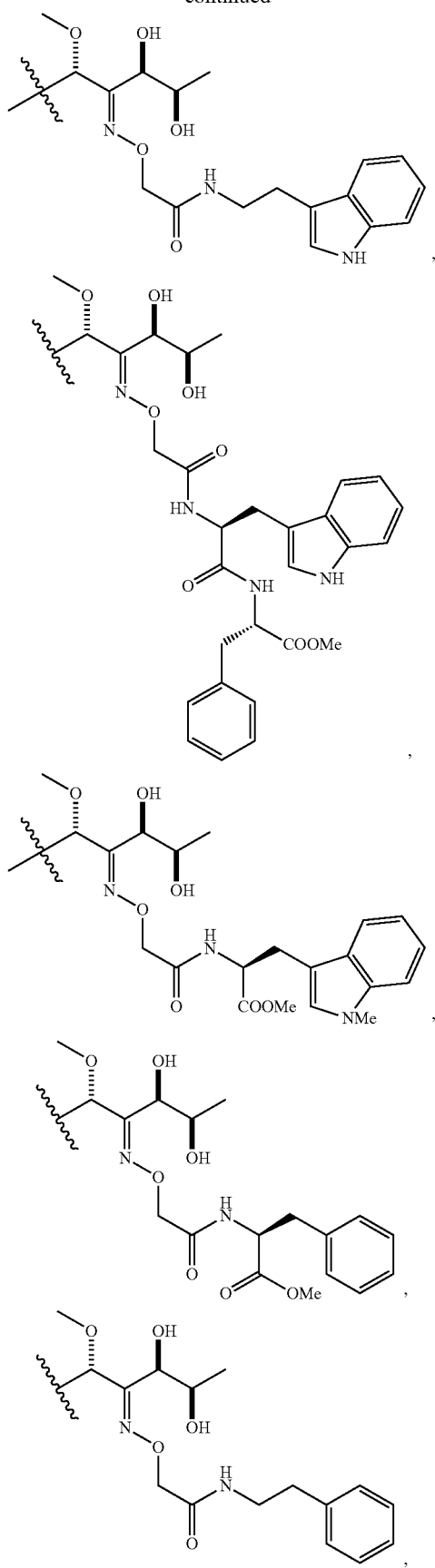
30
-continued
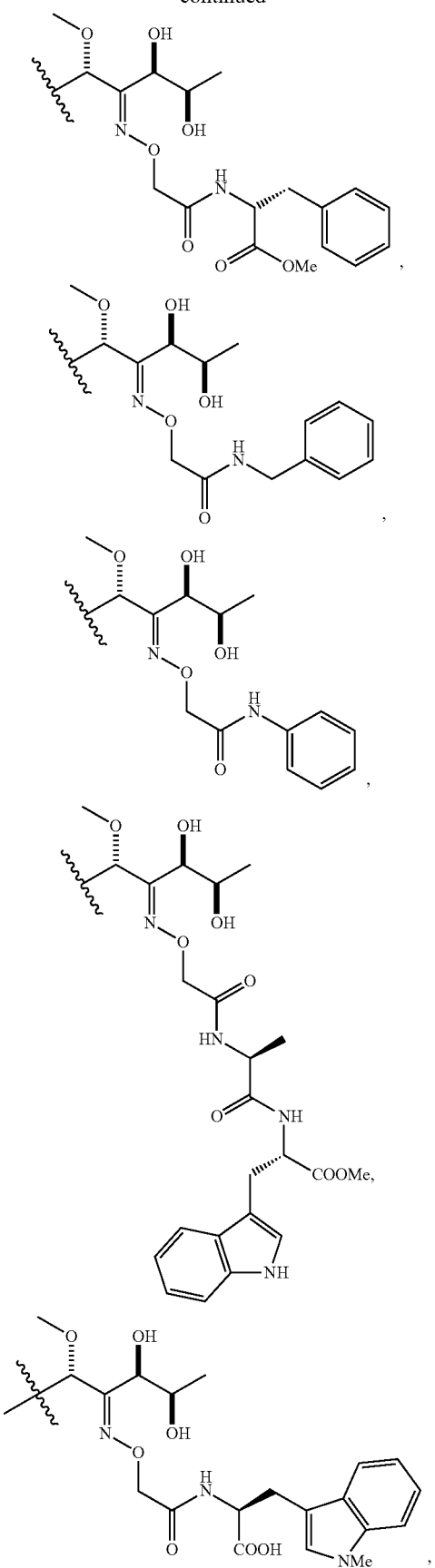

31
-continued
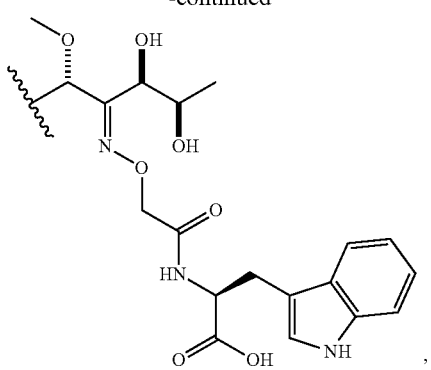
,
32
-continued
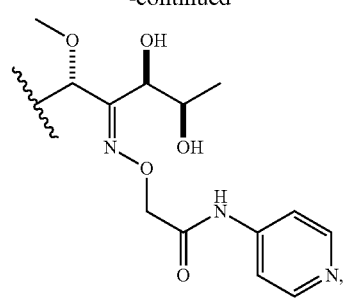
,
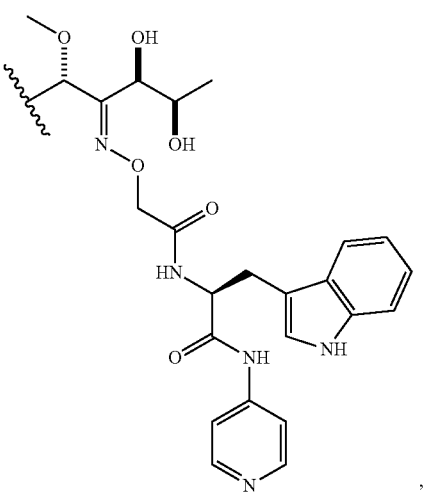
,
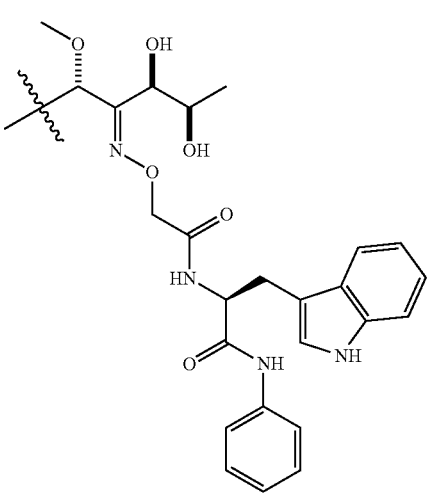
, 33
-continued
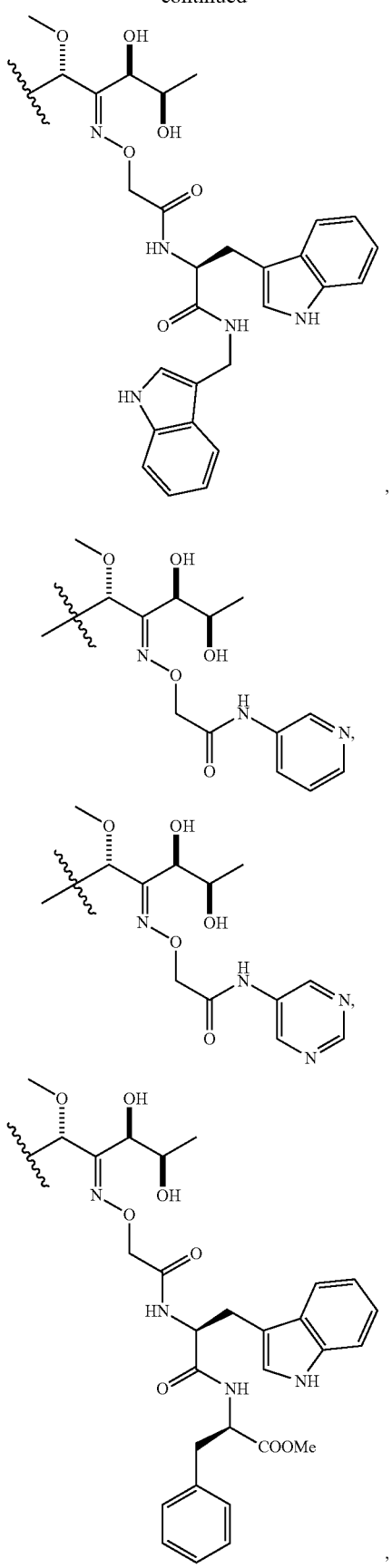
34
-continued
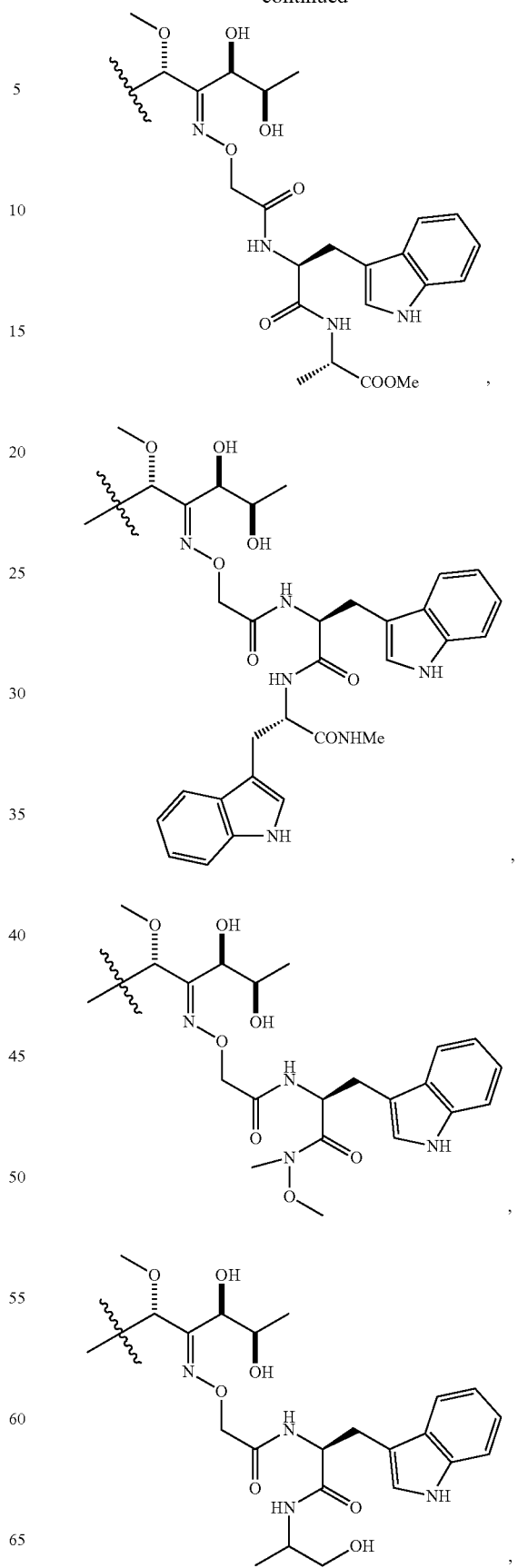

35
-continued
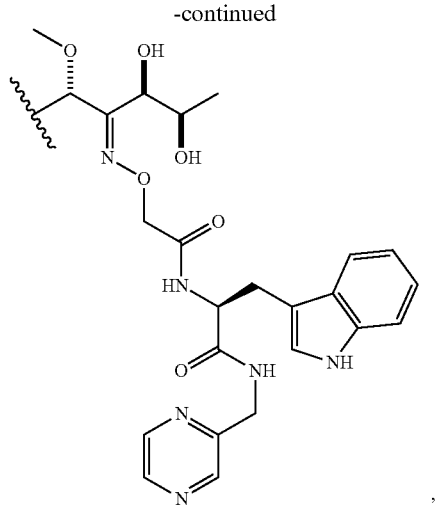
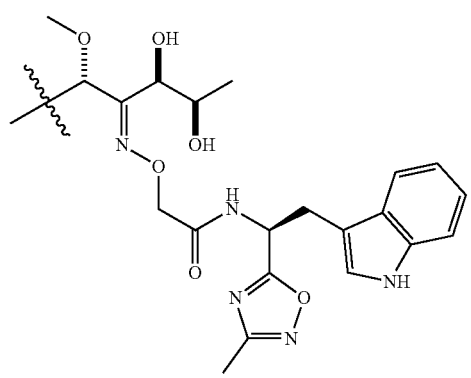
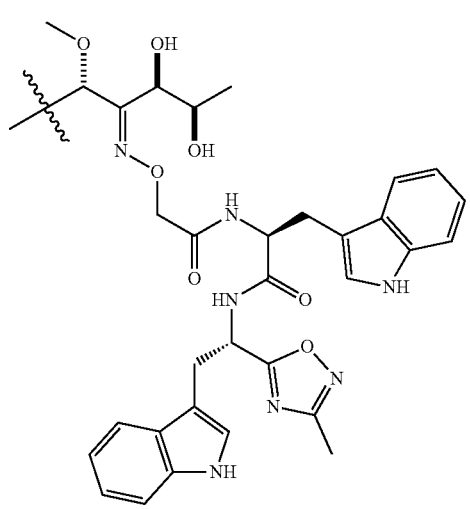
36
-continued
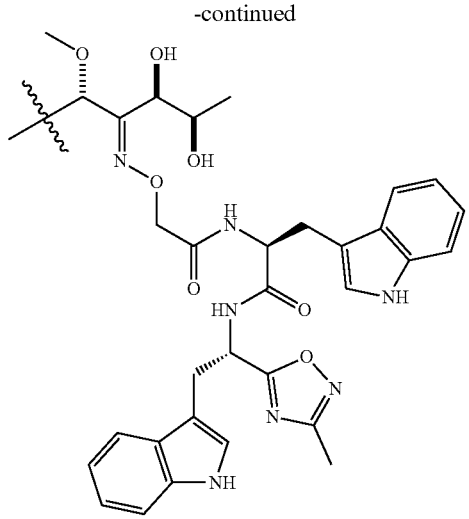
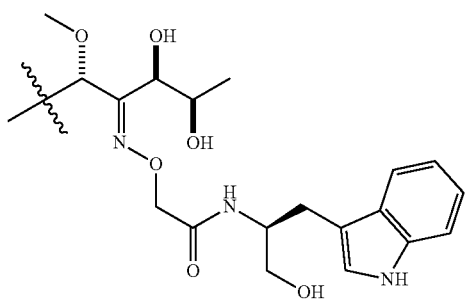
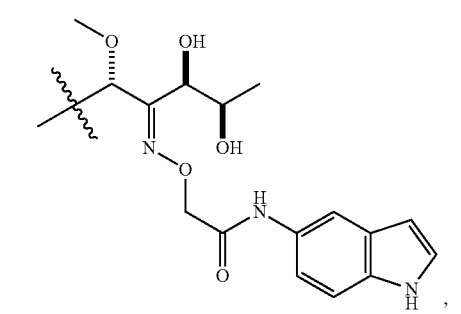
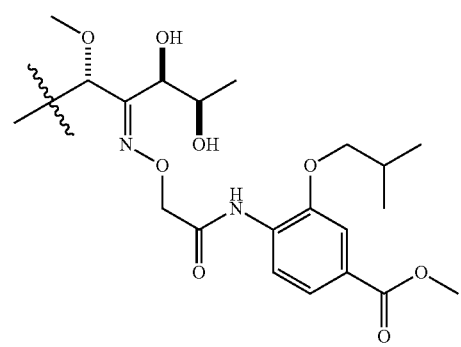

37
-continued
38
-continued
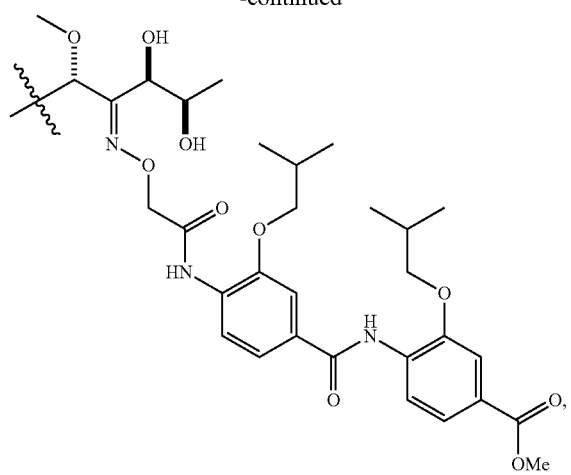
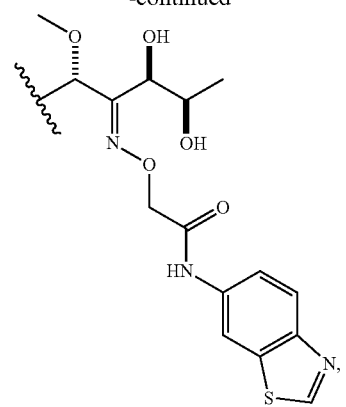
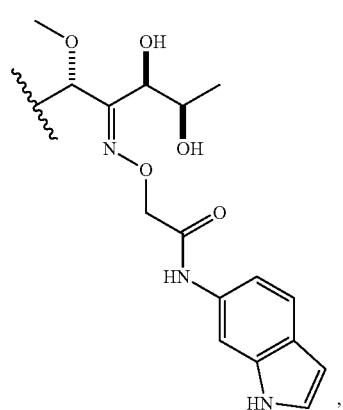
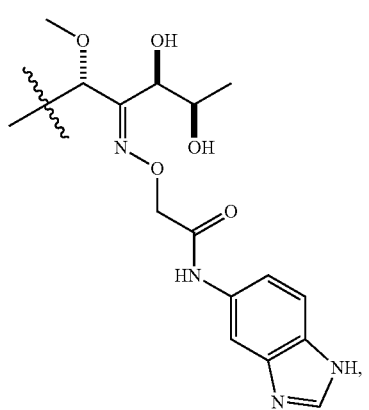
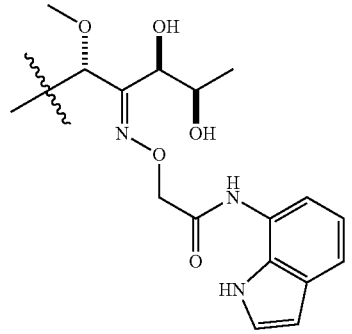
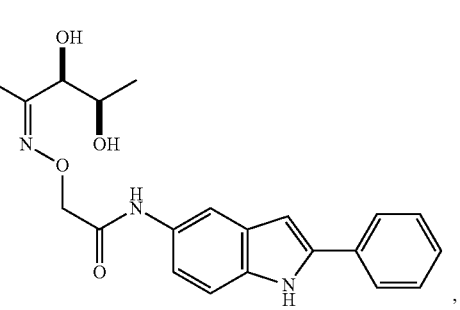

39
-continued
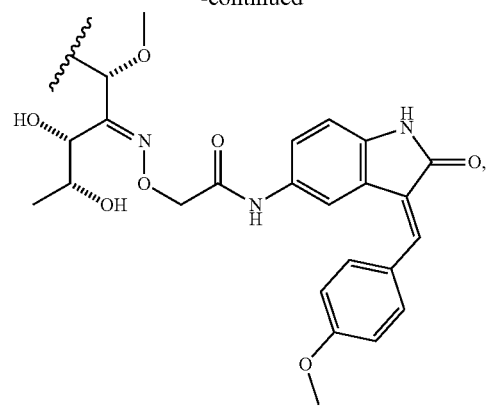
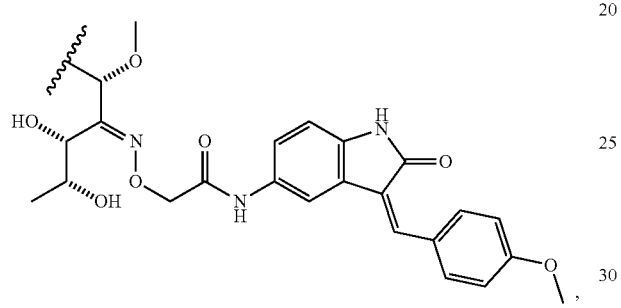
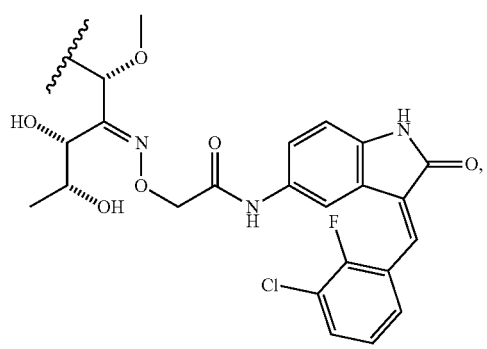
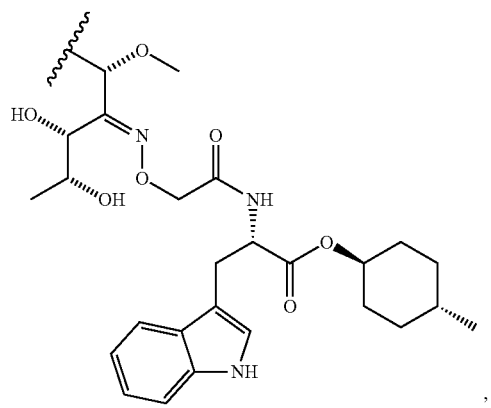
40
-continued
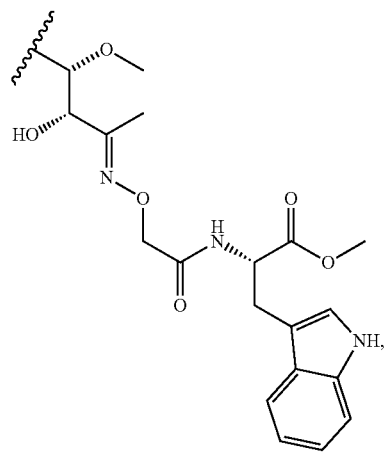
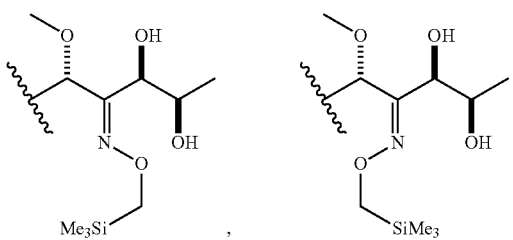
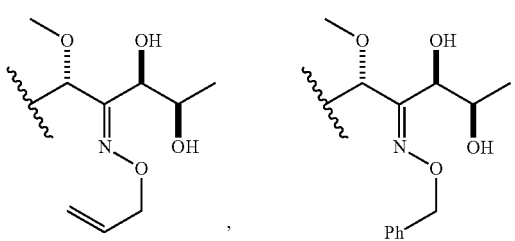
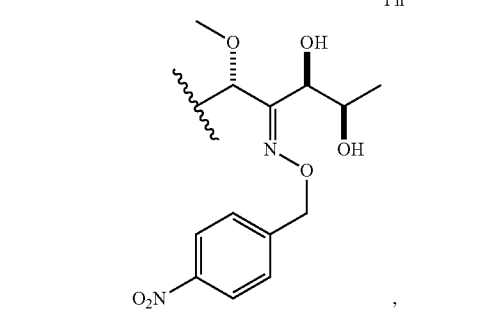
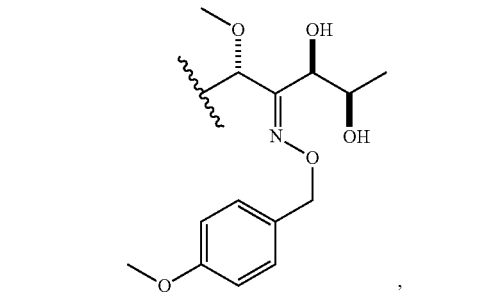

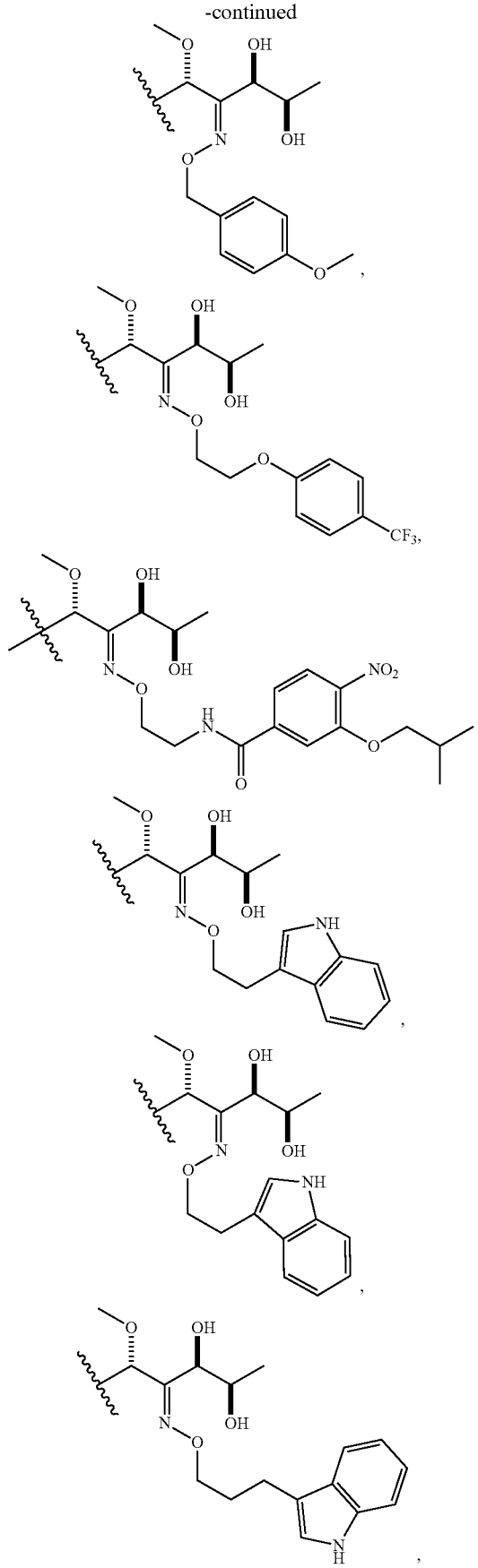
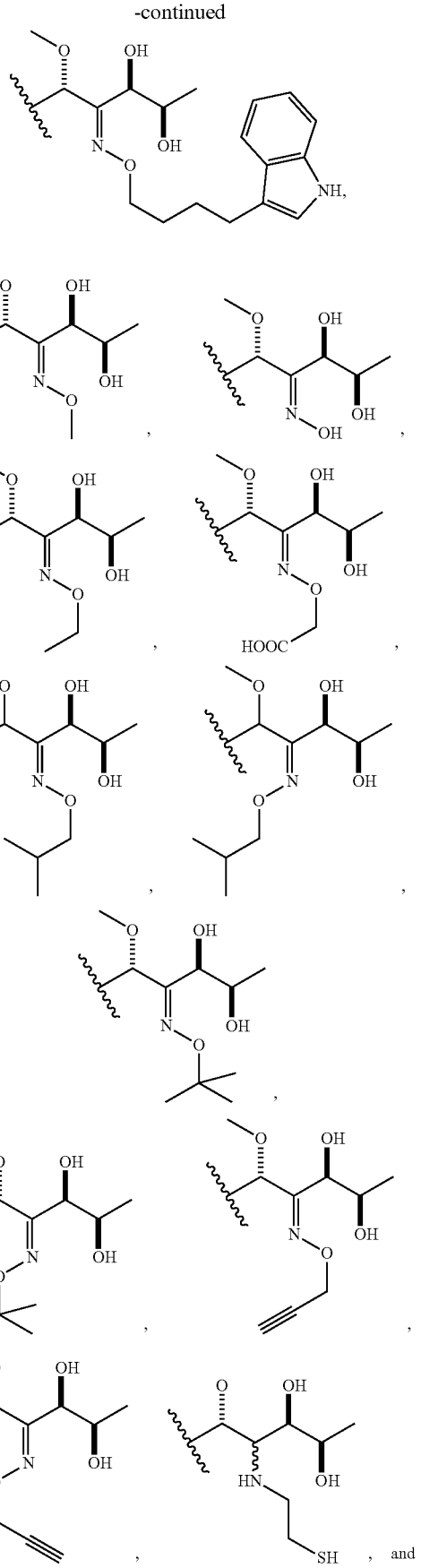

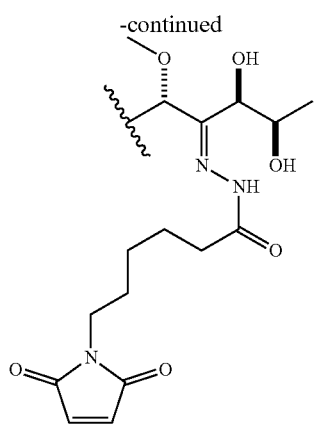

The compounds of the presently-disclosed subject matter can be used for the treatment of cancer, such as brain, colon, prostate, lung, breast, esophageal, pancreatic, skin, Ewing sarcoma, any type of blood cancer etc. MTM derivatives are also neuroprotective and can be used to treat various neuro-diseases, such as Huntington disease, etc.

Methods of Treatment

In one aspect, the subject technology provides a method for selectively modulating the activity of a target ETS transcription factor in a patient in need thereof, including administering to the patient a therapeutically effective amount of an MTM-OX or MTM-HY derivative or a pharmaceutically acceptable salt thereof, as described herein.

In an embodiment relating to this aspect, the subject technology provides a method for selectively modulating the activity of a target ETS transcription factor in a patient with Ewing sarcoma or prostate cancer for example. The method includes administering to the patient a therapeutically effective amount compound as disclosed herein. In some embodiments relating to this aspect, the ETS transcription factor includes a DNA binding domain with an amino acid sequence that is at least 85%, 90%, 95%, 98%, or 99% identical to SEQ ID NO: 1 or SEQ ID NO: 2 over the entire length of either of these sequences.

In another aspect, the subject technology provides a method of treating a target ETS transcription factor-mediated disease in a patient by administering to the patient a therapeutically effective amount of a compound as disclosed herein, wherein the compound specifically modulates the activity of the ETS transcription factor mediating the disease and wherein the target ETS-mediated disease is Ewing sarcoma, clear-cell sarcoma, myxoid liposarcoma, desmoplastic small round cell tumor, myxoid chondrosarcoma, acute myeloid leukemia, congenital fibrosarcoma, prostate cancer or pancreatic cancer, for example. The following Table lists several ETS transcription factors that may be modulated and associated diseases that may be treated with the subject technology.

| ETS Transcription factors and associated diseases. | |
|---|---|
| Transcription factor | Disease |
| ETS-1 | Meningioma, invasive carcinoma of the breast, colorectal carcinoma, pancreatic carcinoma, adenocarcinoma, thyroid carcinoma, thymoma, angioma |
| ETS-2 | Breast cancer |
| ERG | TMPRSS2:ERG fusion in prostate cancer EWS-ERG fusion in Ewing Sarcoma ERG overexpression in AML |
| FLI1 | EWS-FLI1 fusion in Ewing Sarcoma. |
| PEA3 | Invasive breast carcinoma |
| ER81 | EWS-ER81 fusion in Ewing sarcoma; prostate carcinoma, breast carcinoma |
| ELF-1 | Prostate, ovarian and breast cancers, leukemia and lymphoma. |
| TEL/ETV6 | TEL fusion protein partners (PDGFbetaR, TRKc, ABL, and JAK2) in leukemia and fibrosarcoma |
| PU.1/SPI1 | Promyelocytic leukemia, acute myelocytic leukemia |
| Myc | Burkitt lymphoma, B-cell lymphoma, multiple myeloma, medulloblastoma, neuroblastoma, colorectal, ovarian, and intestinal cancer |

In general, the compound as disclosed herein can be used for the treatment of a target ETS transcription factor-mediated disease including Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblastic leukemia (ALL), Alzheimer's disease (AD), or Down syndrome (DS) or other hyperproliferative disease in which an aberrant activity of a target ETS transcription factor is implicated. A "hyperproliferative disease" includes diseases and conditions that are associated with any sort of abnormal cell growth or abnormal growth regulation, specifically a cancer.

Some of the compounds disclosed herein are more specific than MTM for complexing with a target EST transcription factor and, therefore, inhibiting its activity. The specific or selective the compounds of the subject technology are useful for treating diseases that are mediated by, for example, FLI1 or ERG, such as Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblastic leukemia (ALL), Alzheimer's disease (AD), or Down syndrome (DS) or other hyperproliferative disease in which an aberrant activity of a target ETS transcription factor is implicated.

Other hyperproliferative diseases which may be benefited by the methods and compounds of the subject technology include, though it is not limited to, neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In another aspect of the present disclosure, an effective amount of the compounds as disclosed herein or a pharmaceutically acceptable salt thereof is administered to a patient in need of cancer treatment or a neuro-disease, such as Huntington's disease. The compounds or pharmaceutically acceptable salts thereof of the present disclosure can be administered to a patient, e.g., a human patient, in need of such treatment by any route. The compounds or pharmaceutically acceptable salts thereof of the present disclosure can be administered alone or with a pharmaceutically acceptable carrier or excipient.

Dosage Form and Formulation

A compound as described herein can be administered to a patient in any possible dosage form including, but not limited to ingestible tablets, buccal tablets, troches, capsules, elixirs, suspensions, syrups, wafers, infusion, aqueous liquid and the like. Solutions of the compounds can be prepared in water and mixed with suitable excipients. Under ordinary conditions of storage and use, these preparations can contain a preservative to prevent the growth of microorganisms or retain stabilization of the compound. The pharmaceutical forms suitable for injection include sterile aqueous solutions or dispersions and sterile powders for the extemporaneous preparation of sterile injectable solutions or dispersions. The form should be sterile and should be fluid to the extent it makes injection possible.

A composition containing a compound as disclosed herein can be prepared by known methods, such that an effective quantity of the therapeutic agent is delivered to a subject. Suitable vehicles for such a composition are described, for example, in Remington's Pharmaceutical Sciences (2003) and in the Handbook of Pharmaceutical Additives (compiled by Michael and Irene Ash, Gower Publishing Limited, Aldershot, England (1995)).

In some embodiments, the composition of this disclosure enables sustained, continuous delivery of a compound as disclosed herein to tissues adjacent to or distant from an administration site. The biologically-active agent is capable of providing a local or systemic biological, physiological or therapeutic effect. For example, the compound may act to kill cancer cells or cancer stem cells or to control or suppress tumor growth or metastasis, among other functions.

In some embodiments, the formulations of the present disclosure are administered in an amount effective to provide the desired level of biological, physiological, pharmacological and/or therapeutic effect such as inhibition of a target ETS transcription factor.

The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical formulations include, for example, at least about 0.1% of an active compound, such as a compound as disclosed herein or pharmaceutically acceptable salt thereof. In other embodiments, the active compound may comprise between about 1% to about 75% of the weight of the unit dosage, or between about 5% to about 50% by weight of the unit dosage, for example, and any specific percentage in between these ranges. In other non-limiting examples, a dose may also comprise from about 0.01 microgram/kg/body weight, about 50 microgram/kg/body weight, about 100 microgram/kg/body weight, about 500 microgram/kg/body weight, about 1 milligram/kg/body weight, about 5 milligram/kg/body weight, about 10 milligram/kg/body weight, about 30 milligram/kg/body weight, about 40 milligram/kg/body weight, about 50 milligram/kg/body weight, about 100 milligram/kg/body weight, or more per administration, and any range or specific amount derivable therein. In non-limiting examples of a derivable range from the numbers listed herein, a range of about 5 microgram/kg/body weight to about 5 milligram/kg/body weight, about 50 microgram/kg/ body weight to about 50 milligram/kg/body weight, etc., can be administered.

For a safe and effective dosage, the formulations can be administered at a compound dose of about 0.01 to about 500 mg/m² (body surface)/day, about 0.01 to about 300 mg/m²/day, 0.01 to about 200 mg/m²/day, about 1 to about 200 mg/m²/day about 10 to about 100 mg/m²/day, about 25 to about 100 mg/m²/day or any range derivable therein to a subject such as a human. In certain aspects, the composition may be administered at a dose of about 0.01 to about 200 mg/kg body weight, about 0.01 to about 100 mg/kg body weight, 1 to about 50 mg/kg body weight, about 1 to about 20 mg/kg body weight, about 3 to about 10 mg/kg body weight, about 3 to about 6 mg/kg body weight or any range derivable therein to a subject such as a human. In some embodiments, a formulation of the subject technology may be administered in a dose of 1, 2, 3, 4, 5, 6, 7, 8, 9, 10, 15, 20, 25, 30, 40, 50, 60, 70, 80, 90, 100 mg or more per day. Each liquid dose may be in a volume of 1, 10, 50, 100, 200, 500, 1000 or more μl or ml.

In some embodiments, the pharmaceutical formulation of the subject technology includes an MTM-OX or MTM-HY derivative compound as disclosed herein in an amount effective to result in a serum concentration of the compound in the mammal in a range of from 1 nM to 1 mM, particularly 1 nM to 2 μM.

Serum and systemic circulation concentrations of the compound effective to result in the treatment of a target ETS transcription factor-mediated disease may vary depending on a number of factors. Influential variables can include, for example, pKa, solubility or molecular weight of the compound. These properties of a particular MTM-OX or MTM-HY derivative may affect how a patient metabolizes the compound, how much of the compound enters and remains in the systemic circulation of the patient, and how effectively the compound treats, prevents or causes regression of the disease, e.g., Ewing sarcoma, tumor or cancer.

Precise amounts of the therapeutic composition also depend on the judgment of the practitioner and are peculiar to each individual. Factors affecting the dose include the physical and clinical state of the patient, the route of administration, the intended goal of treatment (e.g. alleviation of symptoms versus cure) and the potency, stability and toxicity of the particular therapeutic substance.

Route of Administration

In accordance with the methods of the disclosure, the described composition or formulation of the subject technology may be administered to a subject in a variety of forms depending on the selected route of administration, as will be understood by those skilled in the art. It may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, intratumoral, transepithelial, nasal, intrapulmonary, intrathecal, rectal and topical modes of administration. Parenteral administration may be by continuous infusion over a selected period of time.

Combination Therapies

In certain embodiments, the compounds, compositions or formulations of the subject technology are administered with a second or additional active agent(s) such as with one or more different MTM-OX or MTM-HY derivatives or another anticancer agent. Such therapy can be applied in the treatment of any disease for which treatment with an MTM-OX or MTM-HY derivative is contemplated. For example, the disease may be a hyperproliferative disease, such as Ewing sarcoma or prostate cancer.

In certain embodiments, the additional active agent may be a chemotherapeutic agent or a radiation therapy. Examples of chemotherapeutic agents include, but are not limited to, cetuximab (erbitux), herceptin (trastuzumab), fludarabine, cyclophosphamide, rituximab, imatinib, Dasatinib (BMS0354825), cisplatin (CDDP), carboplatin, procarbazine, mechlorethamine, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabien, navelbine, farnesyl-protein tansferase inhibitors, transplatinum, 5-fluorouracil, vincristin, vinblastin, methotrexate, an analogue or derivative thereof. In certain embodiments, the active or anticancer agent(s) that may be used in combination with an MTM-OX or MTM-HY derivative may be fludarabine, cyclophosphamide, rituximab, imatinib or Dasatinib. In a certain aspect, the cancer may be resistant to a particular chemotherapeutic agent, such as fludarabine, cyclophosphamide, rituximab, imatinib or Dasatinib.

To facilitate an understanding of the present subject technology, a number of terms and phrases are defined below:

A reference to an element in the singular is not intended to mean "one and only one" unless specifically stated, but rather "one or more."

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, aryl, substituted aryl, alkoxyl, hydroxyl, aryloxyl, alkoxyl, alkylthio, arylthio, aralkyloxyl, aralkylthio, carboxyl, alkoxycarbonyl, oxo, cycloalkyl, nitro, amino, alkylamino, dialkylamino, sulfate, mercapto, and trimethylsilyl. Thus, as used herein, the term "substituted alkyl" includes alkyl groups, as defined herein, in which one or more atoms or functional groups of the alkyl group are replaced with another atom or functional group.

Further, as used herein, the terms alkyl and/or "substituted alkyl" include an "allyl" or an "allylic group." The terms "allylic group" or "allyl" refer to the group —$CH_2HC\!\!=\!\!CH_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine, benzophenone, furan, thiophene, pyrrole, pyran, pyridine, imidazole, benzimidazole, benzothiazole, isothiazole, isoxazole, pyrazole, pyrazine, triazine, pyrimidine, quinoline, isoquinoline, indole, carbazole, and the like. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, $CF_3$, and —NR'R", wherein R' and R" can each be independently hydrogen, alkyl, substituted alkyl, aryl, substituted aryl, and aralkyl. Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Alkene" or "Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH=CH—CH=CH—; —CH=CH—$CH_2$—; —($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—$CH_2$—O—); and ethylenedioxyl (—O—($CH_2$)$_2$—O—). An alkylene group can have about 2 to about 3 carbon atoms and can further have 6-20 carbons.

"Alkyne" refers to a functional group consisting of two carbon atoms bonded by a triple bond (—C≡C—). An alkyne compound would have the formula R—C≡C—R, where R is a hydrogen atom or an alkyl group. A terminal alkyne compound would have the formula R—C≡C—H, where R is an alkyl group. A cyclic alkyne compound would have the alkyne functionality in a cyclic structure. Examples include, but are not limited to ethyne or acetylene and propyne.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl. The acyl group can be optionally substituted (a "substituted acyl") with one or more acyl group substituents, which can be the same or different, wherein "acyl group substituent" includes aryl, amino acid, amino acid dipeptide, As used herein, the term "amino acid" refers to a functional group or component thereof that is derived from an amino acid molecule, such as, for example, tryptophan, phenylalanine, alanine, or tyrosine. The term "amino acid dipeptide" refers to a functional group or component thereof that is derived from a peptide including two amino acid molecules, such as, for example, phenylalanine-tryptophan or tryptophan-tryptophan. An amino acid group or amino acid dipeptide group can be optionally substituted. In some embodiments, an amino acid group or amino acid dipeptide group can be derived from an amino acid molecule, such as, for example, tryptamine (Tra), methyl tryptophan, or tryptophan methyl ester derived from tryptophan, As used herein, a "target ETS transcription factor" refers to a transcription factor, which comprises a DNA-binding domain (DBD) having an amino acid sequence that is at least 85%, 90%, 95%, 98%, or 99% identical to SEQ ID NO: 1 or SEQ ID NO: 2 over the entire length of either of these sequences. SEQ ID NO: 1 and SEQ ID NO: 2 are set forth in an Appendix submitted herewith and incorporated herein by reference.

As used herein the term "modulator," "modulating," or "modulate" in connection with the target ETS transcription factor of the subject technology refers to any agent that has a functional effect on the transcription factor, including positively or negatively affecting its binding to a DNA substrate, positively or negatively affecting the formation and/or stability of a complex formed between the transcription factor and its oligonucleotide substrate, positively or negatively affecting its function in causing the transcription of its oligonucleotide substrate.

As used herein, the term "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "variant" in relation to the amino acid sequence of the ETS transcription factors refers to a naturally occurring allelic variant of the ETS transcription factors such as those shown in SEQ ID NO: 3 and SEQ ID NO: 4, which includes any substitution of, variation of, modification of, replacement of, deletion of or addition of one (or more) amino acids provided the resultant ETS transcription factor has a transcription factor activity and has a DNA binding domain that is at least 85%, 90%, 95%, 98%, or 99% identical to SEQ ID NO: 1 or SEQ ID NO: 2 over the entire length of either of these sequences. For example, a variant of ETS transcription factor may have at least 50%, or at least 60%, or at least 70% sequence identity with the ETS transcription factors such as those shown in SEQ ID NO: 3 and SEQ ID NO: 4 over the entire length of the sequence, provided that the variant has a transcription factor activity and has a DNA binding domain that is at least 85%, at least 90%, at least 95% or at least 98% identical to SEQ ID NO: 1 or SEQ ID NO: 2 over the entire length of either of these sequences.

The terms "percentage of sequence identity" or "percentage homology" and any equivalent terms are used interchangeably herein to refer to comparisons among polynucleotides and polypeptides, and are determined by comparing two optimally aligned sequences over a comparison window, wherein the portion of the oligonucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB [Pearson and Lipman, (1988), Proc. Natl. Acad. Sci. USA 85(8): 2444-2448; Altschul et al., (1990), J. Mol. Biol. 215(3):403-410; Thompson et al. (1994), Nucleic Acids. Res. 22(2): 4673-4680; Higgins et al., (1996), Meth. Enzymol. 266:383-402; Altschul et al., (1993), Nature Genetics 3:266-272; Brutlag et al. (1990) Comp. App. Biosci. 6:237-24], the disclosures of which are incorporated by reference in their entireties. In an embodiment, protein and nucleic acid sequence identities are evaluated using the Basic Local Alignment Search Tool ("BLAST") which is well known in the art [e.g., Karlin and Altschul, (1990), Proc. Natl. Acad. Sci. USA 87:2267-2268; Altschul et al., (1997), Nuc. Acids Res. 25:3389-3402] the disclosures of which are incorporated by reference in their entireties.

As used herein, an "oligonucleotide substrate" in reference to a substrate of a target ETS transcription factor refers to an oligonucleotide which comprises a target ETS transcription factor binding site. An oligonucleotide substrate can be single-stranded, double-stranded, or a hairpin. Preferably, an oligonucleotide substrate is double stranded. An oligonucleotide substrate can be DNA, RNA or a chimeric (comprising both deoxy and ribose nucleotides) or comprise one or more oligonucleotide modifications described herein.

As used herein, the term "transcription factor binding site" refers to a nucleic acid sequence that is recognized and bound by a transcription factor and mediates the transactivation of a reporter gene in response to that binding. Without limitations, a transcription binding site can be from any of various species including human, mouse, rat, guinea pig and the like. In some embodiments, the transcription factor binding site is a target ETS binding site such as a FLI1 binding site or an ERG binding site.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

General Procedure for the Synthesis of MTM/MTM SK Oxime or MTM/MTM SK Hydrazine Conjugates.

The biosynthesis of MTM can be accomplished through a genetically engineered S. argillaceus strain, M7W1, which contains an inactivated mtmW gene coding for the MtmW enzyme. To a stirred solution of MTM/MTM SK (15 mg, 0.014 mmol) in 1.0 mL dry MeOH was added 0.03 mmol 0-substituted hydroxylamine (or N-substituted hydrazine) and 10 uL TFA at rt, and the mixture was stirred in dark overnight. The reaction was monitored by using HPLC-MS. Desired products were purified using preparative HPLC and dried via lyophilization to give the desired MTMox or MTMhy product.

General synthesis of MTM-OX/HY and MTM-SK-OX/HY compounds is presented in the following Scheme:

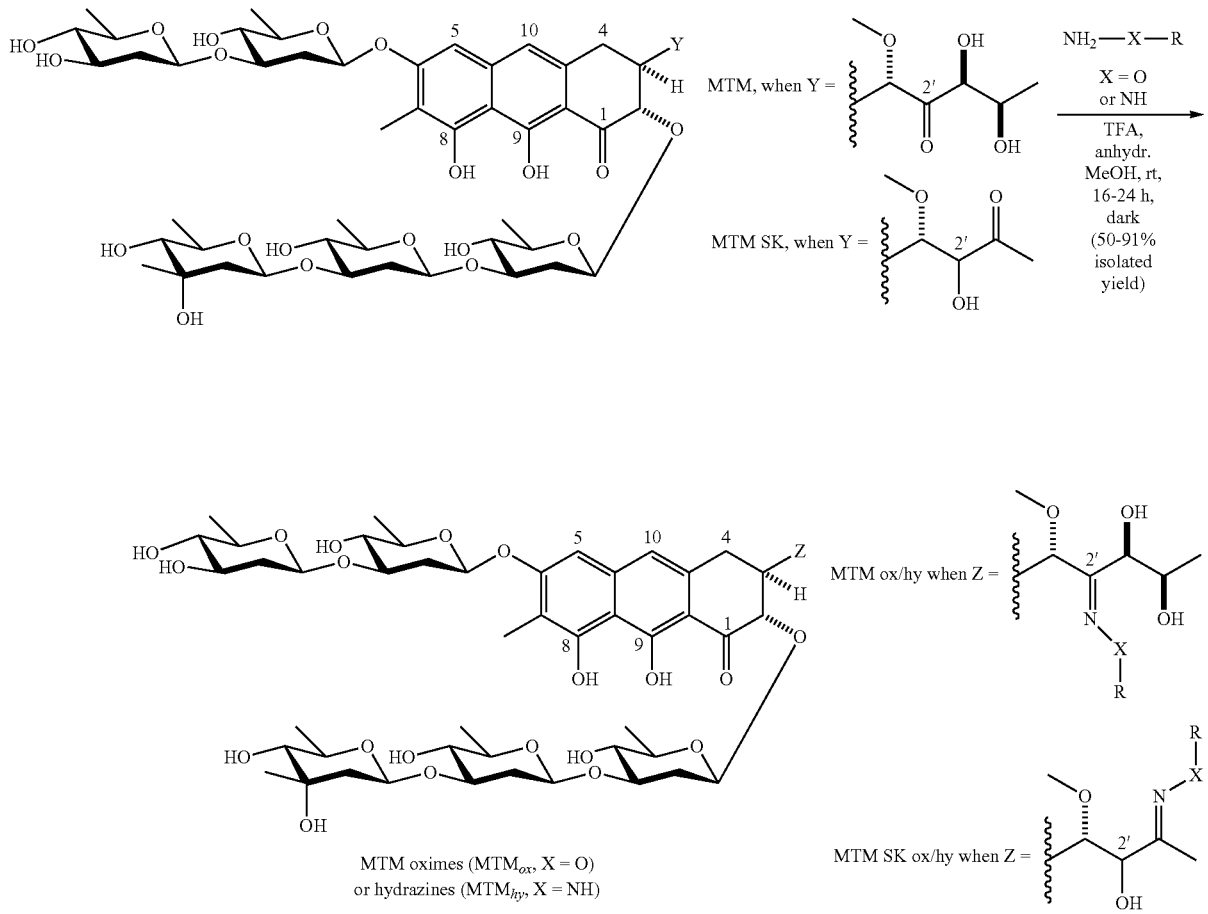

General Procedure for the reductive amination. To a solution of MTM A (15 mg, 0,014 mmol) in MeOH was added substituted amine hydrochloride (0.14 mmol), the resulting mixture was stirred at in dark overnight. Sodium cyanoborohydride (0.3 mmol) was added and continued to stir overnight. Reaction progress was monitored by HPLC-MS) and the final desired product purified via preparative HPLC and dried via lyophilization.

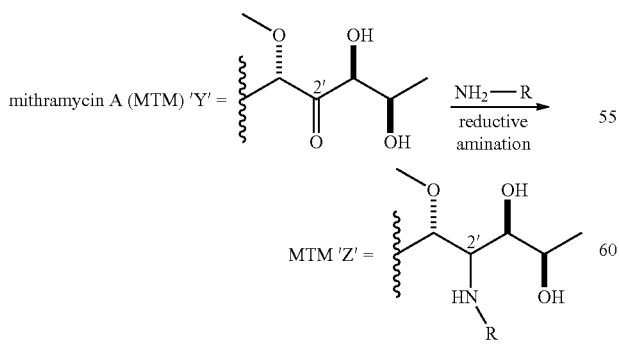

Exemplary compounds of the presently-disclosed subject matter were produced as follows:

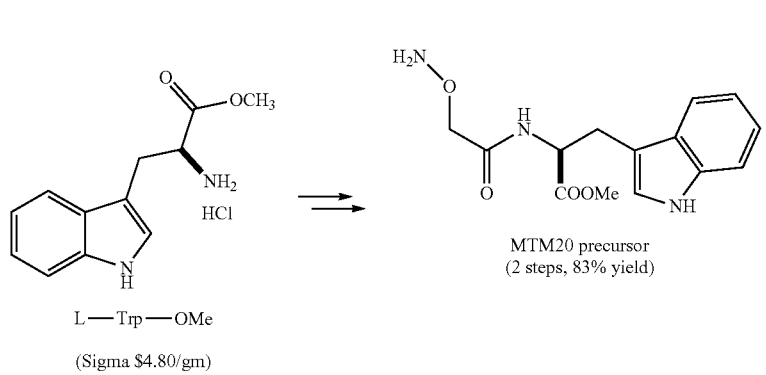
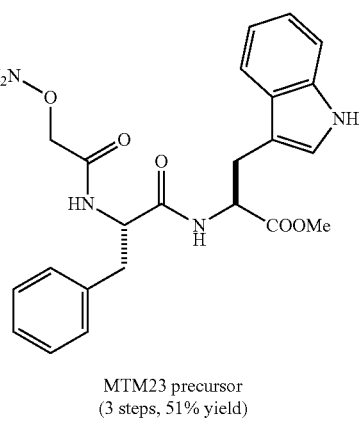
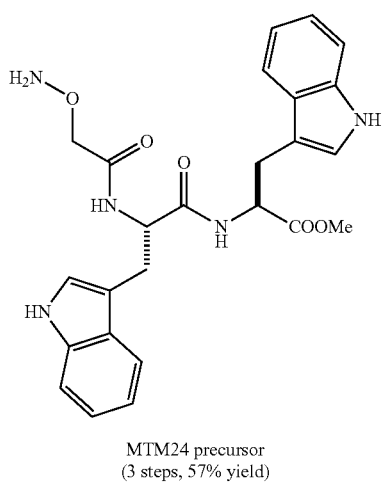
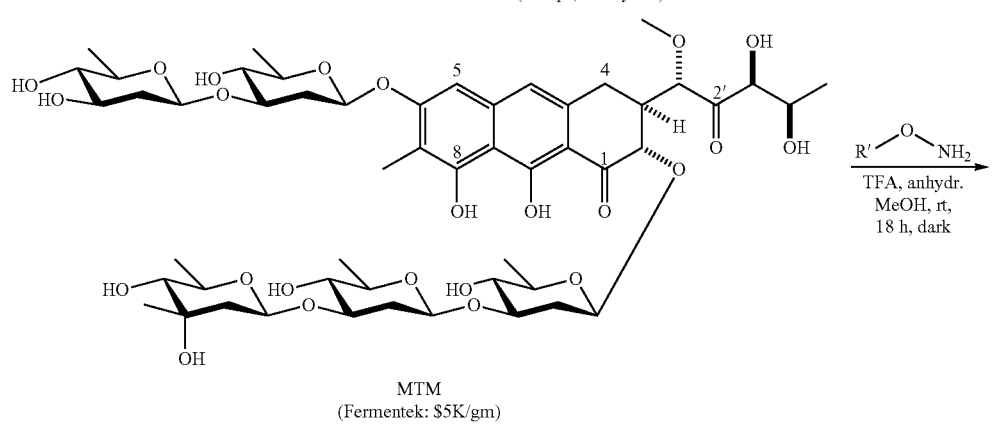
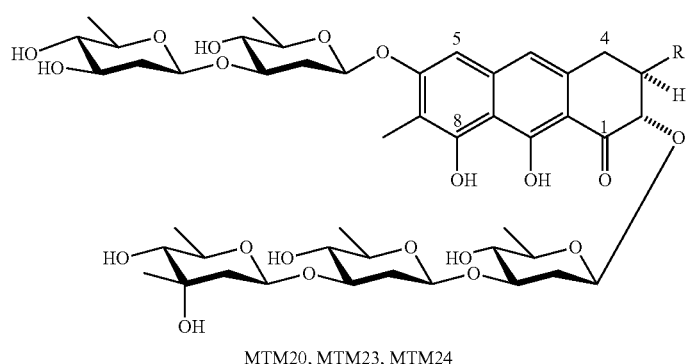

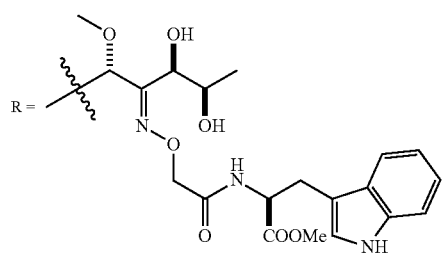

MTM20
conversion: 90-100%
isolated yield: 91%

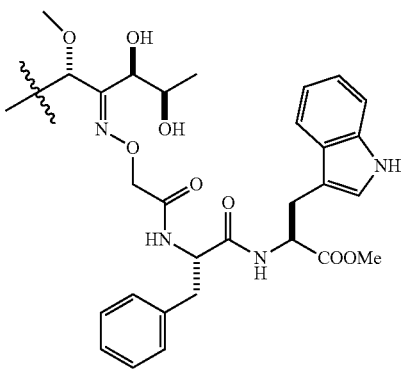

MTM23
conversion 90-100%
isolated yield: 85%

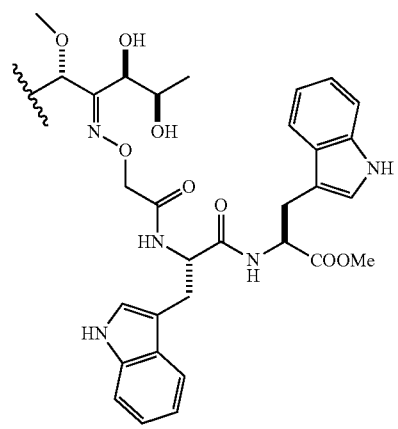

MTM24
conversion 90-100%
isolated yield: 83%

NMR data for Exemplary Compounds is as follows.

MTM20. (13 mg, 91%) was prepared as a yellow solid from MTM A (18 mg, 0.016 mmol) using methyl (2-(aminooxy) acetyl)-L-tryptophanate (12 mg, 0.045 mmol), MeOH (450 uL), TFA (5 uL) following general procedure. $^1$H NMR (400 MHz, Methanol-d4) δ 7.44 (d, J=8.0 Hz, 1H), 7.29 (d, J=8.2 Hz, 1H), 7.09 (s, 1H), 7.04 (t, J=7.9 Hz, 1H), 6.94 (s, 1H), 6.91 (t, J=13.5, 6.0 Hz, 1H), 6.64 (s, 1H), 5.14 (d, J=8.8 Hz, 1H), 5.08 (d, J=9.6 Hz, 1H), 4.96 (dd, J=9.6 Hz, J=0.9 Hz 1H), 4.76-4.69 (m, 2H), 4.69-4.50 (m, 5H), 4.26-4.13 (m, 2H), 3.90-3.82 (m, 1H), 3.78-3.60 (m, 5H), 3.60-3.42 (m, 5H), 3.41-3.35 (m, 5H), 3.19-3.27 (m, 2H), 3.17-2.87 (m, 6H), 2.69-2.51 (m, 2H), 2.47-2.34 (m, 1H), 2.22-2.10 (m, 4H), 2.00-1.69 (m, 4H), 1.66-1.50 (m, 3H), 1.36-1.27 (m, 12H), 1.28-1.22 (m, 7H), 1.12 (d, J=6.0 Hz, 3H). $^{13}$C NMR (101 MHz, Methanol-d4) δ 203.2, 172.0, 170.9, 163.7, 161.0, 159.0, 155.3, 138.4, 136.5, 136.3, 127.2, 123.1, 121.0, 118.4, 117.7, 116.8, 110.9, 110.5, 108.8, 108.0, 107.4, 100.7, 100.5, 98.5, 98.4, 97.4, 96.4, 79.5, 79.3, 77.3, 77.0, 76.7, 76.4, 75.9, 75.1, 74.7, 73.3, 72.3, 72.2, 71.9, 71.8, 70.6, 70.5, 70.4, 70.3, 68.9, 68.1, 57.3, 53.3, 51.3, 43.7, 42.5, 39.2, 36.7, 36.4, 31.6, 27.3, 26.1, 25.8, 18.3, 17.3, 17.2, 17.0, 16.7, 15.5, 7.0. HRMS m/z calcd for $C_{66}H_{91}N_3O_{27}Na^+$ [M+Na]$^+$ 1380.5732, found 1380.5744.

MTM23. (31 mg, 43%) was prepared as a yellow solid from MTM A (25 mg, 0.023 mmol) using methyl (2-(aminooxy) acetyl)-L-phenylalanyl-L-tryptophanate (22 mg, 0.046 mmol), MeOH (450 uL), TFA (5 uL) following general procedure. $^1$H NMR (400 MHz, Methanol-d4) δ 8.23 (d, J=7.7 Hz, 1H), 8.14 (d, J=8.1 Hz, 1H), 7.41 (d, J=7.9 Hz, 1H), 7.29 (d, J=8.2 Hz, 1H), 7.23-7.16 (m, 5H), 7.08-7.02 (m, 2H), 6.95 (t, J=7.5 Hz, 1H), 6.90 (s, 1H), 6.64 (s, 1H), 5.05 (t, J=10.7 Hz, 2H), 4.98 (d, J=9.6 Hz, 1H), 4.75-4.50 (m, 911), 4.31-4.24 (m, 2H), 3.85 (d, J=12.1 Hz, 1H), 3.75-3.67 (m, 3H), 3.63-3.49 (m, 7H), 3.42 (s, 3H), 3.15-2.87 (m, 11H), 2.73-2.52 (m, 2H), 2.27-2.07 (m, 6H), 1.99-1.86 (m, 2H), 1.77 (q, J=11.9 Hz, 2H), 1.64-1.50 (m, 3H), 1.36-1.22 (m, 1811), 1.19 (d, J=6.0 Hz, 3H). $^{13}$C NMR (101 MHz, Methanol-d4) δ 203.3, 171.9, 171.3, 170.7, 163.6, 161.4, 158.8, 155.3, 138.4, 136.6, 136.4, 136.3, 129.0, 128.0, 127.2, 126.3, 123.2, 121.0, 118.4, 117.7, 116.9, 110.9, 110.4, 108.8, 108.0, 107.3, 100.7, 100.4, 98.5, 98.4, 97.4, 96.0, 79.5, 79.4, 77.2, 76.6, 76.4, 75.8, 75.1, 74.7, 73.4, 72.2, 72.1, 71.8, 70.5, 70.4, 70.3, 69.0, 68.1, 57.4, 54.0, 53.1, 53.0, 51.3, 43.8, 42.3, 39.2, 37.6, 36.7, 36.3, 31.6, 27.0, 26.2, 25.7, 18.4, 17.3, 17.2, 17.0, 16.7, 15.5, 7.0. HRMS m/z calcd for $C_{75}H_{101}N_4O_{28}$ $[M+1]^+$ 1505.6597, found 1505.6624.

MTM24. (29.5 mg, 53%) was prepared as a yellow solid from MTM A (25 mg, 0.023 mmol) using methyl (2-(aminooxy)acetyl)-L-tryptophyl-L-tryptophanate (23 mg, 0.046 mmol), MeOH (450 uL), TFA (5 uL) following general procedure. $^1$H NMR (400 MHz, Methanol-d4) δ 8.008-7.99 (m, 2H), 7.54 (d, J=8.0 Hz, 1H), 7.35 (d, J=7.9 Hz, 1H), 7.29 (t, J=8.7 Hz, 21-1), 7.10-7.01 (m, 3H), 7.00-6.88 (m, 4H), 6.58 (s, 1H), 5.04 (d, J=9.6 Hz, 1H), 5.01-4.95 (m, 2H), 4.80-4.72 (m, 1H), 4.71-4.46 (m, 7H), 4.24 (s, 2H), 3.82 (d, J=12.0 Hz, 1H), 3.74-3.65 (m, 3H), 3.62-3.44 (m, 7H), 3.42-3.34 (m, 4H), 3.27-3.21 (m, 1H), 3.18-2.83 (m, 10H), 2.74-2.50 (m, 2H), 2.28-2.04 (m, 5H), 1.91 (d, J=13.3 Hz, 2H), 1.83-1.65 (m, 2H), 1.65-1.46 (m, 4H), 1.33-1.24 (m, 18H), 1.16 (d, J=5.1 Hz, 3H). $^{13}$C NMR (101 MHz, Methanol-d4) δ 203.2, 171.9, 171.8, 171.6, 171.5, 170.8, 170.7, 163.6, 161.4, 158.8, 155.3, 138.4, 136.4, 136.3, 136.2, 127.4, 127.3, 127.2, 125.2, 123.3, 123.2, 120.9, 118.5, 118.4, 118.0, 117.7, 116.9, 110.9, 110.8, 110.4, 109.1, 108.7, 108.0, 107.3, 100.8, 100.4, 98.5, 98.4, 97.4, 96.0, 79.5, 79.3, 77.2, 77.0, 76.7, 76.4, 75.8, 75.1, 74.7, 73.3, 72.3, 72.1, 71.8, 71.7, 70.6, 70.5, 70.4, 70.3, 68.9, 68.1, 57.4, 53.7, 53.3, 53.2, 51.2, 43.7, 42.3, 39.2, 36.7, 36.3, 31.6, 27.1, 26.2, 25.9, 25.8, 18.4, 17.3, 17.2, 17.0, 16.7, 15.5, 7.0. HRMS m/z calcd for $C_{77}H_{102}N_5O_{28}$ $[M+1]^+$ 1544.6706, found 1544.6725.

Growth inhibition assay to assess cytotoxicity in ETS vs non-ETS expressing cells. Cells were seeded in clear 96-well plates (VWR, Radnor, Pa.). Seeding densities were optimized for each cell line to support 5 days of linear growth. Following a 24 hours attachment period, cells in duplicate wells were treated with half-log increments of respective compounds (0 nM and 0.3 nM-10 µM). Working stocks were prepared from an initial 10 mM drug stock diluted in either 100% ethanol or dimethyl sulfoxide (DMSO). All wells contained a final concentration of 0.1% (v/v) respective organic solvent. Immediately following treatment, cell viability was measured for vehicle control (Day 0) wells. Cell viability was measured in the remaining wells after 72 hours of incubation with compound or vehicle control (Day 3). For viability measurements, 0.1 mM resazurin (Sigma, St. Louis, Mo.) was added to wells and following 3 hours of incubation at 37° C., fluorescence readings (EM 560 nm, EX 590 nm) were recorded using a SpectraMax M5 plate reader (Molecular Devices, Sunnyvale, Calif.).

Percent viability, relative to the initial cell seeding concentration, was calculated by (($Treatment_{Day3}$–Vehicle $Control_{Day3}$)/(Vehicle $Control_{Day3}$–Vehicle $Control_{Day0}$))×100. Percent cell viability was plotted as a function of compound concentration (Log [M]) and the data were fit using a 3-parameter non-linear model with fixed Hill slope constant and 4-parameter non-linear model with variable Hill slope constant. The model with the best curve fit was used to estimate the $GI_{50}$ in GraphPad Prism 7.0 software (GraphPad Software, La Jolla, Calif.). The 3-parameter equation used was Y=Bottom+(Top–Bottom)/(1+10 ((X–Log $[IC_{50}]$))). The 4-parameter equation used was Y=Bottom+(Top–Bottom)/(1+10^((Log$[IC_{50}]$–X)*Hillslope)). Top and Bottom are plateaus in the units of the Y-axis (response). $IC_{50}$ is the response (Y-axis) halfway between Top and Bottom plateaus.

$GI_{50}$ values were determined by pooling all available experiments and reported with 95% confidence interval, calculated from GraphPad Prism 7.0 software curve fit. All compounds were tested at least once in multi-well replicates and each experiment included one a control compound (i.e., MTM) to ensure the stable response of the cell lines. The selectivity index was estimated by determining the ratio of $GI_{50}$ estimates between ETS fusion negative and ETS fusion positive cell lines. Median values are reported since the $GI_{50}$ was not estimable in some cases because the compounds did not elicit toxicity, even at high micromolar concentrations.

Luciferase reporter assay to assess target engagement. TC-32 cells (expressing EWS-FLI1) under G418 (1 mg/mL) or puromycin (0.1 mg/mL) selection, expressing either cloned pGLuc-Basic 2 or pCMV-Red Firefly vector, respectively, were seeded in clear 96-well plates at a density of 10,000 cells/well. pGLuc vectors contained either the NROB1 promoter region or a DNA sequence with Sp1 consensus binding site or the beta-actin promoter region, which contains multiple Sp1 binding sites. Following a 24 hours attachment period, cells were treated in duplicate with half-log increments of respective compounds (0 nM and 0.3 nM-10 µM). After a 12 hours treatment, media was removed, and cells were washed 3 times with DPBS (Thermo Fisher Scientific, Waltham, Mass.). Cells were directly lysed on a plate shaker for 30 minutes at room temperature using 100 µL of passive membrane lysis solution. Lysates (80 µL) were transferred to a white luminescence plate. Luciferase substrate, either coelenterazine or D-luciferin (504 of 1× solution), for guassia or red firefly vectors, respectively, was added in a Glomax 96 microplate luminometer (Promega, Madison, Wis.) and luminescence was immediately measured. Delay before and after injections were set to the default of 0.4 seconds and a 10 seconds integration time was used. All reagents used in this assay were from the dual luciferase reporter assay system (Promega, Madison, Wis.). Concurrently, an additional 96 well plate was seeded and treated under the exact same conditions to determine cell viability using resazurin assay. Luminescence results were normalized to cell viability. EC50 values, as a measure of the effect of each compound on luciferase production, were estimated in GraphPad Prism using the same equations described in the "Growth Inhibition Assay."

TABLE 1

Cellular Selectivity

| | R | TC32/PC3 (nM) | PC:TC32 |
|---|---|---|---|
| MTM (1) | 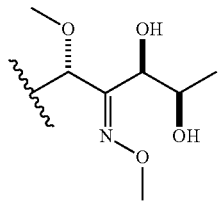 | 88/145 | 1.66 |

TABLE 1-continued
| | Cellular Selectivity | | |
|---|---|---|---|
| R | | TC32/PC3 (nM) | PC:TC32 |
| MTM (2) | 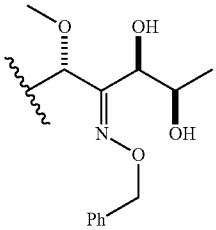 | 118/127 | 1.08 |
| MTM (3) | 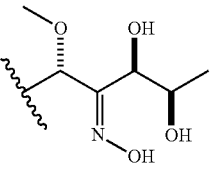 [SMILES: *[C@H](OC)/C(=N/O)[C@@H](O)[C@@H](C)O] | 237/440 | 1.86 |
| MTM (4) | 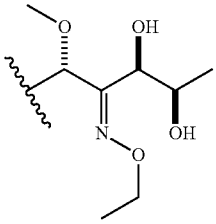 [SMILES: *[C@H](OC)/C(=N/OCC)[C@@H](O)[C@@H](C)O] | 55/63 | 1.15 |
| MTM (5Z) | 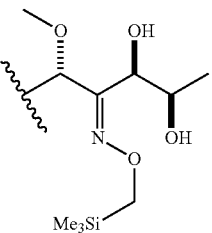 [SMILES: *[C@H](OC)/C(=N/OC[Si](C)(C)C)[C@@H](O)[C@@H](C)O] | 737/498 | 0.68 |
| MTM (5E) | 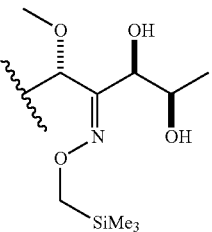 [SMILES: *[C@H](OC)/C(=N\OC[Si](C)(C)C)[C@@H](O)[C@@H](C)O] | 1696/2173 | 1.28 |
| MTM (7Z) | 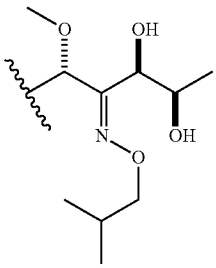 [SMILES: *[C@H](OC)/C(=N/OCC(C)C)[C@@H](O)[C@@H](C)O] | 80/92 | 1.15 |

TABLE 1-continued

| | Cellular Selectivity | | |
|---|---|---|---|
| | R | TC32/PC3 (nM) | PC:TC32 |
| MTM (7E) | | 578/600 | 1.04 |
| MTM (10) | | 116/128 | 1.10 |
| MTM (11) | | 79/103 | 1.30 |
| MTM (12) | | 1407/1877 | 1.33 |
| MTM (14Z) | | 28/82 | 2.91 |

TABLE 1-continued
| | Cellular Selectivity | | |
|---|---|---|---|
| | R | TC32/PC3 (nM) | PC:TC32 |
| MTM (14E) | 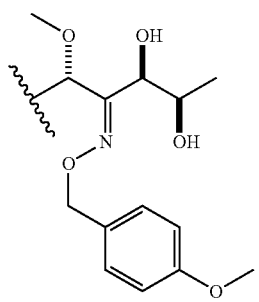 [SMILES: *[C@H](OC)/C(=N\OCc1ccc(OC)cc1)[C@@H](O)[C@@H](C)O] | 281/577 | 2.05 |
| MTM (15Z) | 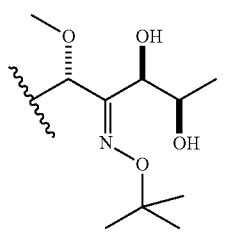 [SMILES: *[C@H](OC)/C(=N/OC(C)(C)C)[C@@H](O)[C@@H](C)O] | 70/158 | 2.25 |
| MTM (15E) | 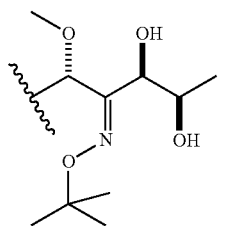 [SMILES: *[C@H](OC)/C(=N\OC(C)(C)C)[C@@H](O)[C@@H](C)O] | 333/623 | 1.87 |
| MTM (16) | 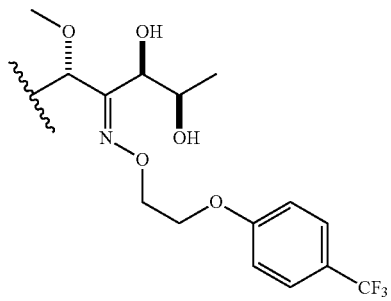 [SMILES: *[C@H](OC)/C(=N/OCCOc1ccc(C(F)(F)F)cc1)[C@@H](O)[C@@H](C)O] | 1265/10000 | 7.91 |
| MTM (17Z) | 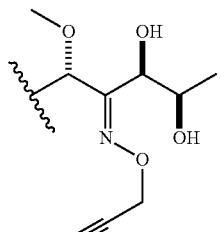 | 38/72 | 1.89 |

TABLE 1-continued

| | Cellular Selectivity | | |
|---|---|---|---|
| | R | TC32/PC3 (nM) | PC:TC32 |
| MTM (17E) | (structure) | 125/301 | 2.40 |
| MTM (18) | (structure) | 190/1266 | 6.44 |
| MTM (19) | (structure) | 27/46 | 1.70 |
| MTM (19E) | (structure) | 547/768 | 1.40 |
| MTM (20) | (structure) | 144/3542 | 24.5 |

TABLE 1-continued
| | Cellular Selectivity | |
|---|---|---|
| R | TC32/PC3 (nM) | PC:TC32 |
MTM (21) 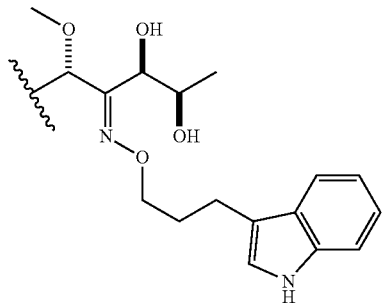 [SMILES: *[C@H](OC)/C(=N/OCCCc1c[nH]c2ccccc12)[C@@H](O)[C@@H](C)O]  48/66  1.38
MTM (22) 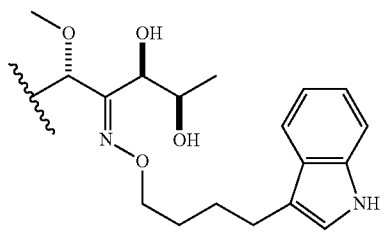 [SMILES: *[C@H](OC)/C(=N/OCCCCc1c[nH]c2ccccc12)[C@@H](O)[C@@H](C)O]  55/84  1.54
MTM (23) 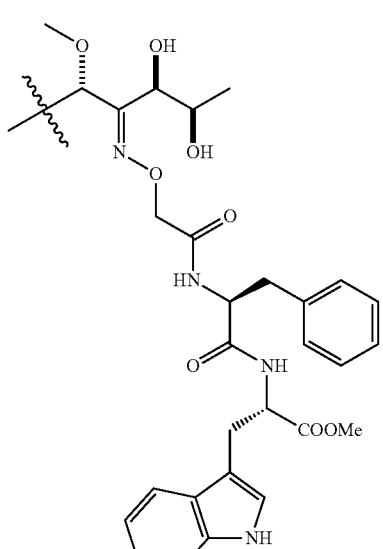  80/582  7.31

TABLE 1-continued
| | Cellular Selectivity | |
|---|---|---|
| R | TC32/PC3 (nM) | PC:TC32 |
MTM (24) 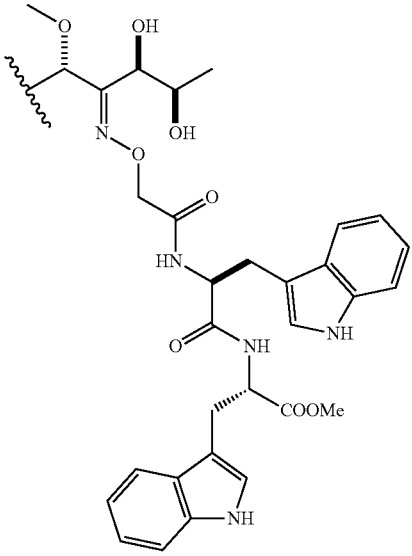 [SMILES: *[C@H](OC)/C(=N/OCC(=O)N[C@@H](Cc1c[nH]c2ccccc12)C(=O)N[C@@H](Cc1c[nH]c2ccccc12)C(=O)OC)[C@@H](O)[C@@H](C)O]  801/5570  6.9
MTM (25) 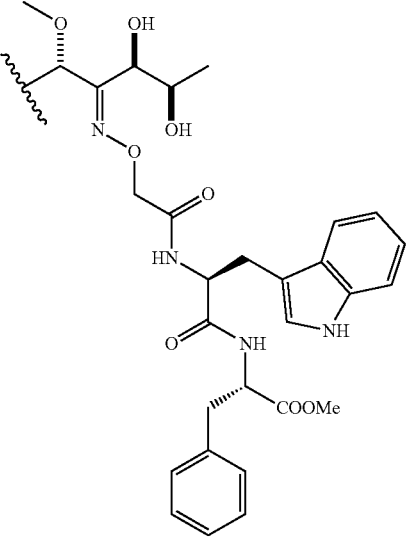 [SMILES: *[C@H](OC)/C(=N/OCC(=O)N[C@@H](Cc1c[nH]c2ccccc12)C(=O)N[C@@H](Cc1ccccc1)C(=O)OC)[C@@H](O)[C@@H](C)O]  117/700  5.98
MTM (26) 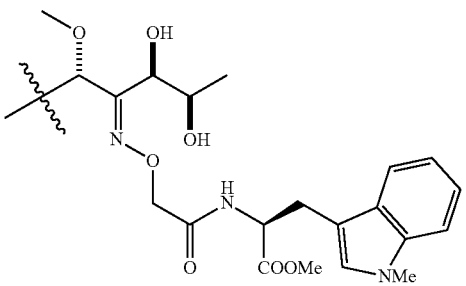 [SMILES: *[C@H](OC)/C(=N/OCC(=O)N[C@@H](Cc1cn(C)c2ccccc12)C(=O)OC)[C@@H](O)[C@@H](C)O]  126/771  5.64

TABLE 1-continued

| | Cellular Selectivity | | |
|---|---|---|---|
| R | | TC32/PC3 (nM) | PC:TC32 |
| MTM (27) | (structure) | 61/431 | 7.06 |
| MTM (28) | (structure) | 397/4637 | 11.68 |
| MTM (29) | (structure) | 366/580 | 1.58 |
| MTM (30) | (structure) | 279/579 | 2.08 |

TABLE 1-continued
| | Cellular Selectivity | | |
|---|---|---|---|
| | R | TC32/PC3 (nM) | PC:TC32 |
| MTM (31) | 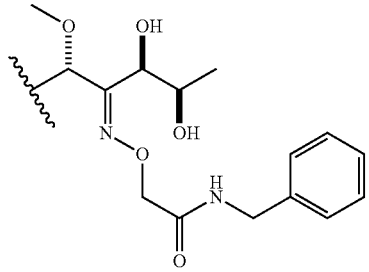 [SMILES: *[C@H](OC)/C(=N/OCC(=O)NCc1ccccc1)[C@@H](O)[C@@H](C)O] | 115/211 | 1.83 |
| MTM (32) | 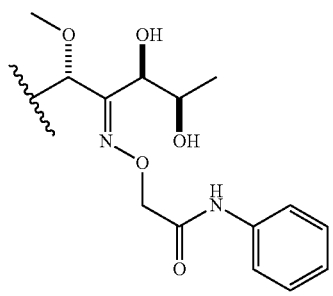 [SMILES: *[C@H](OC)/C(=N/OCC(=O)Nc1ccccc1)[C@@H](O)[C@@H](C)O] | 36/40 | 1.11 |
| MTM (33) | 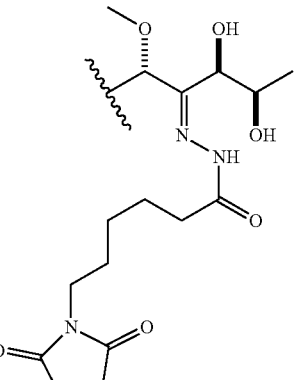 | 551/1526 | 3.9 |
| MTM (34) | 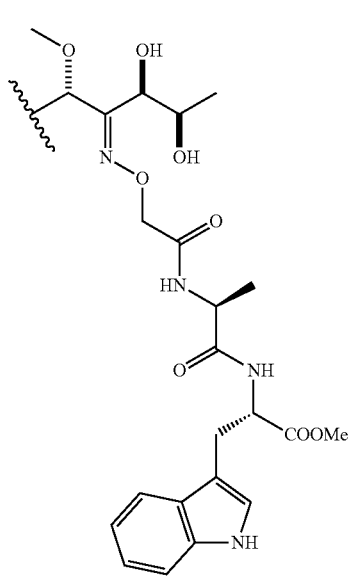 [SMILES: *[C@H](OC)/C(=N/OCC(=O)N[C@@H](C)C(=O)N[C@@H](Cc1c[nH]c2ccccc12)C(=O)OC)[C@@H](O)[C@@H](C)O] | 390/1670 | 4.28 |

TABLE 1-continued

| | Cellular Selectivity | | |
|---|---|---|---|
| | R | TC32/PC3 (nM) | PC:TC32 |
| MTM (35) | [structure: methoxy, OH, OH, oxime-O-CH2-C(O)-NH-CH(COOH)-CH2-(N-Me indole)] | >10000/>10000 | / |
| MTM (36) | [structure: OH, OH, OH, HN-CH2CH2-SH] | 1202:2155 | 1.8 |
| MTM (39) | [structure: methoxy, OH, OH, oxime-O-CH2-C(O)-NH-CH(COOH)-CH2-(indole)] | 1346/10000 | 7.4 |
| MTM (40) | [structure: methoxy, OH, OH, oxime-O-CH2-C(O)-NH-CH(C(O)NHMe)-CH2-(indole)] | 445/5240 | 11.8 |

TABLE 1-continued
| | Cellular Selectivity | |
|---|---|---|
| R | TC32/PC3 (nM) | PC:TC32 |
MTM (41) 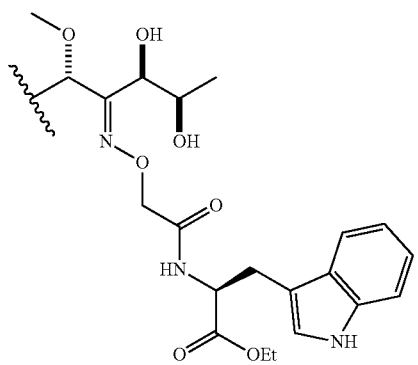 [SMILES: *[C@H](OC)/C(=N/OCC(=O)N[C@@H](Cc1c[nH]c2ccccc12)C(=O)O)[C@@H](O)[C@@H](C)O] 236/3191 13.5
MTM (42) 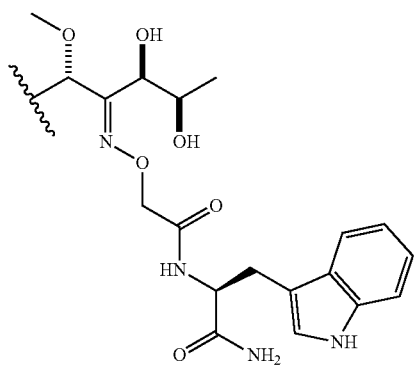 [SMILES: *[C@H](OC)/C(=N/OCC(=O)N[C@@H](Cc1c[nH]c2ccccc12)C(N)=O)[C@@H](O)[C@@H](C)O] 489/4165 8.5
MTM (43) 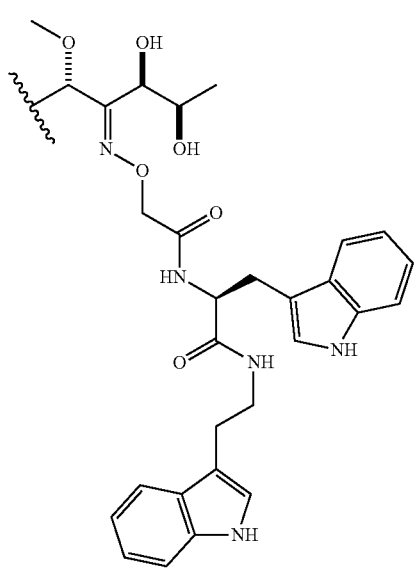 [SMILES: *[C@H](OC)/C(=N/OCC(=O)N[C@@H](Cc1c[nH]c2ccccc12)C(=O)NCCc1c[nH]c2ccccc12)[C@@H](O)[C@@H](C)O] 545/1393 2.6

TABLE 1-continued

| | Cellular Selectivity | |
|---|---|---|
| R | TC32/PC3 (nM) | PC:TC32 |

MTM (44) [structure] 57/2021 35

MTM (45) [structure] 84/201 2.4

MTM (46) [structure] 10000/10000 /

TABLE 1-continued
| | Cellular Selectivity | | |
|---|---|---|---|
| | R | TC32/PC3 (nM) | PC:TC32 |
| MTM (47) | 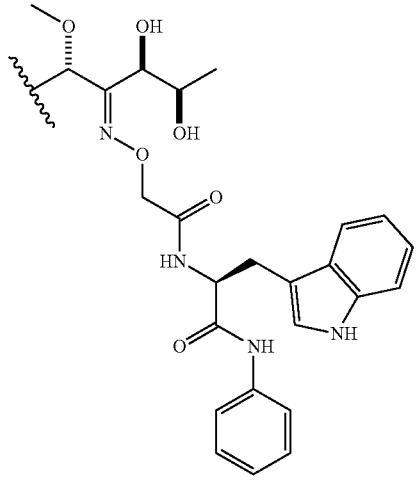 [SMILES: *[C@H](OC)/C(=N/OCC(=O)N[C@@H](Cc1c[nH]c2ccccc12)C(=O)Nc1ccccc1)[C@@H](O)[C@@H](C)O] | 237/644 | 2.7 |
| MTM (48) | 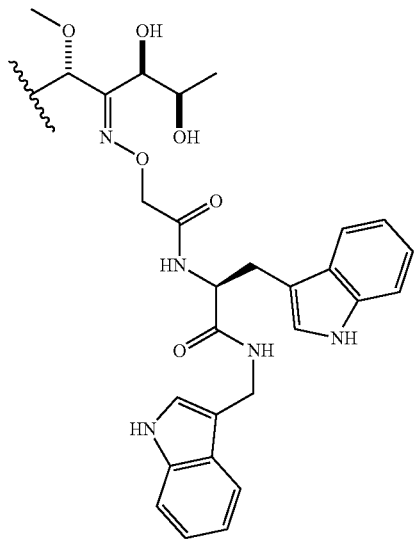 [SMILES: *[C@H](OC)/C(=N/OCC(=O)N[C@@H](Cc1c[nH]c2ccccc12)C(=O)NCc1c[nH]c2ccccc12)[C@@H](O)[C@@H](C)O] | 596/1400 | 2.30 |
| MTM (49) | 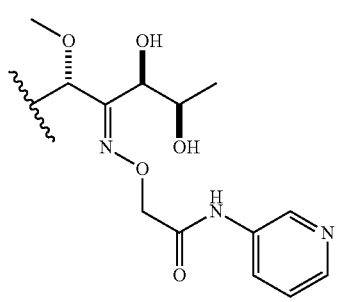 [SMILES: *[C@H](OC)/C(=N/OCC(=O)Nc1cccnc1)[C@@H](O)[C@@H](C)O] | 77/185 | 2.4 |

TABLE 1-continued
| | Cellular Selectivity | |
|---|---|---|
| R | TC32/PC3 (nM) | PC:TC32 |
MTM (50) 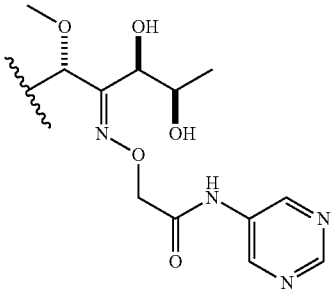 [SMILES: *[C@H](OC)/C(=N/OCC(=O)Nc1cncnc1)[C@@H](O)[C@@H](C)O]  361/985  2.7
MTM (51) 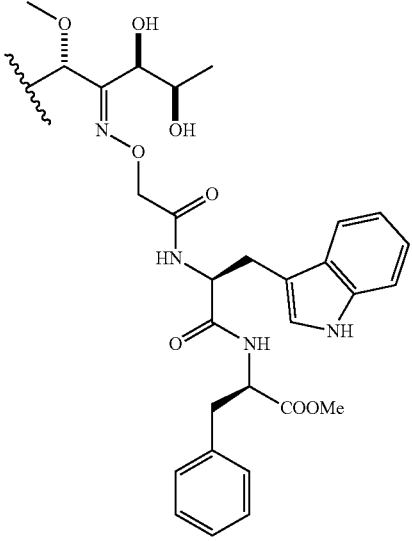 [SMILES: *[C@H](OC)/C(=N/OCC(=O)N[C@@H](Cc1c[nH]c2ccccc12)C(=O)N[C@H](Cc1ccccc1)C(=O)OC)[C@@H](O)[C@@H](C)O]  116/258  2.2
MTM (52) 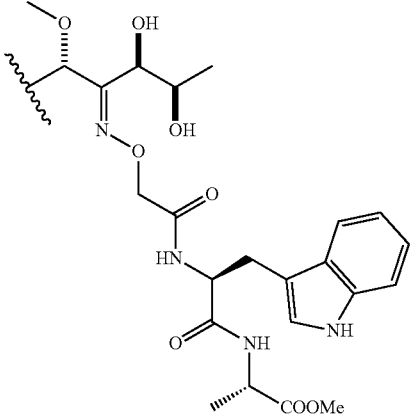 [SMILES: *[C@H](OC)/C(=N/OCC(=O)N[C@@H](Cc1c[nH]c2ccccc12)C(=O)N[C@@H](C)C(=O)OC)[C@@H](O)[C@@H](C)O]  313/2086  6.6

TABLE 1-continued
| | Cellular Selectivity | |
|---|---|---|
| R | TC32/PC3 (nM) | PC:TC32 |
| MTM (53) 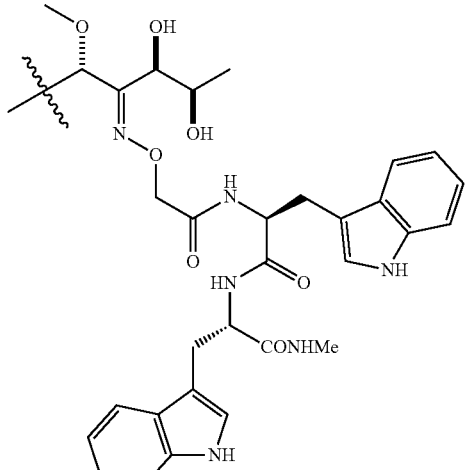 | 841/4193 | 5.0 |
| MTM (54) 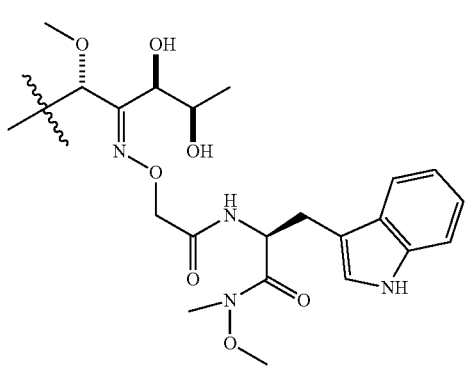 [SMILES: *[C@H](OC)/C(=N/OCC(=O)N[C@@H](Cc1c[nH]c2ccccc12)C(=O)N(C)OC)[C@@H](O)[C@@H](C)O] | 786/1336 | 1.7 |
| MTM (55) 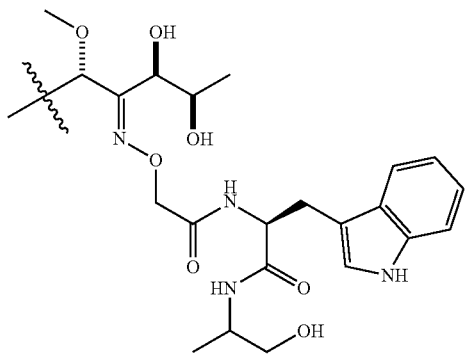 [SMILES: *[C@H](OC)/C(=N/OCC(=O)N[C@@H](Cc1c[nH]c2ccccc12)C(=O)NC(C)CO)[C@@H](O)[C@@H](C)O] | 156/420 | 2.7 |

TABLE 1-continued
| | Cellular Selectivity | |
|---|---|---|
| R | TC32/PC3 (nM) | PC:TC32 |
MTM (56) 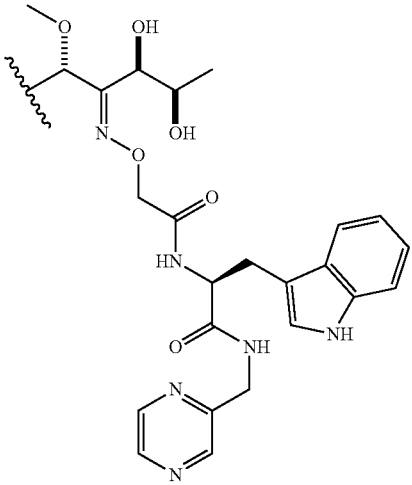 [SMILES: *[C@H](OC)/C(=N/OCC(=O)N[C@@H](Cc1c[nH]c2ccccc12)C(=O)NCc1cnccn1)[C@@H](O)[C@@H](C)O] 1762/3386    1.9
MTM (57) 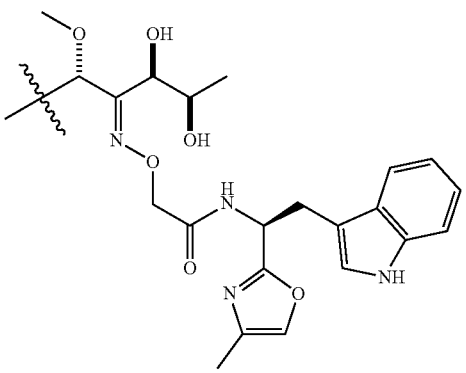 [SMILES: *[C@H](OC)/C(=N/OCC(=O)N[C@@H](Cc1c[nH]c2ccccc12)c1nc(C)co1)[C@@H](O)[C@@H](C)O] 299/998    3.3
MTM (58) 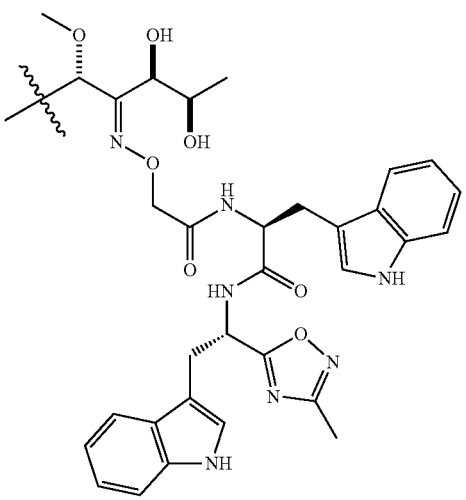 [SMILES: *[C@H](OC)/C(=N/OCC(=O)N[C@@H](Cc1c[nH]c2ccccc12)C(=O)N[C@@H](Cc1c[nH]c2ccccc12)c1nc(C)no1)[C@@H](O)[C@@H](C)O] 127/306    2.4

TABLE 1-continued
| | Cellular Selectivity | | |
|---|---|---|---|
| | R | TC32/PC3 (nM) | PC:TC32 |
| MTM (58) | 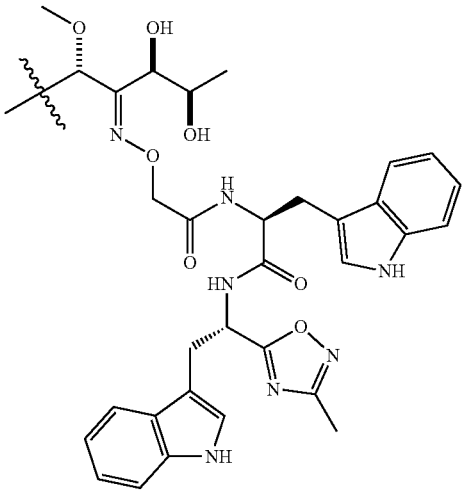 [SMILES: *[C@H](OC)/C(=N/OCC(=O)N[C@@H](Cc1c[nH]c2ccccc12)C(=O)N[C@@H](Cc1c[nH]c2ccccc12)c1nc(C)no1)[C@@H](O)[C@@H](C)O] | 127/306 | 2.4 |
| MTM (59) | 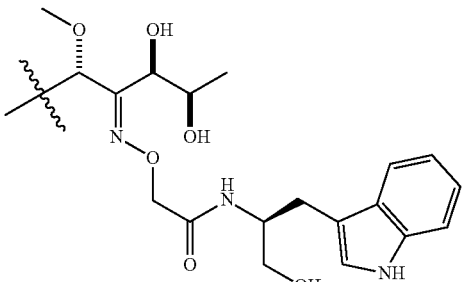 | 67/321 | 4.8 |
| MTM (60) | 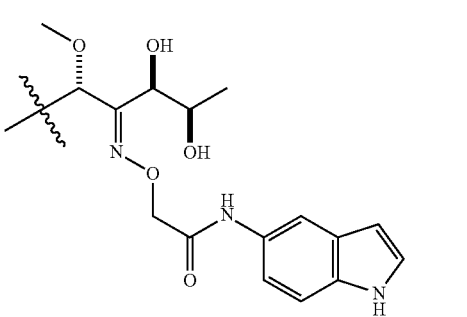 [SMILES: *[C@H](OC)/C(=N/OCC(=O)Nc1ccc2[nH]ccc2c1)[C@@H](O)[C@@H](C)O] | 15/148 | 10 |
| MTM (61) | 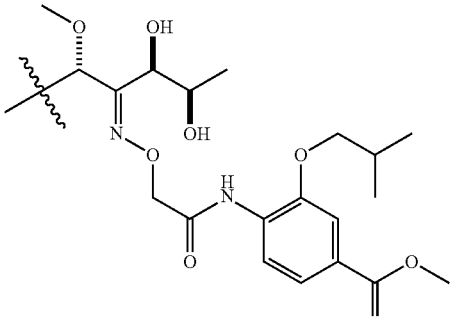 | 3.6/2.04 | 5.7 |

TABLE 1-continued

| | Cellular Selectivity | |
|---|---|---|
| R | TC32/PC3 (nM) | PC:TC32 |// 
| MTM (62) [structure] | >20000/>20000 | \ |
| MTM (63) [structure] | 11/147 | 13.3 |
| MTM (64) [structure] | 3.5/43 | 12.3 |
| MTM (65) [structure] | 5.3/107 | 20.1 |

TABLE 1-continued
| | Cellular Selectivity | | |
|---|---|---|---|
| | R | TC32/PC3 (nM) | PC:TC32 |
| MTM (66) | 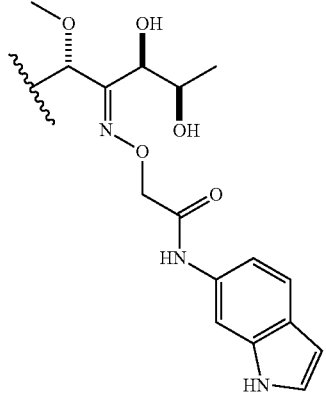 [SMILES: *[C@H](OC)/C(=N/OCC(=O)Nc1ccc2cc[nH]c2c1)[C@@H](O)[C@@H](C)O] | 1.3/5/6 | 4.2 |
| MTM (67) | 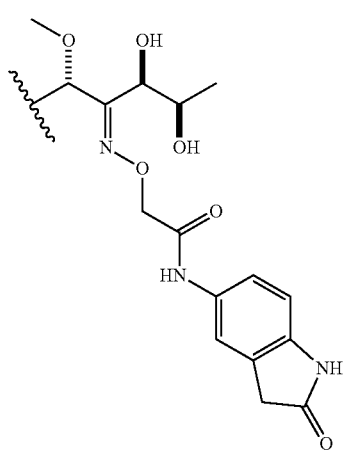 [SMILES: *[C@H](OC)/C(=N/OCC(=O)Nc1ccc2c(c1)CC(=O)N2)[C@@H](O)[C@@H](C)O] | 1339/5018 | 3.8 |
| MTM (68) | 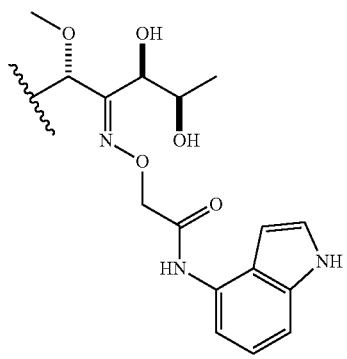 [SMILES: *[C@H](OC)/C(=N/OCC(=O)Nc1cccc2[nH]ccc12)[C@@H](O)[C@@H](C)O] | 15/68 | 4.5 |

TABLE 1-continued
| | Cellular Selectivity | | |
|---|---|---|---|
| | R | TC32/PC3 (nM) | PC:TC32 |
| MTM (69) | 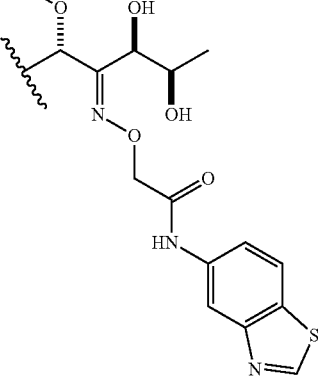 | 144/1646 | 11.4 |
| MTM (70) | 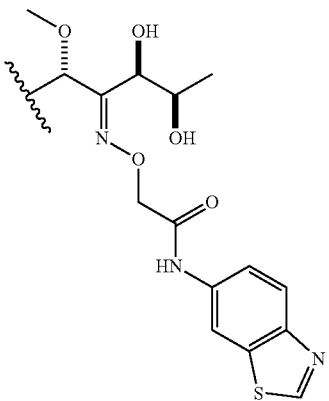 [SMILES: *[C@H](OC)/C(=N/OCC(=O)Nc1ccc2ncsc2c1)[C@@H](O)[C@@H](C)O] | 35/251 | 7.2 |
| MTM (71) | 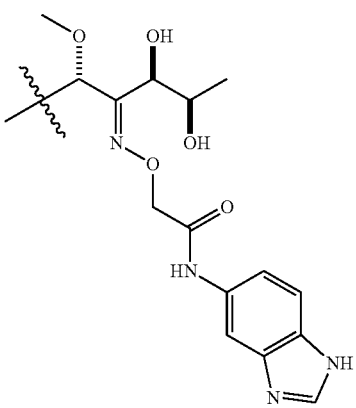 [SMILES: *[C@H](OC)/C(=N/OCC(=O)Nc1ccc2[nH]cnc2c1)[C@@H](O)[C@@H](C)O] | 208/667 | 3.2 |
| MTM (72) | 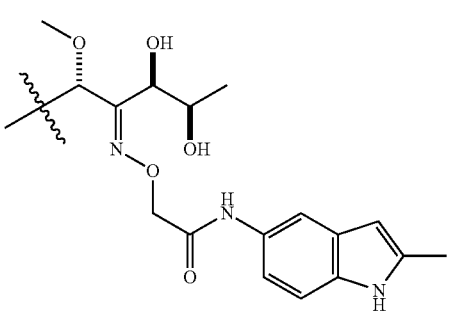 [SMILES: *[C@H](OC)/C(=N/OCC(=O)Nc1ccc2[nH]c(C)cc2c1)[C@@H](O)[C@@H](C)O] | 12/278 | 20.9 |

TABLE 1-continued

Cellular Selectivity

| R | TC32/PC3 (nM) | PC:TC32 |
|---|---|---|
| MTMox (73) 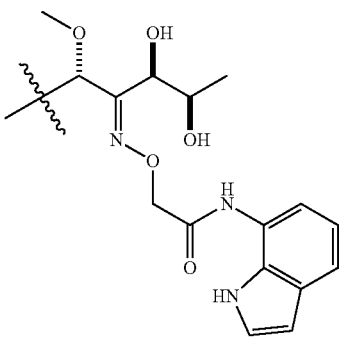 [SMILES: *[C@H](OC)/C(=N/OCC(=O)Nc1cccc2cc[nH]c12)[C@@H](O)[C@@H](C)O] | 0.98/5.27 | 5.9 |
| MTM (74) 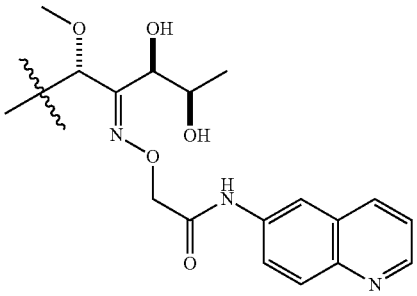 [SMILES: *[C@H](OC)/C(=N/OCC(=O)Nc1ccc2ncccc2c1)[C@@H](O)[C@@H](C)O] | 144/9586 | 66.6 |
| MTM (75) 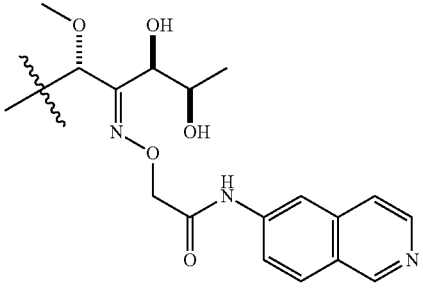 [SMILES: *[C@H](OC)/C(=N/OCC(=O)Nc1ccc2cnccc2c1)[C@@H](O)[C@@H](C)O] | 66.7/7884 | 118 |
| MTMox (76) 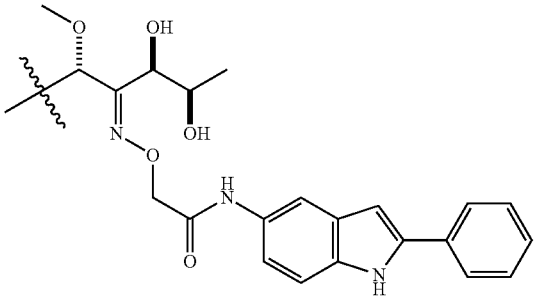 [SMILES: *[C@H](OC)/C(=N/OCC(=O)Nc1ccc2[nH]c(-c3ccccc3)cc2c1)[C@@H](O)[C@@H](C)O] | 3109/20000 | \ |

Growth inhibition assay to assess cytotoxicity in EWS-FLI1 silenced TC32 cells. TC32 cells with inducible silencing of EWS-FLI1 or shControl were used to assay the cytotoxicity of analogues before and after silencing. The ratio of GI50 values before and after silencing was used as an estimate of target engagement. Compounds with higher GI50 values following silencing of EWS-FLI1 were considered to depend on EWS-FLI1 for their activity since cells were more resistant. The cell lines were a kind gift from Dr. Kimberly Stegmaier (Harvard University) and their generation has been reported (Cancer Cell. 2018 Feb. 12; 33(2): 202-216.). For a typical assay, 5000 cells were plated in a 96-well plate and allowed to attach for 24 hours. To induce and maintain silencing, cells were treated with doxycycline at 24 hours after seeding and twice more 48 hours apart. Cells were treated with each compound on the same day as the $2^{nd}$ doxycycline treatment and viability was assessed, as described in the Growth inhibition assay, 72 hours following drug treatments.

Figure 1B:
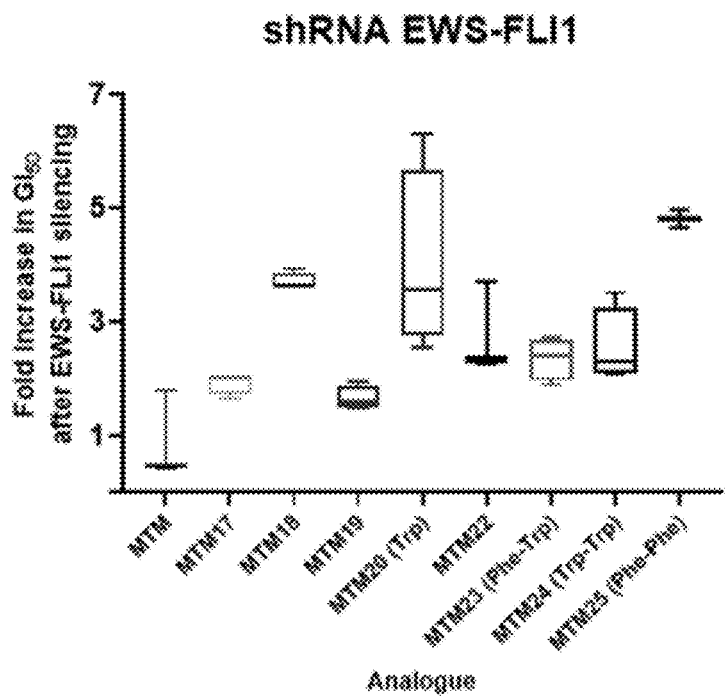

Reference is made to FIGS. 1A and 1B, which illustrate mechanistic assessment of target engagement using TC-32 cells with doxycycline inducible shRNA where GI50 ratio=silenced/unsilenced. Targeted (EWS-FLI1) silencing renders cells more resistant to the MTM derivatives as demonstrated by the higher IC50 after silencing.

Figure 2A:
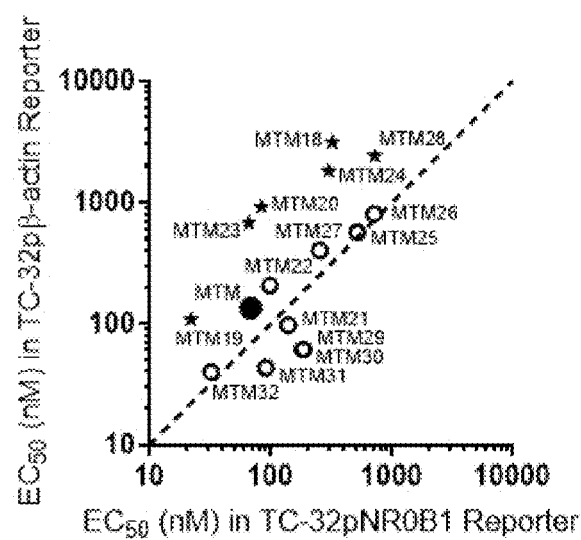
FIGS. 2A-2C include data assessing target engagement in TC32 cells.
Figure 2B:
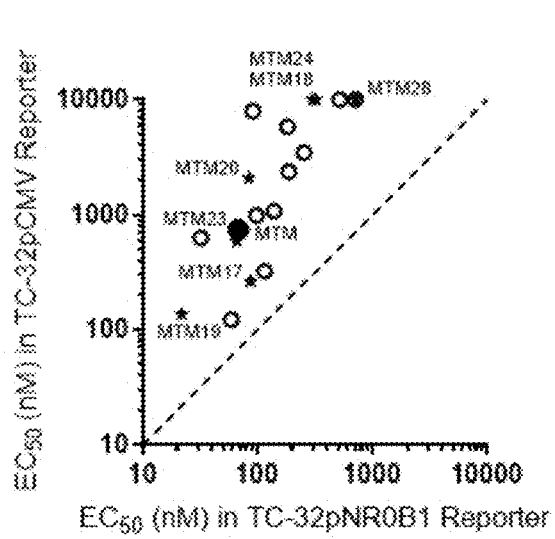
Figure 2C:
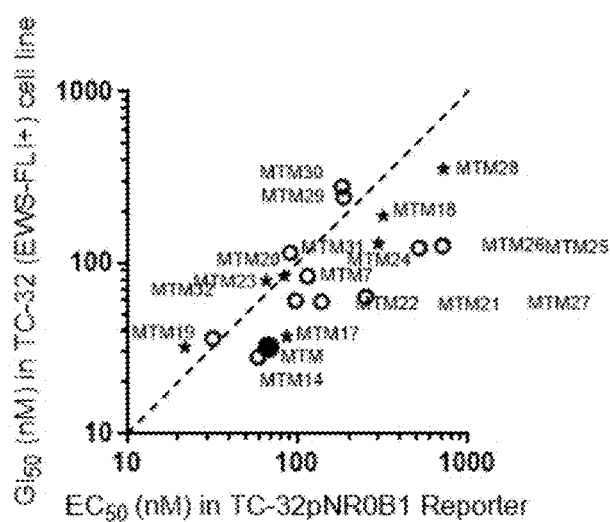

Reference is made to FIGS. 2A, 2B, and 2C. Target engagement was assessed in TC32 cells expressing luciferase under the control of NR0B1 (EWS-FLI1 binding sites) or b-actin (Sp1 binding sites) or CMV (control) promoters. The EC50 for each analog was estimated and an effective concentration (EC50) was estimated for a subset of MTM-oxime analogues in the three TC-32 reporter cell lines. FIG. 2A shows a number of analogues more selective for EWS-FLI1 (left of unity line) and panel FIG. 2B depicts that the analogues are less efficient in disrupting CMV driven luciferase activity. Overall there is a correlation between inhibition of luciferase in NROB1/EWS-FLI1 reporter and the GI50 estimated in TC32 cells.

Intravenous bolus pharmacokinetics of select analogues. Female Swiss Webster mice (n=9) were administered select compounds by intravenous bolus. Plasma samples were collected by saphenous bleed and terminal cardiac puncture at time points between 5 minutes and 24 hours, as needed for accurate pharmacokinetic profiling. Pipette tips and needles were primed with heparin for anti-coagulant. Whole blood was centrifuged at 3000×g to rapidly collect plasma and immediately stored at −80° C. until analysis. Plasma extracts were analyzed by HPLC-MS/MS as described in Eckenrode et al (Biomed Chromatogr. 2019 August; 33(8):e4544). All animal studies were conducted under approved institutional animal care and use committee (IACUC) protocol.

Efficacy studies in mouse xenografts. TC-32 cells were suspended in 1:1 (v/v) media: Matrigel on ice and injected subcutaneously into the flank of female immunocompromised athymic nude NU/NU mice at a density of $1.0 \times 10^6$ cells per 100 µL. Mice with tumors of at least 75 mm³ were randomly assigned to treatment groups, n=8-12 mice per group and n=6-10 mice per vehicle control treated group. Mice were treated at the maximum tolerated dose for 5-8 doses as indicated in the figures. Tumor volumes were monitored every 2-3 days and mice were euthanized once tumor volumes reached 1500 mm³. In some experiments, tumors were allowed to grow to 20 mm in one direction prior to animals being removed from the study. Average tumor volume among the replicates were plotted, as well as survival plots, using GraphPad Prism 7.03 software. All animal studies were conducted under approved institutional animal care and use committee (IACUC) protocol.

Figure 3A:
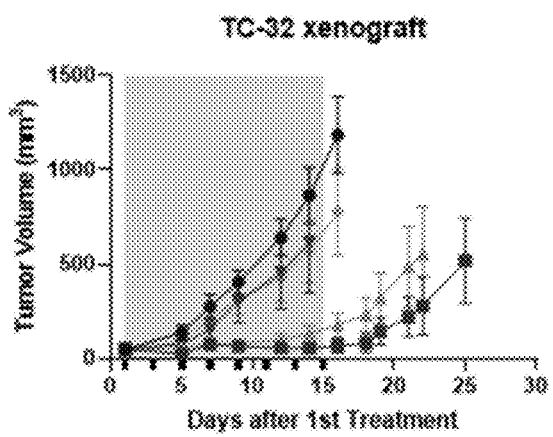
FIGS. 3A-3G include data from an efficacy study involving an exemplary compound as disclosed herein, in which TC-32 cells (EWS-FLI1+) were subcutaneously implanted in female NU/NU mice.
Figure 3B:
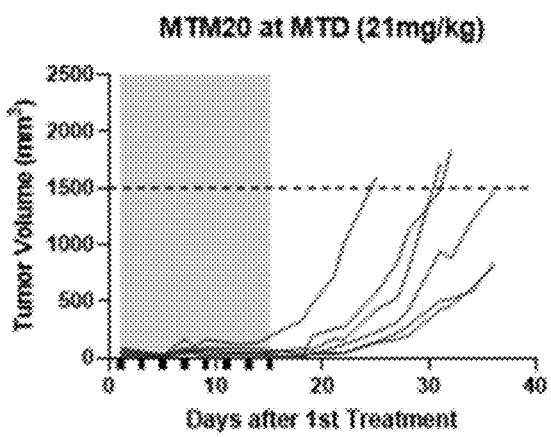
Figure 3C:
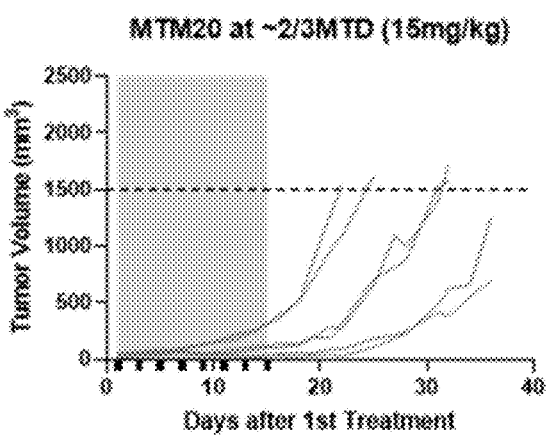
Figure 3D:
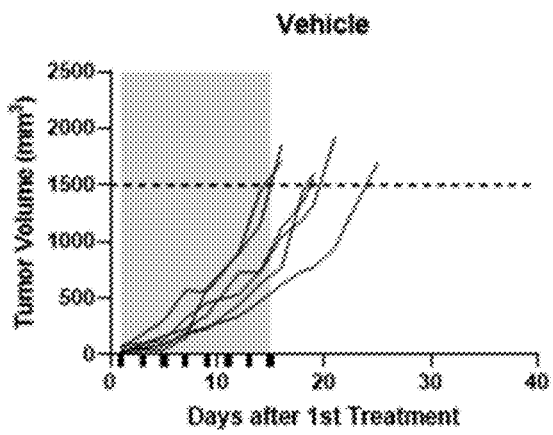
Figure 3E:
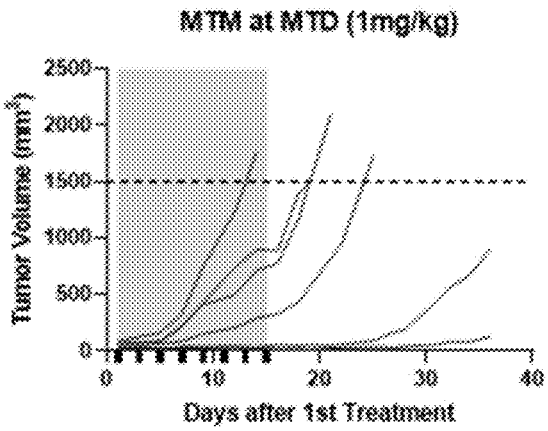
Figure 3F:
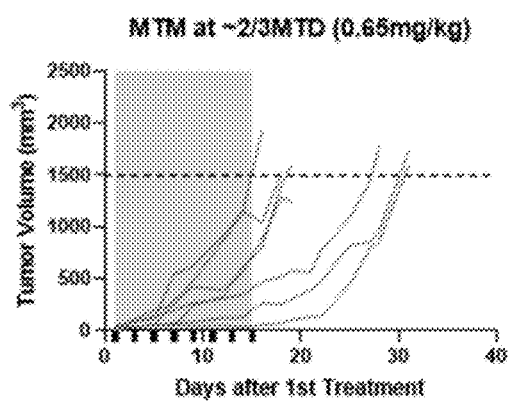
Figure 3G:
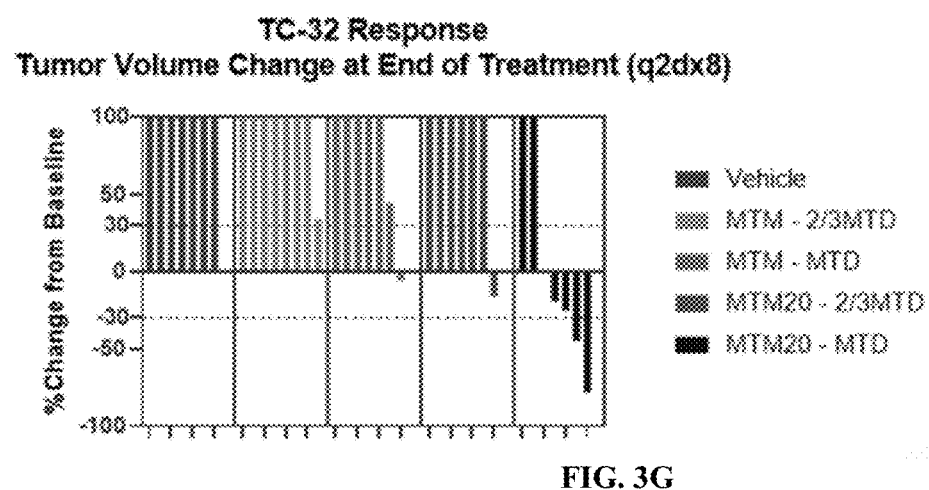

Reference is made to FIGS. 3A-3G, which include data from an efficacy study involving exemplary compound MTM (20). TC-32 cells (EWS-FLI1+) were subcutaneously implanted in female NU/NU mice. Gray shadding starting at 0 days. indicates dosing window. FIG. 3B includes MTM20 at 21 mg/kg, FIG. 3C includes MTM20 at 15 mg/kg, FIG. 3D includes vehicle (control), FIG. 3E includes MTM (control) at 1 mg/kg, and FIG. 3F includes MTM (control) at 0.65 mg/kg. Data presented together are shown in FIGS. 3A and 3G. Dosing route: IV bolus; Schedule: q2d×8.

Figure 4A:
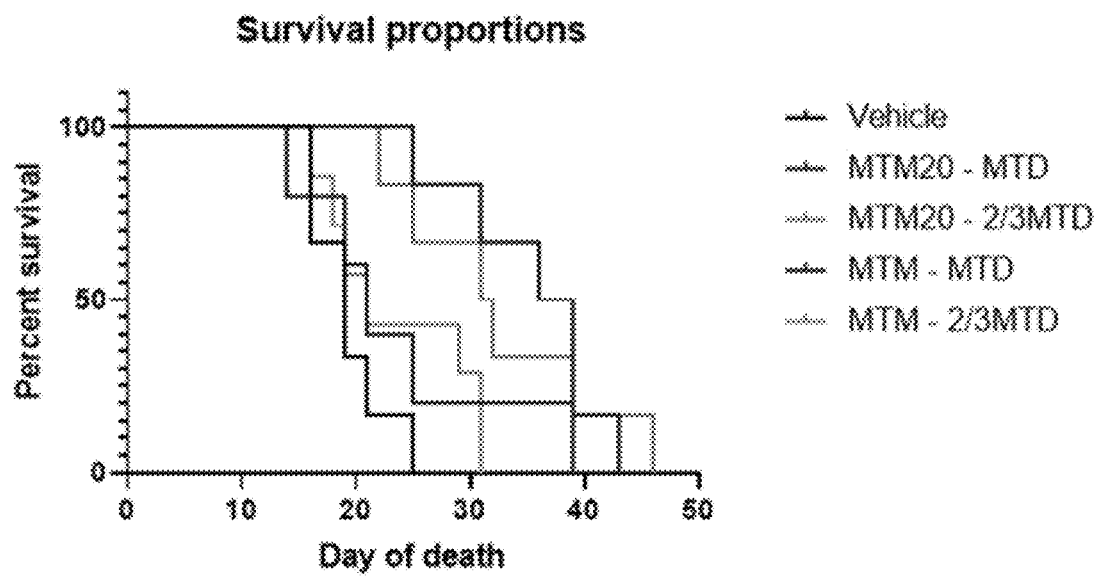
FIGS. 4A and 4B include data from an efficacy/survival study involving an exemplary compound as disclosed herein, in which TC-32 cells (EWS-FLI1+) were subcutaneously implanted in female NU/NU mice.
Figure 4B:
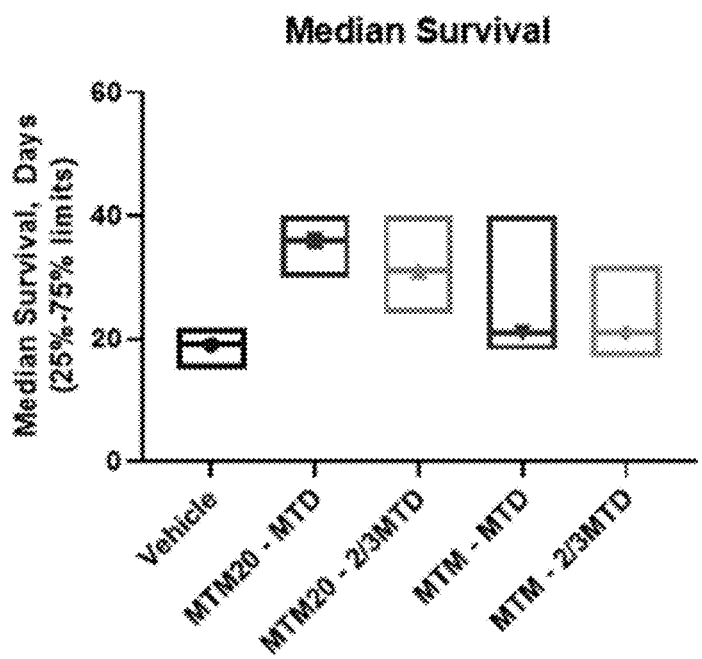

Reference is made to FIGS. 4A and 4B, and Table 2, which include data from an efficacy/survival study involving exemplary compound MTM(20). TC-32 cells (EWS-FLI1+) were subcutaneously implanted in female NU/NU mice. FIG. 4A includes survival curves and FIG. 4B includes median survival plots of mice (n=6-7/group). Statistical analysis (Log-Rank Test) of survival curves in provided in Table 2.

TABLE 2

| Log-Rank Test: (Sigma Plot 14.0) | | |
|---|---|---|
| Statistic | DF | P Value |
| 14.551 | 4 | 0.006 |

The log rank statistic for the survival curves is greater that would be expected by chance; there is a statistically significant difference between survival curves (P = 0.006). To isolate the group or groups that differ from the others use a multiple comparison procedure.
Multiple Comparisons:

All Pairwise Multiple Comparison Procedures (Bonferroni method):
Overall significance level = 0.05

| Comparisons | Statistic | P Value | Significant? |
|---|---|---|---|
| Vehicle vs. MTM20 – MTD | 10.549 | 0.0116 | Yes |
| Vehicle vs. MTM20 – 2/3 MTD | 8.538 | 0.0348 | Yes |
| MTM20 – MTD vs. MTM – 2/3 MTD | 6.775 | 0.0924 | No |
| MTM20 – 2/3 MTD vs. MTM – 2/3 MT | 4.225 | 0.398 | No |
| MTM20 – MTD vs. MTM20 – 2/3 MTD | 0.0261 | 1.000 | No |
| MTM20 – 2/3 MTD vs. MTM – MTD | 0.0449 | 1.000 | No |
| MTM – MTD vs. MTM – 2/3 MTD | 0.624 | 1.000 | No |
| MTM20 – MTD vs. MTM – MTD | 0.201 | 1.000 | No |
| Vehicle vs. MTM – 2/3 MTD | 1.971 | 1.000 | No |
| Vehicle vs. MTM – MTD | 1.962 | 1.000 | No |

Figure 5:
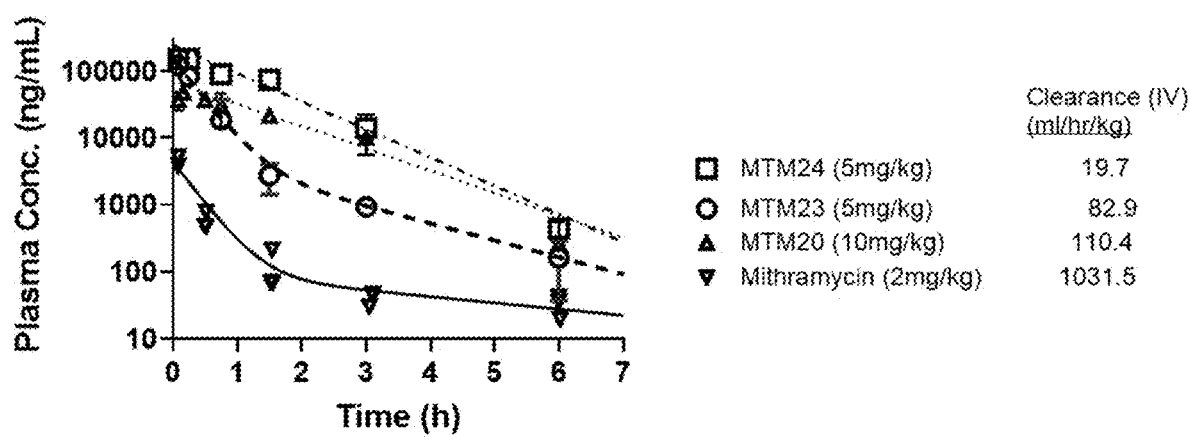
FIG. 5 includes mouse pharmacokinetic data for MTM and exemplary compounds as disclosed herein.

Reference is made to FIG. 5. MTM and exemplary compounds MTM(24), MTM(23), MTM(20) were each administered as an IV bolus injection to assess the pharmacokinetics in mice. Estimation of clearance was done by fitting data to 1- or 2-compartment pharmacokinetic models. The MTM analogues have ~10 to 50-fold lower clearance than mithramycin.

Figure 6A:
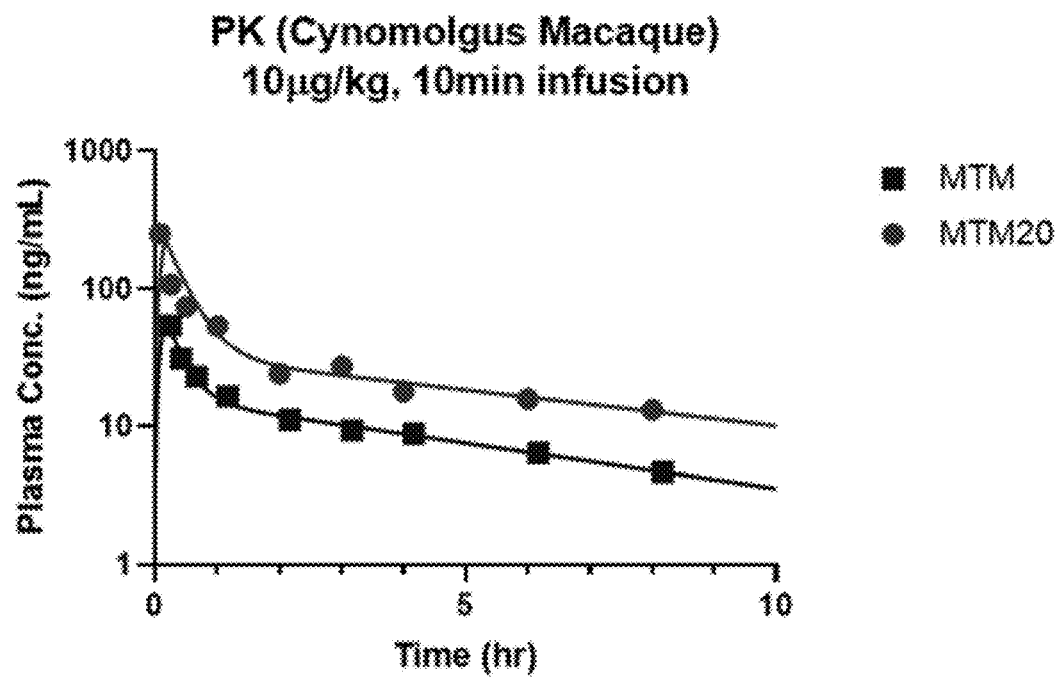
FIGS. 6A and 6B include monkey pharmacokinetic data for MTM and an exemplary compound as disclosed herein.
Figure 6B:
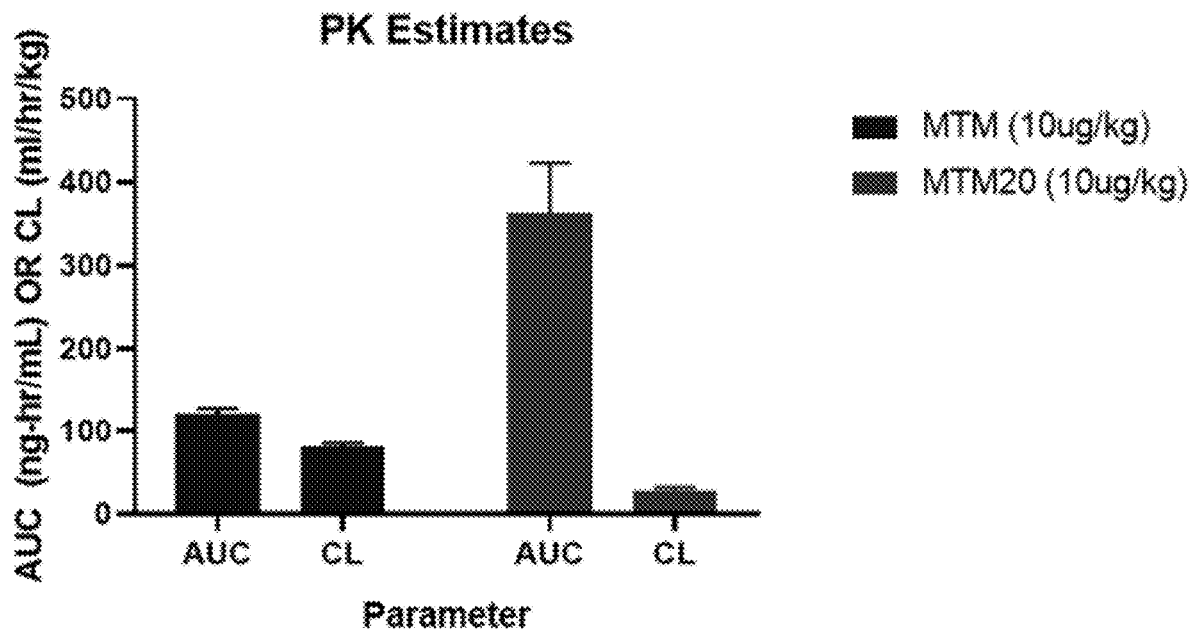
Figure 7A:
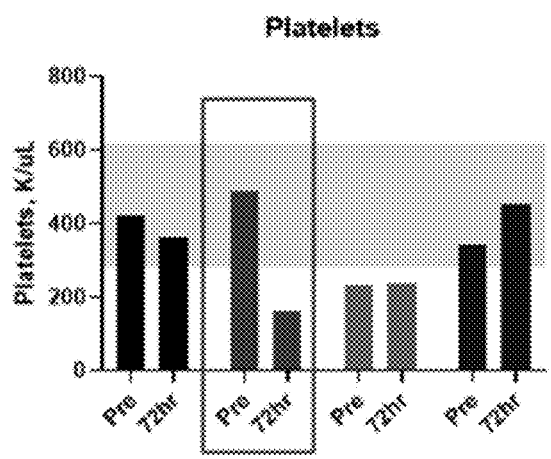
FIGS. 7A-7F include data for a hematology profile in monkeys.
Figure 7B:
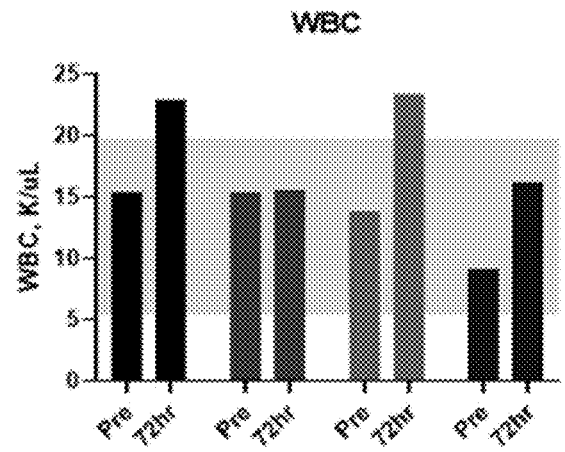
Figure 7C:
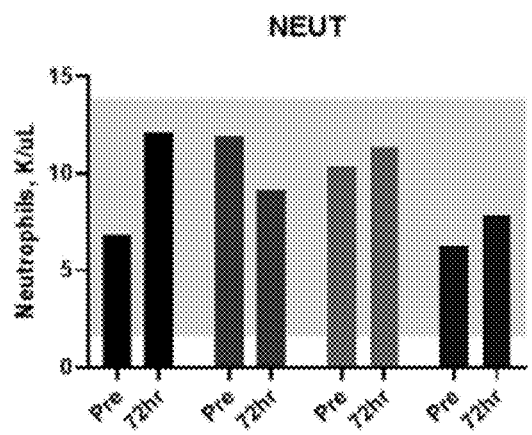
Figure 7D:
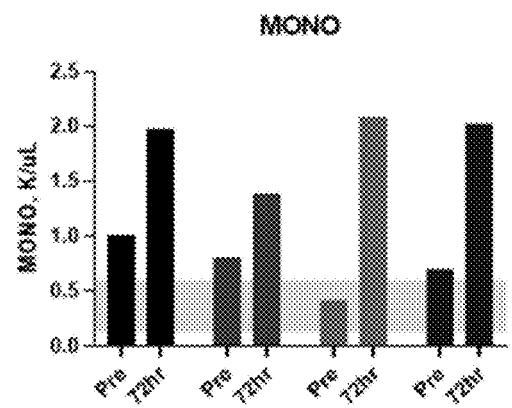
Figure 7E:
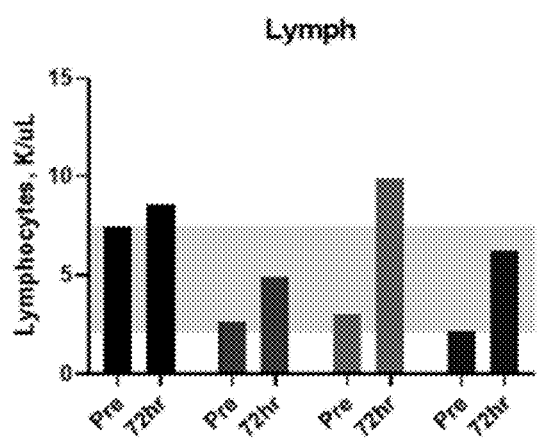
Figure 7F:
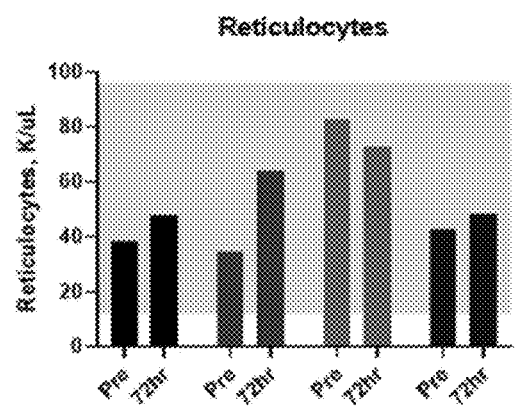

Reference is made to FIGS. 6A and 6B. MTM and exemplary compound MTM(20) were each administered as an IV bolus injection (10 mg/kg) to assess the pharmacokinetics in a single monkey. Estimation of the area under the curve (AUC) was done by 2-compartment modeling. MTM20 has ~3-fold lower clearance (CL) than mithramycin, which corresponds to an equivalent increase in exposure as measured by the AUC.

Reference is made to FIGS. 7A-7F, which include include data for a hematology profile in monkeys. MTM and MTM20 were dosed as an IV bolus injection (10 mg/kg and 15 mg/kg) in two monkeys each to assess toxicity. MTM at 15 mg/kg caused significant reduction in platelets counts. Gray areas are reference values.

Figure 8A:
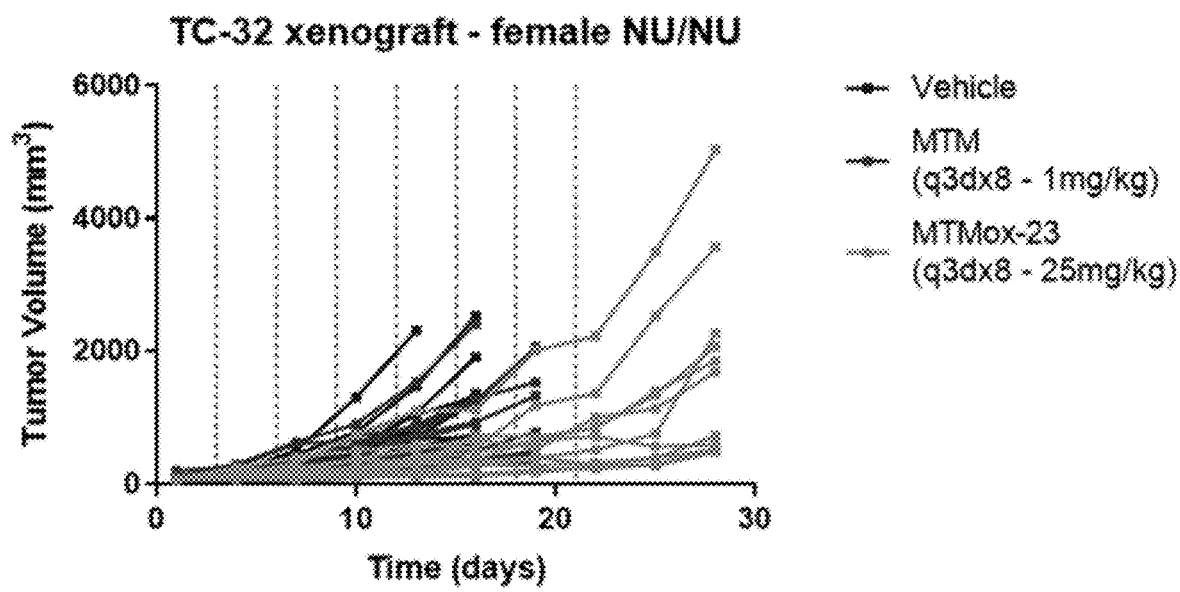
FIGS. 8A-8C include data from another efficacy study involving an exemplary compound as disclosed herein, in which TC-32 cells (EWS-FLI1+) were subcutaneously implanted in female NU/NU mice.
Figure 8B:
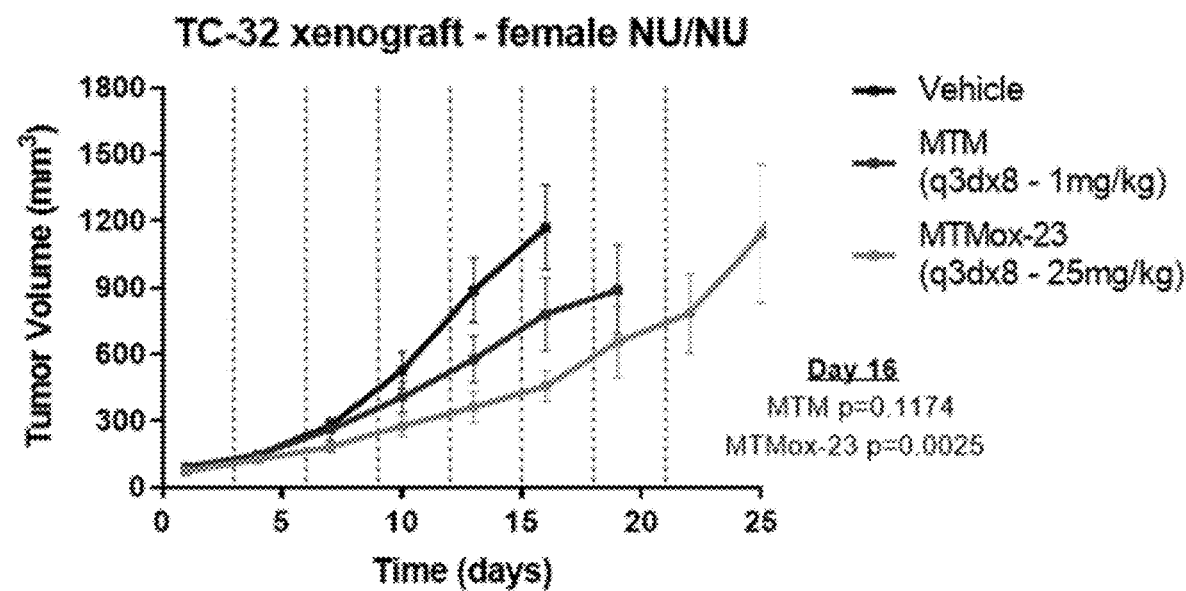
Figure 8C:
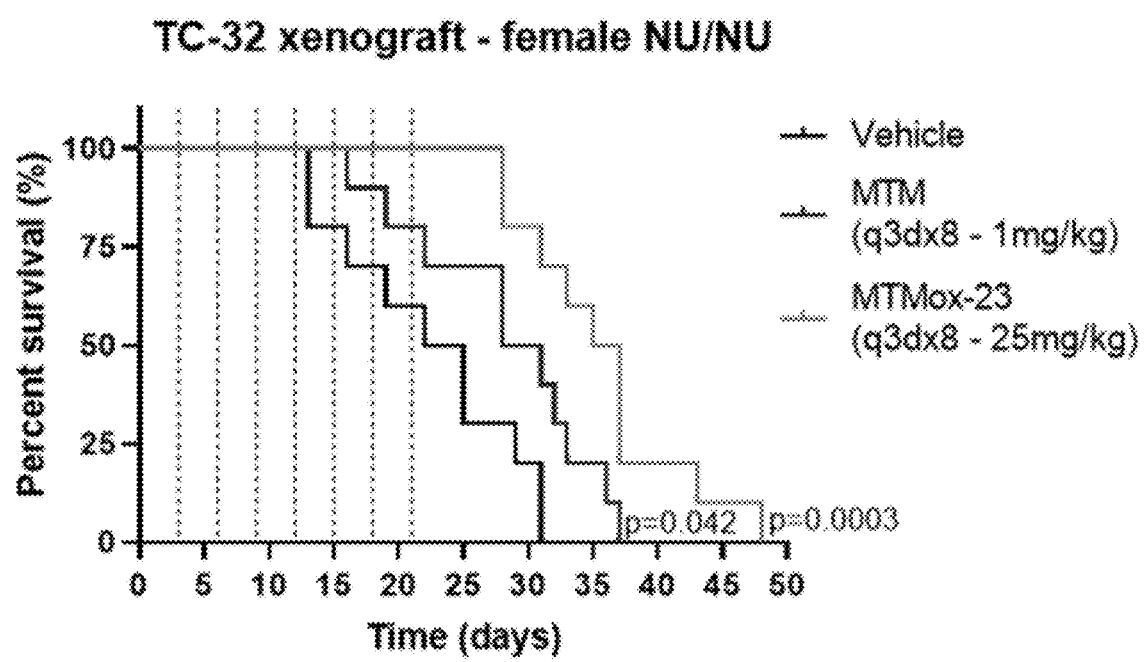

Reference is made to FIGS. 8A-8C, which include data from an efficacy study involving exemplary compound MTM (23). TC-32 cells (EWS-FLI1+) were subcutaneously implanted in female NU/NU mice. FIG. 8A includes individual mouse tumor volumes, FIG. 8B includes average tumor volumes, and FIG. 8C includes survival of mice (n=10/group) treated with MTM and MTMox-23 at respective single-dose maximum tolerated doses (MTDs) were compared to treatment with vehicle. Treatments were administered every 3 days for 8 injections (q3dx8) by intravenous bolus doses (vertical - - - ). Significance (p-value<0.05) of treatment on average tumor volume was determined 16 days after the initial dose using one-way ANOVA adjusted for multiple comparisons. Similarly, significance of treatment on survival was determined using Log-Rank (Mantel-Cox), single comparison to vehicle.

Figure 9A:
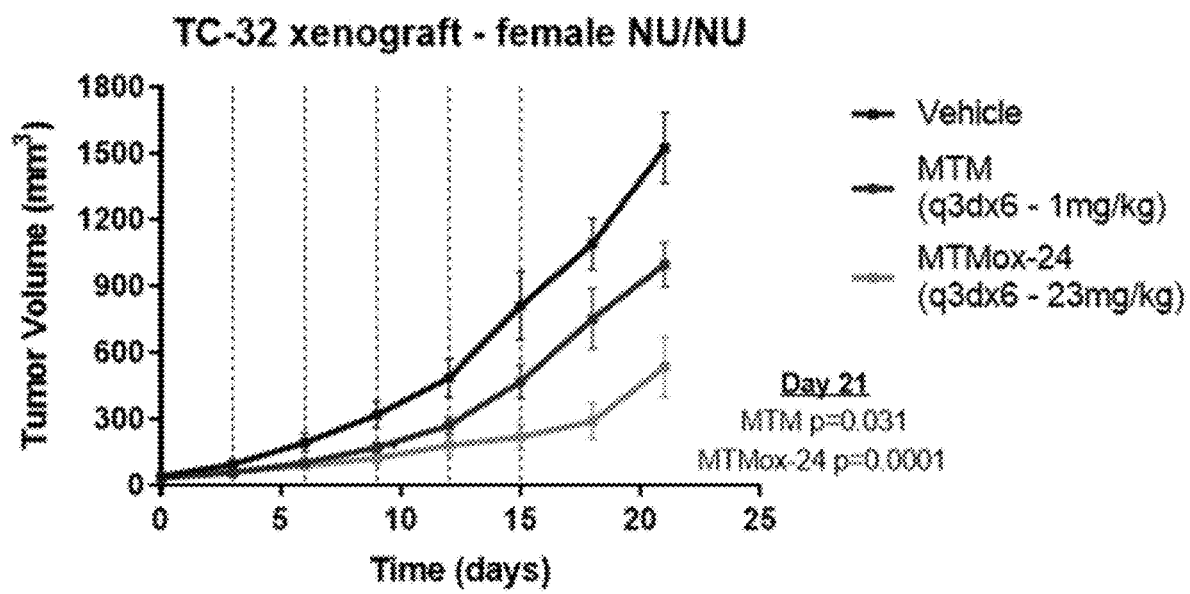
FIGS. 9A and 9B, which include data from another efficacy study involving exemplary compound as disclosed herein, in which TC-32 cells (EWS-FLI1+) were subcutaneously implanted in female NU/NU mice.
Figure 9B:
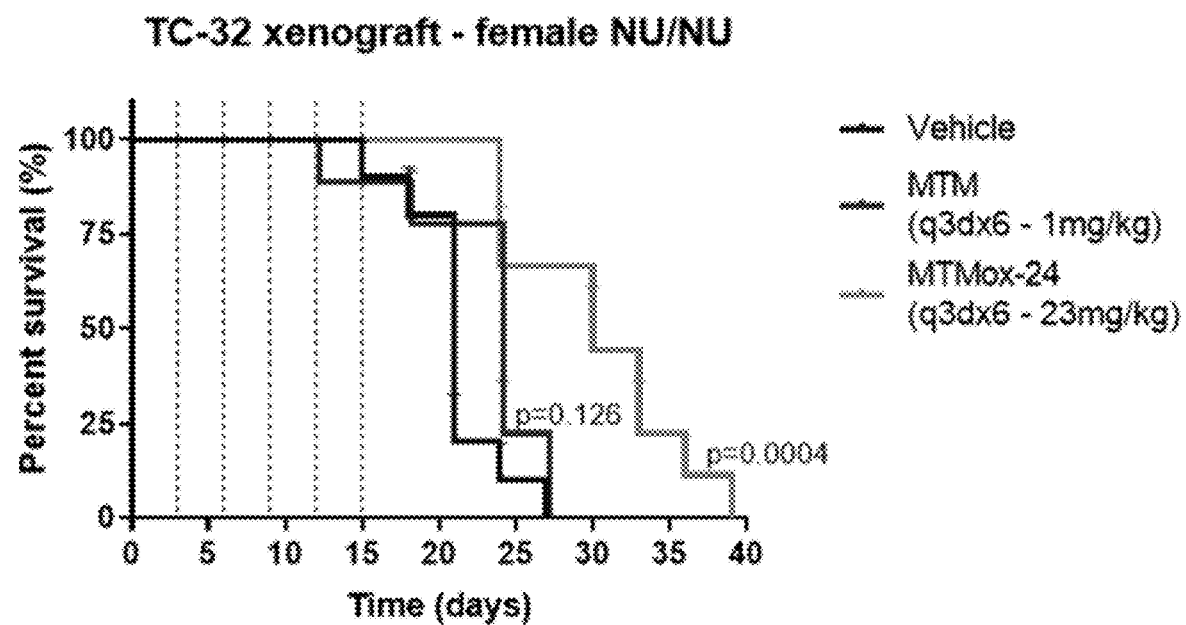

Reference is made to FIGS. 9A and 9B, which include data from an efficacy study involving exemplary compound MTM (24). TC-32 cells (EWS-FLI1+) were subcutaneously implanted in female NU/NU mice. FIG. 9A includes average tumor volume, and FIG. 9B includes survival of mice (n=10/group) treated with MTM and MTMox-24 at respective single-dose maximum tolerated doses (MTDs) were compared to treatment with vehicle. Treatments were administered every 3 days for 6 injections (q3dx6) by intravenous bolus doses (vertical - - - ). Significance (p-value<0.05) of treatment on average tumor volume was determined 21 days after the initial dose using one-way ANOVA adjusted for multiple comparisons. Similarly, significance of treatment on survival was determined using Log-Rank (Mantel-Cox), single comparison to vehicle.

Further Efficacy Studies. Additional efficacy studies are ongoing with MTM20 at a daily schedule (total of 5 doses). Compared to the every-other-day×8 doses schedule (q2Dx8), the initial response to MTM20 in two experiments (more details as follows) has significantly improved with new dosing schedules. Considering the relative changes in tumor volumes, it is predicted that the standard clinical dosing daily×5×2 weeks (qDx5x2w) regimen will be found to be notably efficacious and potentially curative.

Experiment 1—Animals bearing TC32 tumors (75-250 mm3; Avg 140 mm3) are treated with ⅔ of the maximum tolerated dose at this schedule (14.7 mg/kg) and 2 days after the end of treatment, one animal has progressed, one animal has stable disease, 7 animals have greater than 50% reduction in tumor volume, and one animal has no visible signs of tumor. In comparison, nine of 10 tumor volumes, in the control group have increased by 50% or more and one increased approximately 15% above baseline.

Experiment 2—Animals bearing TC32 tumors (75-240 mm3; Avg 130 mm3) are treated at the full MTD of the daily×5 schedule (24 mg/kg) and following the $4^{th}$ dose tumor volumes uniformly decreased by 10-70% of the original tumor volume. In comparison all tumors in the control group grow by 30% or more relative to baseline.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Wohlert, S.; Künzel, E.; Machinek, R.; Mendez, C.; Salas, J.; Rohr, J. The structure of mithramycin reinvestigated. *J. Nat. Prod.* 1999, 62, 119-121.
2. Rohr, J.; Méndez, C.; Salas, J. A. The biosynthesis of aureolic acid group antibiotics. *Bioorg. Chem.* 1999, 27, 41-54.
3. Kofman, S., Perlia, C. P, Economou, S. G. Mithramycin in the treatment of metastatic ewing's sarcoma. *Cancer* 1973, 31, 889-893.; b) Balamuth, N., Womer, R. B.: Ewing's sarcoma, *Lancet Oncol.* 2010, 11, 184-192.
4. (a) Kofman, S.; Eisenstein, R. Mithramycin in the treatment of disseminated cancer. *Cancer Chemother. Rep.* 1963, 32, 77-96.; (b) Kofman, S.; Medrek, T. J.; Alexander, R. W. Mithramycin in the treatment of embryonal cancer. *Cancer* 1964, 17, 938-948.
5. Delattre, O.; Zucman, J.; Plougastel, B.; Desmaze, C.; Melot, T.; Peter, M.; Kovar, H.; Joubert, I.; de Jong, P.; Rouleau, G. Gene fusion with an ETS DNA-binding domain caused by chromosome translocation in human tumours. *Nature* 1992, 359, 162.
6. May, W. A.; Arvand, A.; Thompson, A. D.; Braun, B. S.; Wright, M.; Denny, C. T. EWS/FLI1-induced manic fringe renders NIH 3T3 cells tumorigenic. *Nat. Genet.* 1997, 17, 495-497.
7. Tomlins, S. A.; Rhodes, D. R., Perner, S., Dhanasekaran, S. M., Mehra, R., Sun, X. W., Varambally, S., Cao, X., Tchinda, J., Kuefer, R. and Lee, C. Recurrent fusion of TMPRSS2 and ETS transcription factor genes in prostate cancer. *Science,* 2005, 310, 644-648.
8. Sastry, M.; Patel, D. J. Solution structure of the mithramycin dimer-DNA complex. *Biochemistry* 1993, 32, 6588-6604.
9. Remsing, L. L.; Gonzalez, A. M.; Nur-e-Alam, M.; Fernandez-Lozano, M. J.; Braria, A. F.; Rix, U.; Oliveira, M. A.; Mendez, C.; Salas, J. A.; Rohr, J. Mithramycin SK, a novel antitumor drug with improved therapeutic index, mithramycin SA, and demycarosyl-mithramycin SK: three new products generated in the mithramycin producer *Streptomyces argillaceus* through combinatorial biosynthesis. *J. Am. Chem. Soc.* 2003, 125, 5745-5753.
10. Scott, D.; Chen, J. M.; Bae, Y.; Rohr, J. Semi-synthetic mithramycin SA derivatives with improved anti-cancer activity. *Chem. Biol. Drug. Des.* 2013, 81, 615-624.
11. Leggas, M.; Eckenrode, J.; Mitra, P.; Jha, J.; Salem, S.; Mandal, A.; Thorson, J.; Rohr, J. [abstract]. In: Proceedings of the AACR-NCI-EORTC international conference: molecular targets and cancer therapeutics; 2017 Oct. 26-30; Philadelphia, Pa. Philadelphia (Pa.): AACR; *Mol Cancer Ther.* 2018, 17 (1 Suppl):Abstract nr B043.
12. Hou, C.; Weidenbach, S.; Cano, K. E.; Wang, Z.; Mitra, P.; Ivanov, D. N.; Rohr, J.; Tsodikov, O. V. Structures of mithramycin analogues bound to DNA and implications for targeting transcription factor FLI1. *Nucleic Acids Res.* 2016, 44, 8990-9004.
13. Alqahtani, N.; Porwal, S. K.; James, E. D.; Bis, D. M.; Karty, J. A.; Lane, A. L.; Viswanathan, R. Synergism between genome sequencing, tandem mass spectrometry and bio-inspired synthesis reveals insights into nocardioazine B biogenesis. *Org. Biomol. Chem.* 2015, 13, 7177-7192.
14. Cardoso, A. S. P.; Marques, M. M. B.; Srinivasan, N.; Prabhakar, S.; Lobo, A. M.; Rzepa, H. S. Studies in sigmatropic rearrangements of N-prenylindole derivatives—a formal enantiomerically pure synthesis of tryprostatin B. *Org. Biomol. Chem.* 2006, 4, 3966-3972.
15. Loach, R. P.; Fenton, O. S.; Amaike, K.; Siegel, D. S.; Ozkal, E.; Movassaghi, M. Derivatization of C3-alkylindoles including tryptophans and tryptamines. *J. Org. Chem.* 2014, 79, 11254-11263.
16. Partridge, B. M.; Hartwig, J. F. Sterically controlled iodination of arenes via iridium-catalyzed C—H borylation. *Org. Lett.* 2012, 15, 140-143.
17. Feng, Y.; Holte, D.; Zoller, J.; Umemiya, S.; Simke, L. R.; Baran, P. S. Total synthesis of erruculogen and fumitremorgin a enabled by ligand-controlled CH borylation. *J. Am. Chem. Soc.* 2015, 137, 10160-10163.
18. Jia, Y.; Zhu, J. Palladium-catalyzed, modular synthesis of highly functionalized indoles and tryptophans by direct annulation of substituted o-haloanilines and aldehydes. *J. Org. Chem.* 2006, 71, 7826-7834.
19. Kokotos, G.; Padron, J. M.; Martin, T.; Gibbons, W. A.; Martin, V. S. A general approach to the asymmetric synthesis of unsaturated lipidic α-amino acids. The first synthesis of α-aminoarachidonic acid. *J. Org. Chem.* 1998, 63, 3741-3744.
20. Bi, W.; Bi, Y.; Xue, P.; Zhang, Y.; Gao, X.; Wang, Z.; Li, M.; Baudy-Floc'h, M.; Ngerebara, N.; Li, X. Novel β-carboline-tripeptide conjugates attenuate mesenteric ischemia/reperfusion injury in the rat. *Eur. J. Med. Chem.* 2011, 46, 2441-2452.
21. Coste, A.; Toumi, M.; Wright, K.; Razafimahaleo, V.; Couty, F.; Marrot, J.; Evano, G. Copper-catalyzed cyclization of iodo-tryptophans: A straightforward synthesis of pyrroloindoles. *Org. Lett.* 2008, 10, 3841-3844.
22. Cozett, R. E.; Venter, G. A.; Gokada, M. R.; Hunter, R. Catalytic enantioselective acyl transfer: the case for 4-PPY with a C-3 carboxamide peptide auxiliary based on synthesis and modelling studies. *Org. Biomol. Chem.* 2016, 14, 10914-10925.
23. Choi, J. Y.; Calvet, C. M.; Gunatilleke, S. S.; Ruiz, C.; Cameron, M. D.; McKerrow, J. H.; Podust, L. M.; Roush, W. R. Rational development of 4-aminopyridyl-based inhibitors targeting *Trypanosoma cruzi* CYP51 as anti-chagas agents. *J. Med. Chem.* 2013, 56, 7651-7668.
24. Osgood, C. L.; Maloney, N.; Kidd, C. G.; Kitchen-Goosen, S.; Segars, L.; Gebregiorgis, M.; Woldemichael, G. M.; He, M.; Sankar, S.; Lessnick, S. L.; Kang, M.; Smith, M.; Turner, L.; Madaj, Z. B.; Winn, M. E.; Núñez, L. E.; González-Sabín, Z.; Heiman, L. J.; Moris, F.; Grohar, P. J. Identification of mithramycin analogues with improved targeting of the EWS-FLI1 transcription factor. *Clin. Cancer Res.* 2016, 22, 4105-4118.
25. Garcia-Aragoncillo, E., J. Carrillo, E. Lalli, N. Agra, G. Gomez-Lopez, A. Pestana, and J. Alonso. "DAX1, a direct target of EWS/FLI1 oncoprotein, is a principal regulator of cell-cycle progression in ewing's tumor cells." *Oncogene* 2008, 27, 6034-6043.
26. Grohar, P. J.; Woldemichael, G. M.; Griffin, L. B.; Mendoza, A.; Chen, Q.-R.; Yeung, C.; Currier, D. G.; Davis, S.; Khanna, C.; Khan, J. Identification of an inhibitor of the EWS-FLI1 oncogenic transcription factor by high-throughput screening. *J. Natl. Cancer Inst.* 2011, 103, 962-978.
27. U.S. Pat. No. 9,447,135 to Rohr, J. T, et al., "Semi-Synthetic Mithramycin Derivatives with Anti-Cancer Activity."
28. International Patent Application Publication No. WO 2010126626 to deLong, et al., "Preparation of isoquinolinylamide derivatives for use as dual-action monoamine transport and kinase inhibitors."
29. Eckenrode, J. M., Mitra, P., et al. *J. Med. Chem.* 2018 (61)8001.
30. Tevyashova, A. N., et al. *J. Antibiotics* (2009) 62, 37-41.

---

What is claimed is:

1. A compound having the following formula:

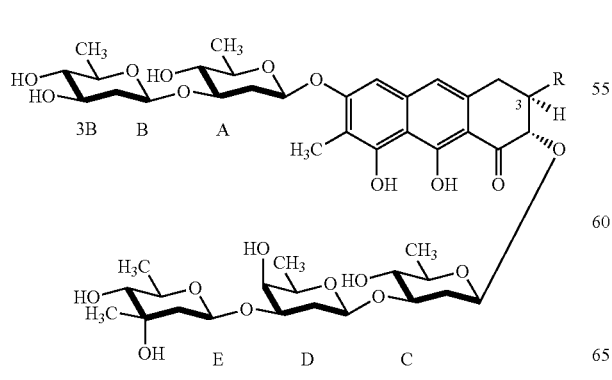

or a pharmaceutically acceptable salt thereof, wherein R is

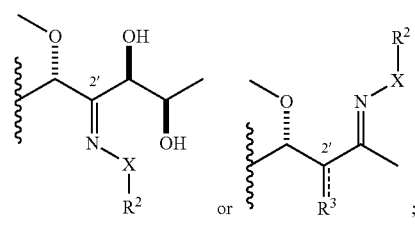

$R^2$ is OH, alkyl excluding methyl, alkylaryl, aryl, acyl, alkene, alkylalkene, alkyne, alkylalkyne, acyl, acylaryl, amino acid, amino acid dipeptide, acyl-amino acid, acyl-amino acid dipeptide, so long as $R^2$ is not $CH_2COOH$;

$R^3$ is OH; and

X is O.

2. The compound of claim 1, wherein R² is acylaryl, acyl-amino acid, or acyl-amino acid dipeptide.

3. The compound of claim 2, wherein R² is acylaryl comprising a quinolone, a benzothizole, a phenyl, a pyridine, or an indol group.

4. The compound of claim 1, wherein R² comprises a quinolone, a benzothizole, a phenyl, a pyridine, or an indol group.

5. The compound of claim 1, wherein R² comprises an amino acid or amino acid dipeptide group, or a substituted amino acid or amino acid dipeptide group.

6. A compound having the following formula:

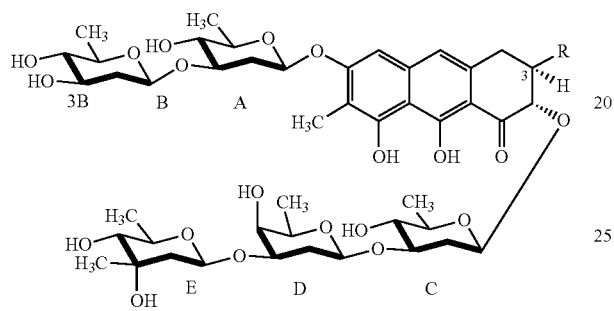

or a pharmaceutically acceptable salt thereof, wherein R is selected from the group consisting of:

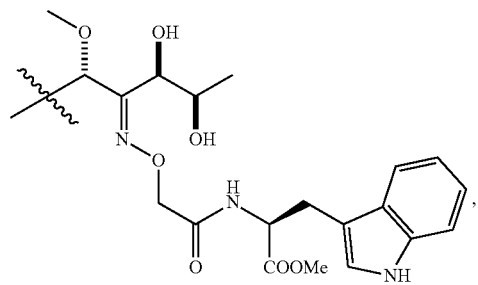

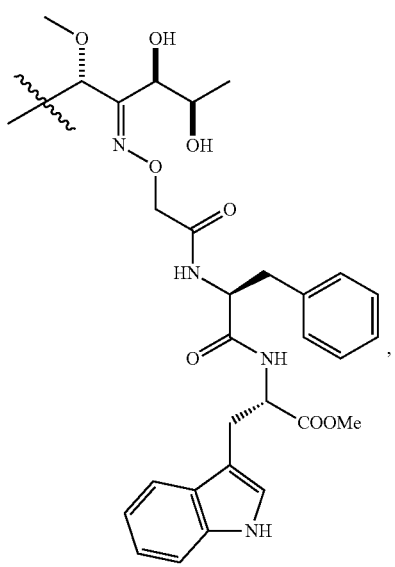

-continued

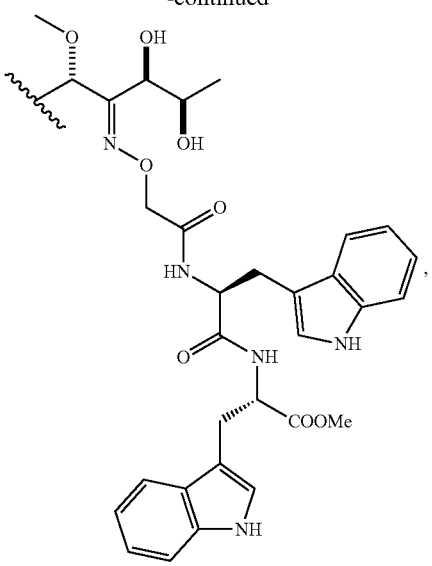

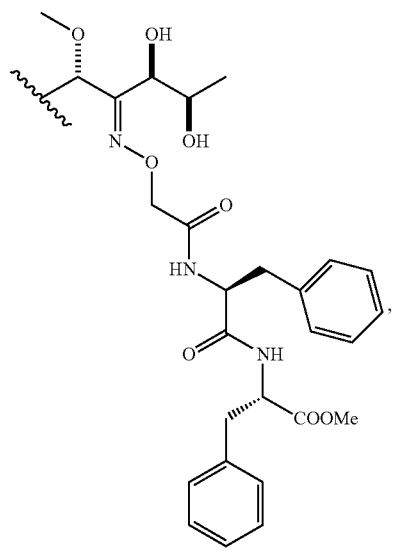

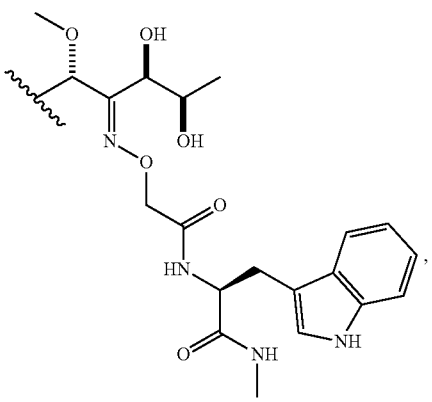

115
-continued
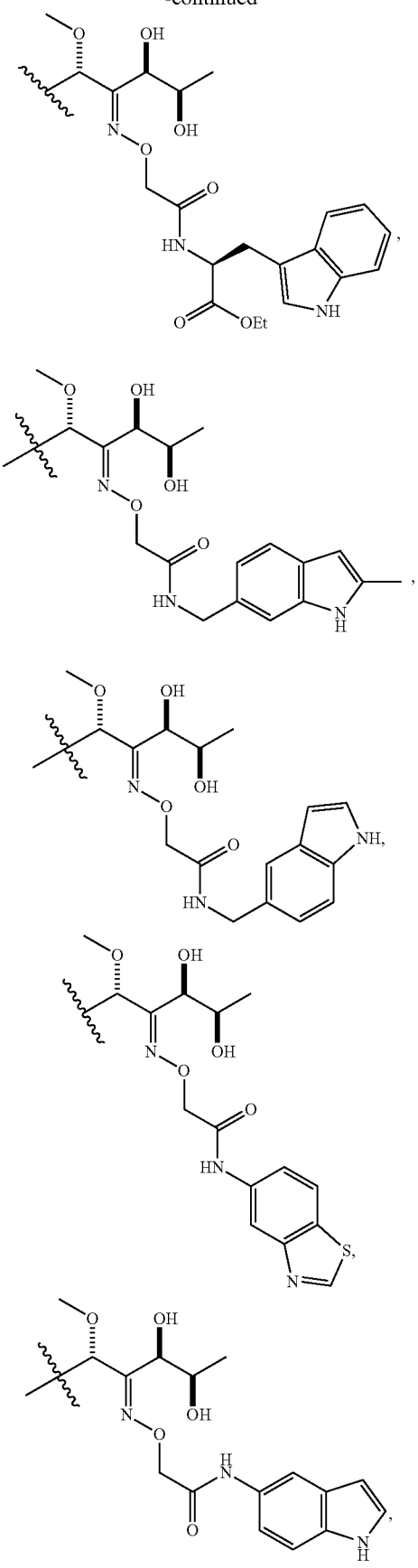
116
-continued
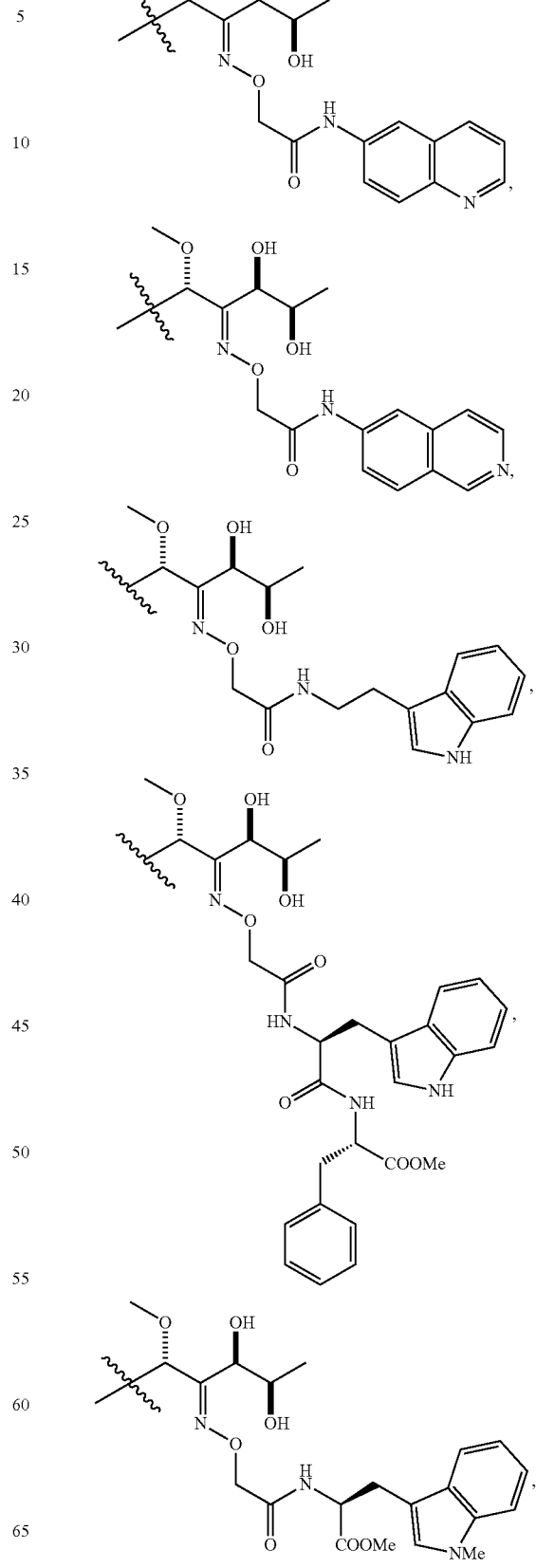

117
-continued
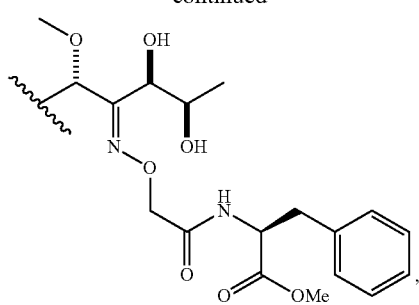,
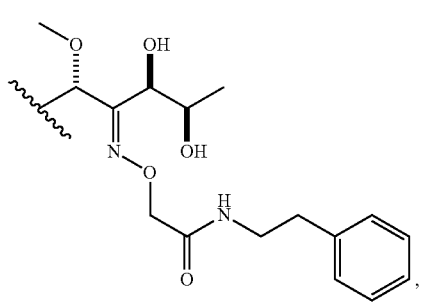,
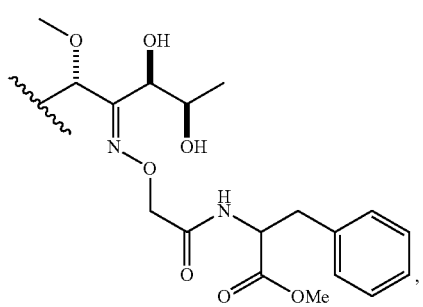,
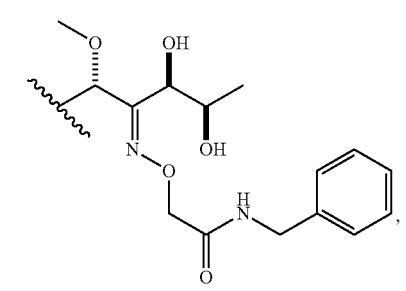,
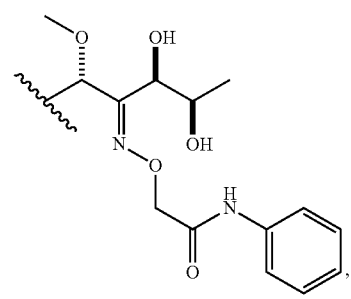,
118
-continued
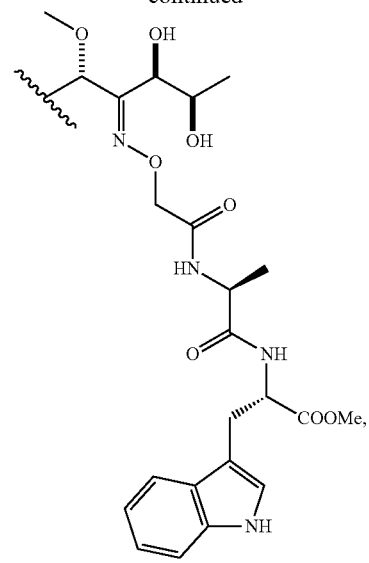,
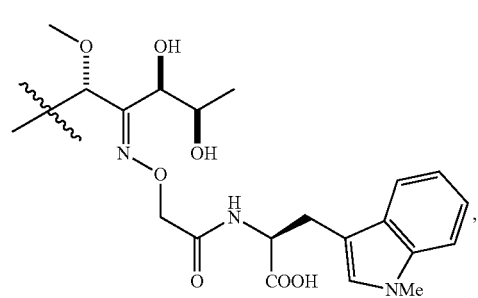,
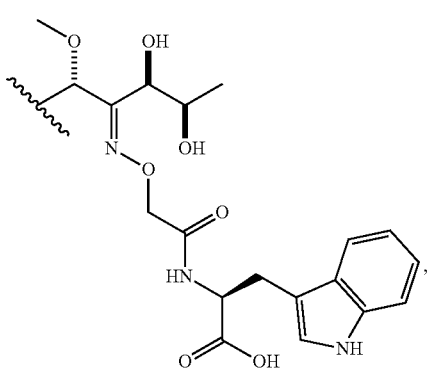,
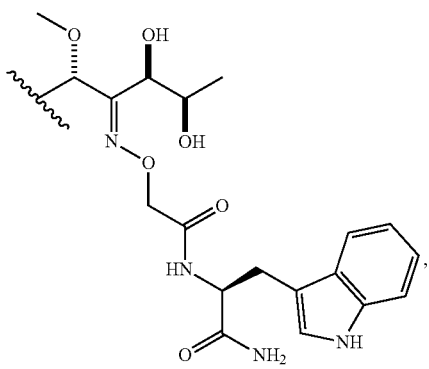, 119
-continued
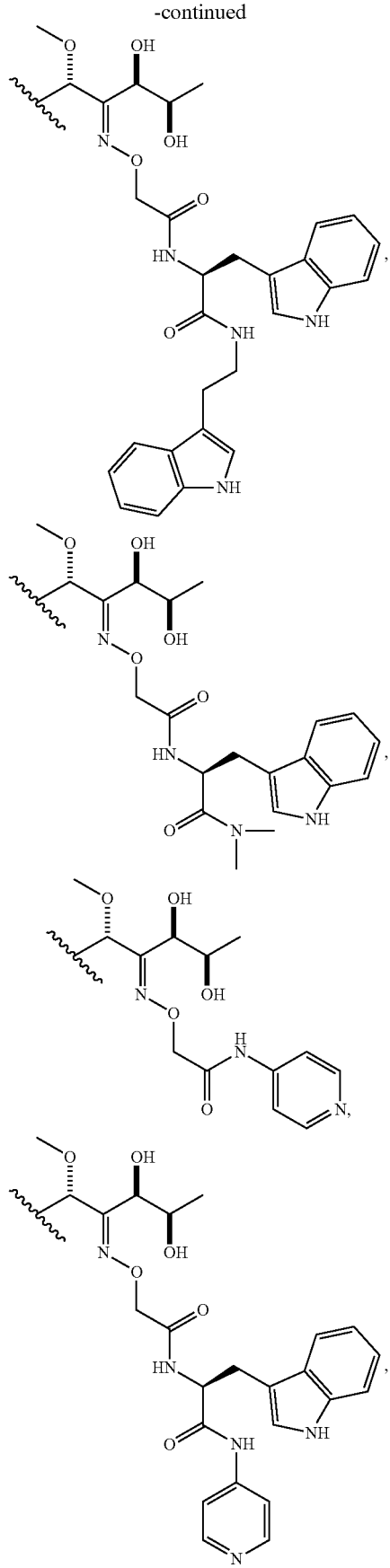
120
-continued
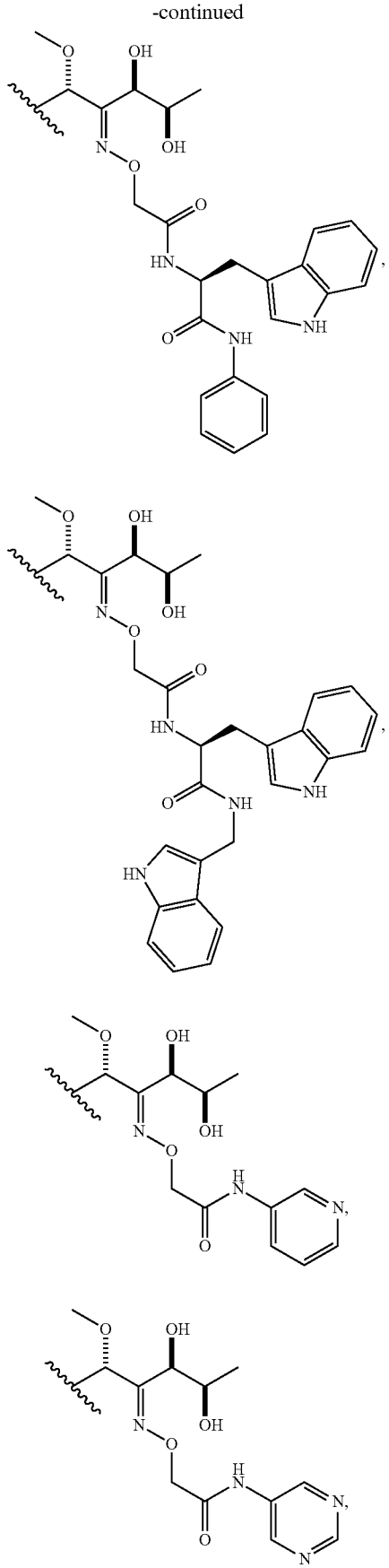

121
-continued
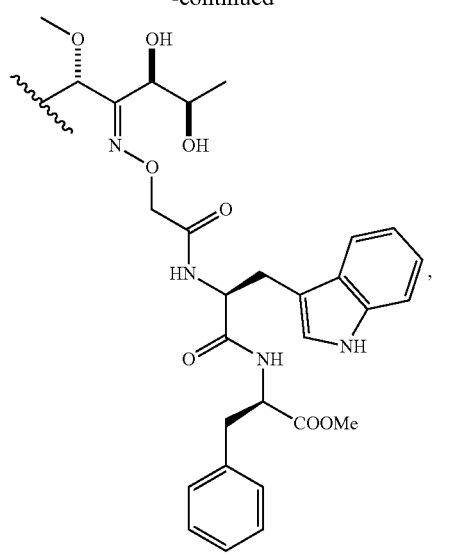
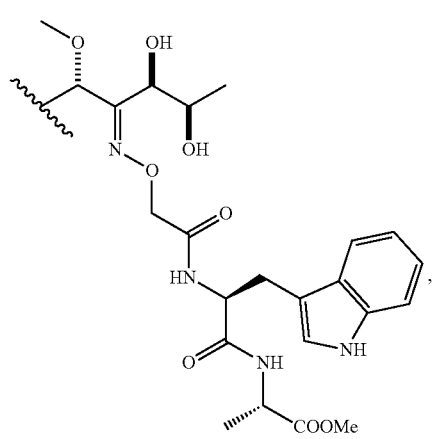
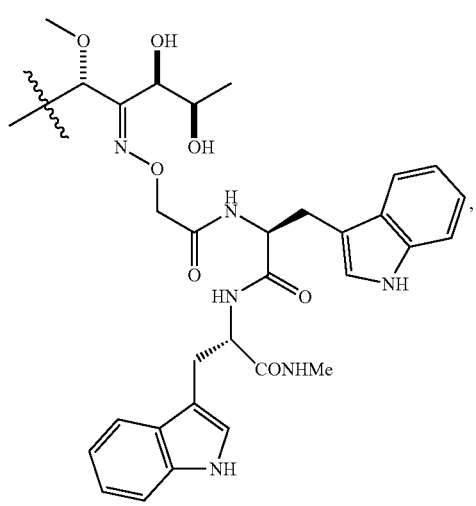
122
-continued
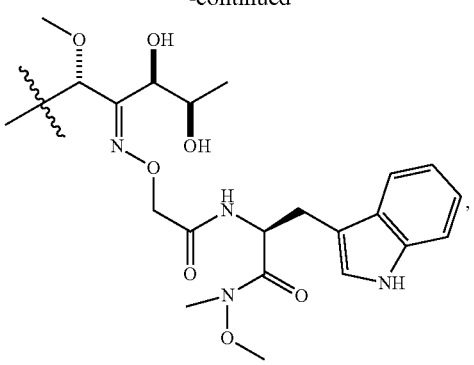
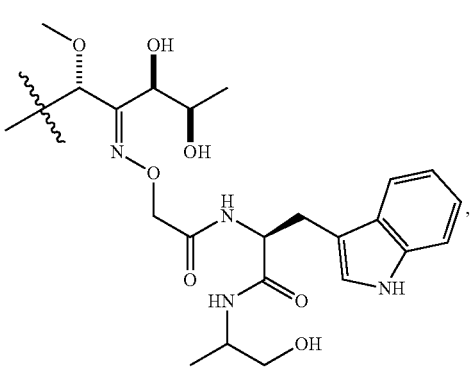
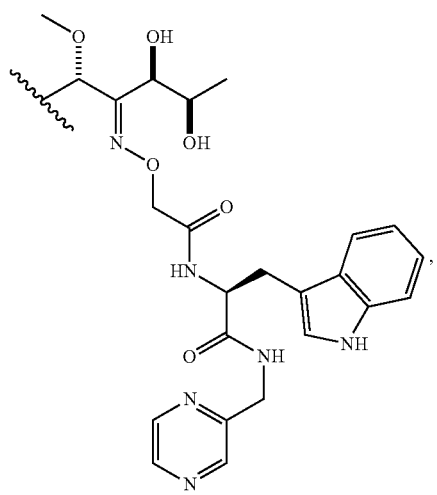
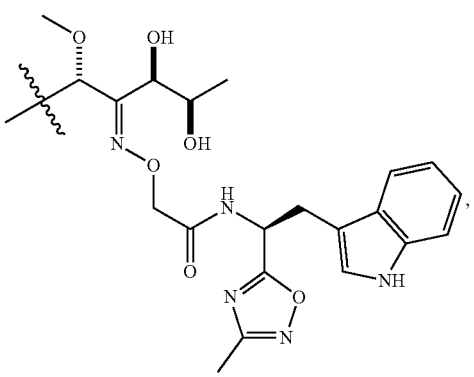

123
-continued
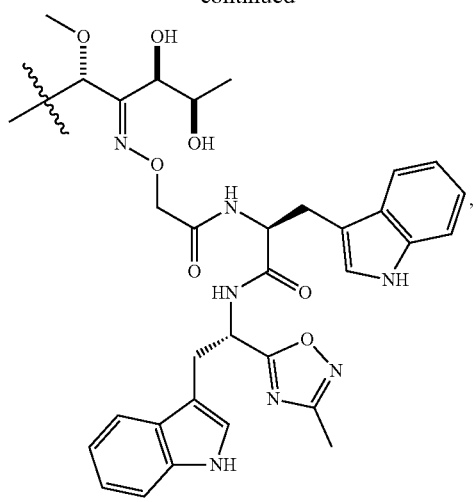
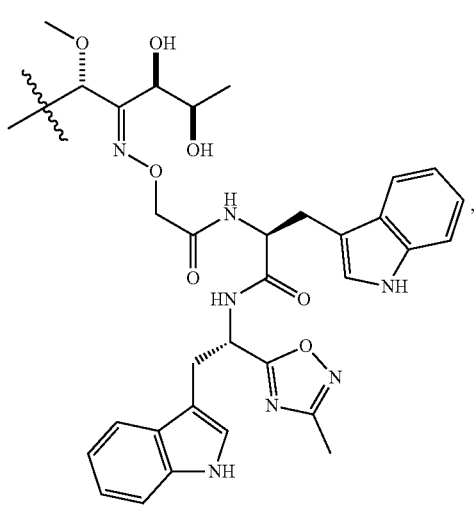
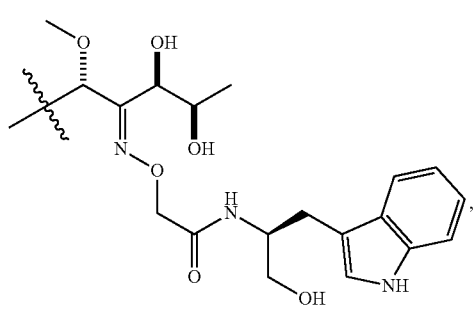
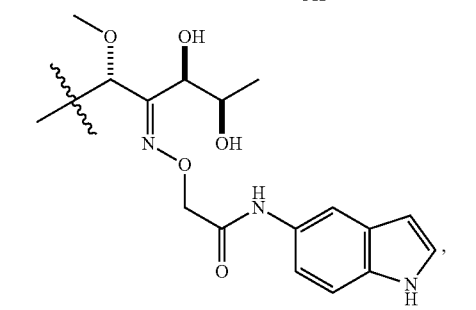
124
-continued
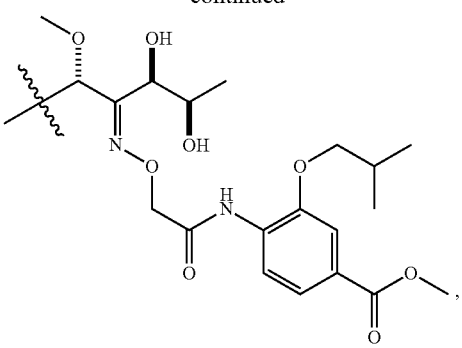
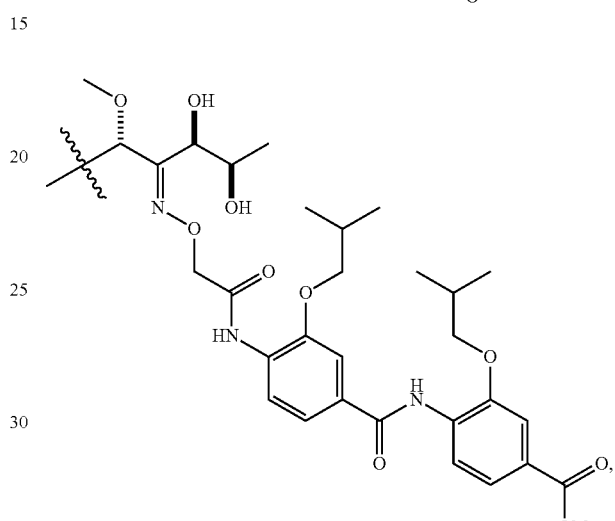
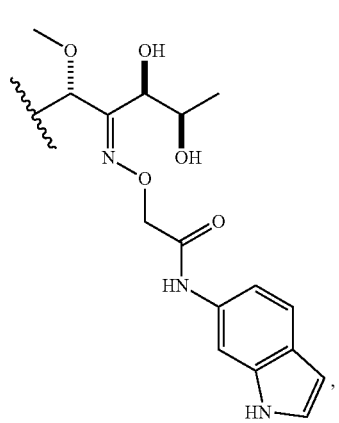
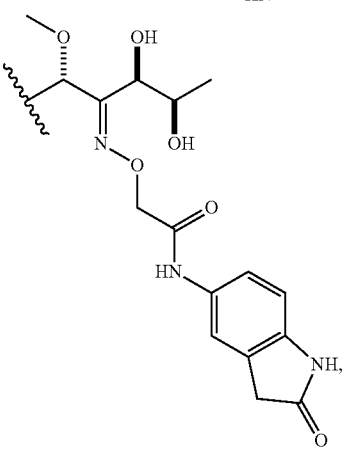

125
-continued
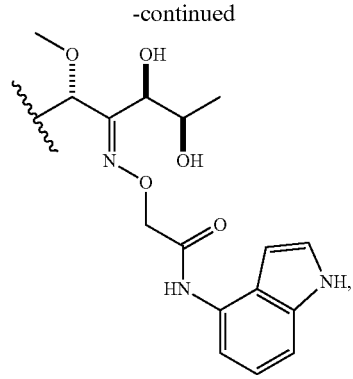
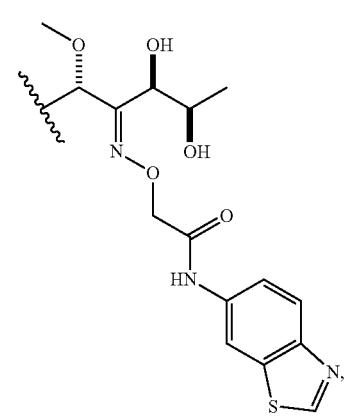
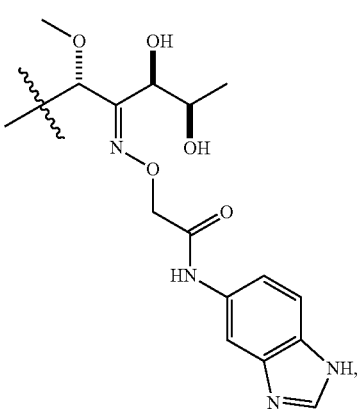
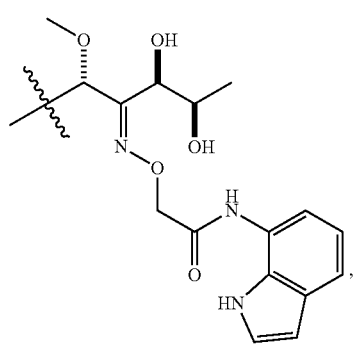
126
-continued
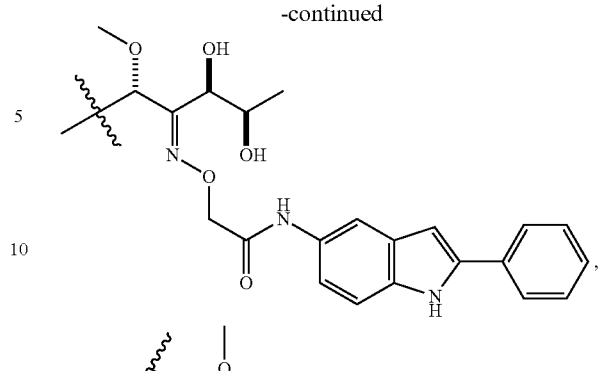
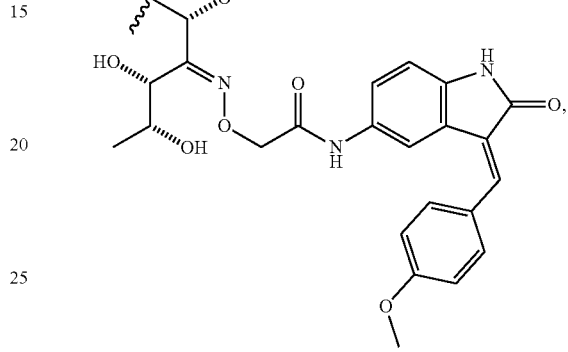
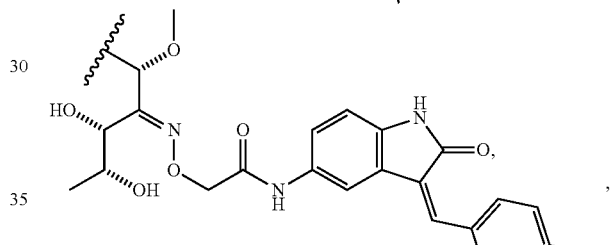
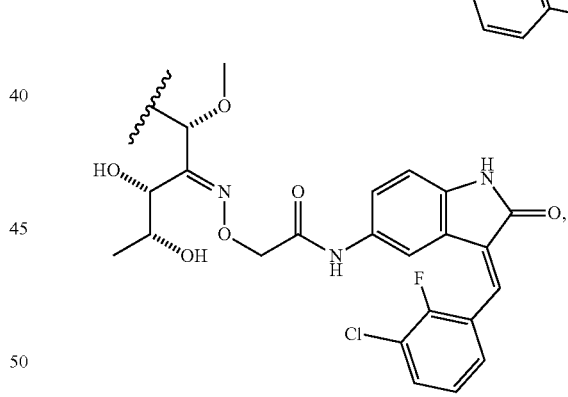
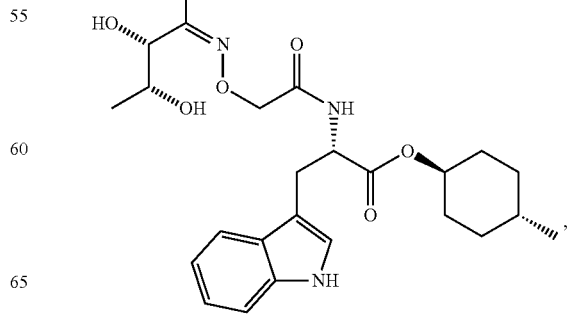

127
-continued
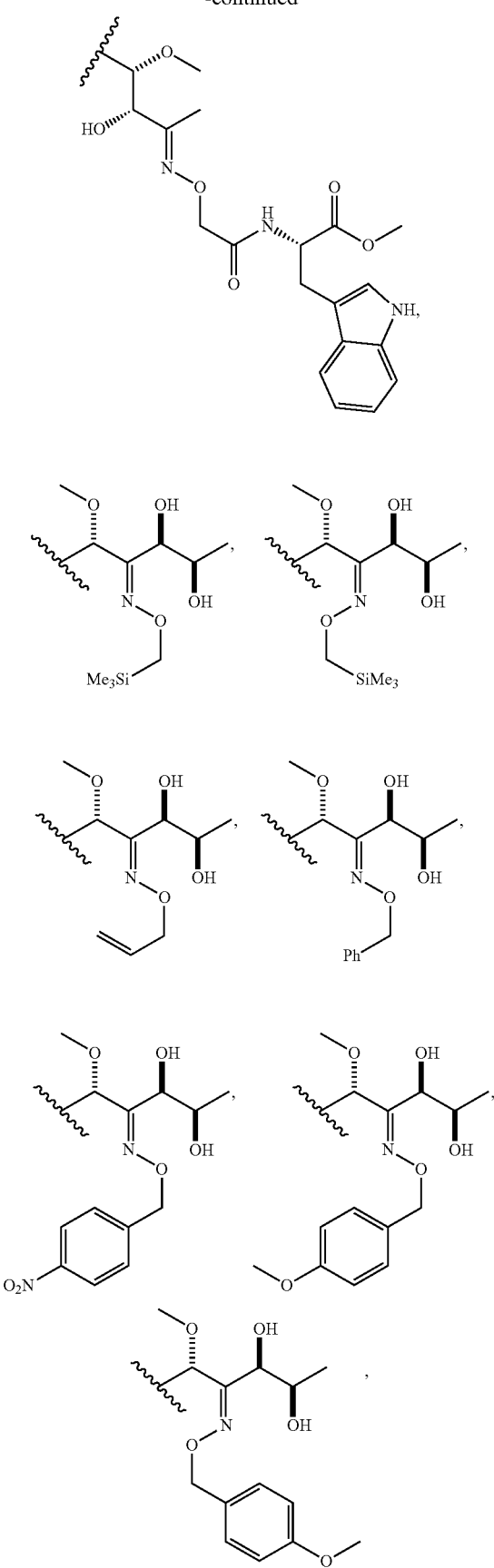
128
-continued
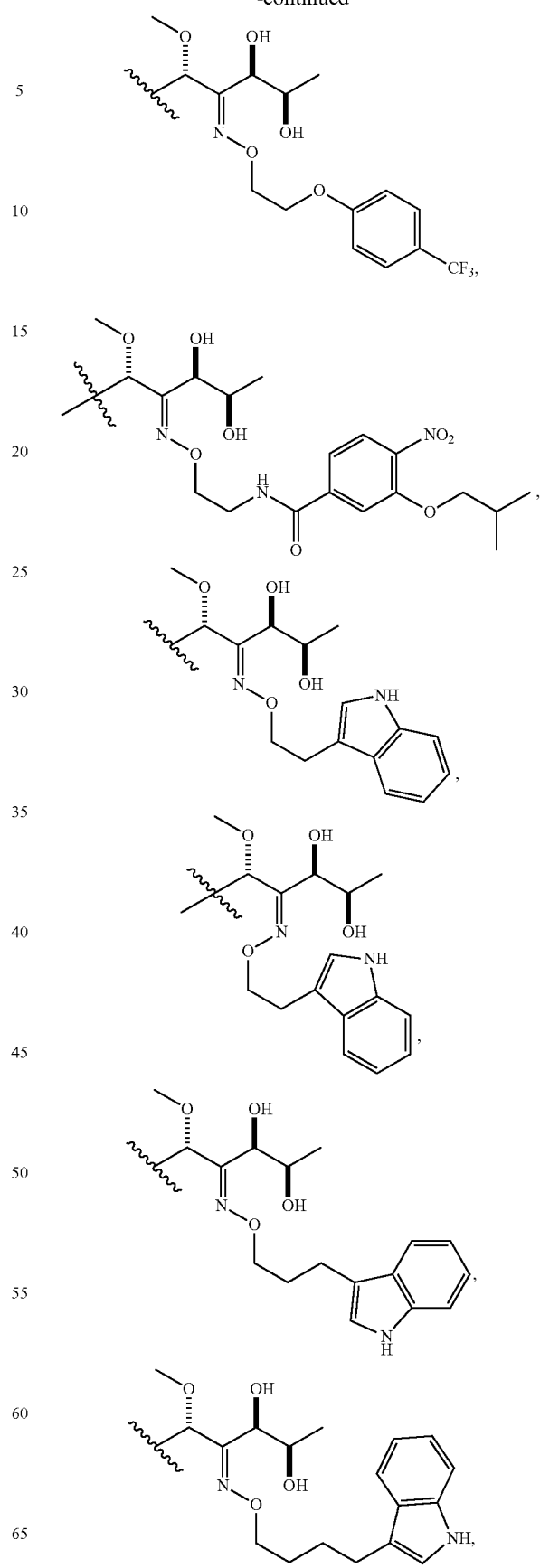

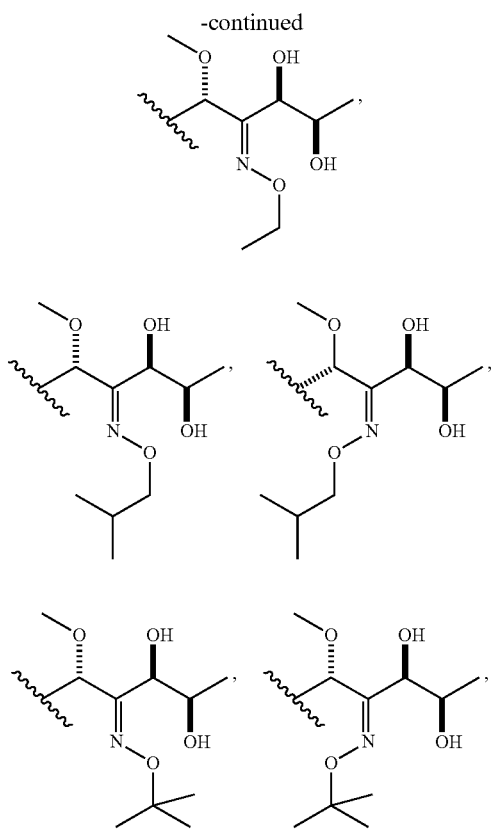

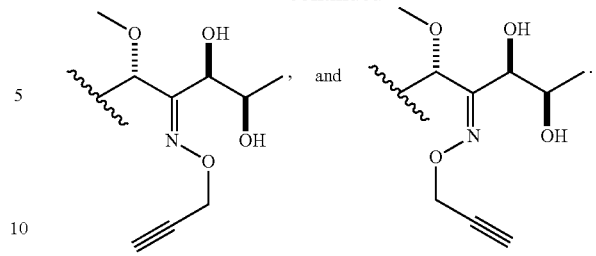

7. A method of treating cancer or neuro-disease in a patient in need thereof, the method comprising administering to the patient a therapeutically effective amount of the compound of claim 1.

8. The method of claim 7, wherein the method comprises treating Ewing sarcoma.

9. The method of claim 7, wherein the method comprises treating prostate cancer.

10. The method of claim 7, wherein the method comprises treating colon cancer.

11. The method of claim 7, wherein the method comprises treating lung cancer.

12. The method of claim 7, wherein the method comprises treating leukemia or lymphoma.

13. A method for selectively modulating the activity of a target ETS transcription factor in a patient in need thereof, including administering to the patient a therapeutically effective amount of the compound of claim 1.

* * * * *